(12) United States Patent
Casebier et al.

(10) Patent No.: US 8,226,929 B2
(45) Date of Patent: Jul. 24, 2012

(54) CONTRAST AGENTS FOR MYOCARDIAL PERFUSION IMAGING

(75) Inventors: David S. Casebier, Carlisle, MA (US); Simon P. Robinson, Stow, MA (US); Ajay Purohit, Sudbury, MA (US); Heike S. Radeke, South Grafton, MA (US); Michael T. Azure, Henniker, NH (US); Douglas D. Dischino, Middlefield, CT (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 1227 days.

(21) Appl. No.: 12/014,161

(22) Filed: Jan. 15, 2008

(65) Prior Publication Data
US 2008/0112884 A1 May 15, 2008

Related U.S. Application Data

(62) Division of application No. 11/055,498, filed on Feb. 10, 2005, now Pat. No. 7,344,702.

(60) Provisional application No. 60/544,861, filed on Feb. 13, 2004.

(51) Int. Cl.
*A61K 51/00* (2006.01)
*A61M 36/14* (2006.01)
*A01N 43/58* (2006.01)
*C07D 237/00* (2006.01)
*A61B 6/00* (2006.01)

(52) U.S. Cl. ............. 424/1.89; 424/1.11; 424/1.81; 424/1.85; 514/248; 544/239; 600/436

(58) Field of Classification Search ............... 424/1.11, 424/1.89, 1.81, 1.85; 514/248; 544/239; 600/436
See application file for complete search history.

(56) References Cited

U.S. PATENT DOCUMENTS

| | | |
|---|---|---|
| 3,359,103 A | 12/1967 | Becker et al. |
| 5,087,440 A | 2/1992 | Cacheris et al. |
| 5,088,499 A | 2/1992 | Unger |
| 5,093,105 A | 3/1992 | Flanagan et al. |
| 5,155,215 A | 10/1992 | Ranney |
| 5,169,848 A | 12/1992 | Bettarini et al. |
| 5,169,942 A | 12/1992 | Johnson |
| 5,228,446 A | 7/1993 | Unger et al. |
| 5,281,704 A | 1/1994 | Love et al. |
| 5,306,482 A | 4/1994 | Tartaglia et al. |
| 5,384,113 A | 1/1995 | Deutsch et al. |

(Continued)

FOREIGN PATENT DOCUMENTS

CN 101555232 A 10/2009

(Continued)

OTHER PUBLICATIONS

Bateman et al., Diagnostic accuracy of rest/stress ECG-gated Rb-82 myocardial perfusion PET: comparison with ECG-gated Tc-99m sestamibi SPECT. J Nucl Cardiol. Jan.-Feb. 2006;13(1):24-33.

(Continued)

*Primary Examiner* — Michael G Hartley
*Assistant Examiner* — Leah Schlientz
(74) *Attorney, Agent, or Firm* — Wolf, Greenfield & Sacks, P.C.

(57) ABSTRACT

The present disclosure is directed, in part, to compounds and methods for imaging myocardial perfusion, comprising administering to a patient a contrast agent which comprises a compound that binds MC-1, and an imaging moiety, and scanning the patient using diagnostic imaging.

4 Claims, No Drawings

U.S. PATENT DOCUMENTS

| | | | |
|---|---|---|---|
| 5,393,512 | A | 2/1995 | Vanderheyden et al. |
| 5,412,148 | A | 5/1995 | Keana |
| 5,417,959 | A | 5/1995 | Wallace |
| 5,436,325 | A | 7/1995 | Johnson et al. |
| 5,520,904 | A | 5/1996 | Nosco et al. |
| 5,547,656 | A | 8/1996 | Unger |
| 5,567,411 | A | 10/1996 | Keana et al. |
| 5,585,112 | A | 12/1996 | Unger et al. |
| 5,587,491 | A | 12/1996 | Hoye et al. |
| 5,679,810 | A | 10/1997 | Love et al. |
| 5,760,191 | A | 6/1998 | Snow et al. |
| 5,801,228 | A | 9/1998 | Hollister et al. |
| 5,804,161 | A | 9/1998 | Long et al. |
| 5,846,517 | A | 12/1998 | Unger |
| 5,961,955 | A | 10/1999 | Shochat et al. |
| 6,056,939 | A | 5/2000 | Desreux et al. |
| 6,066,309 | A | 5/2000 | Zamora et al. |
| 6,241,964 | B1 | 6/2001 | Burns et al. |
| 6,565,889 | B2 | 5/2003 | Zasadzinski et al. |
| 7,112,318 | B2 | 9/2006 | Madar et al. |
| 7,344,702 | B2 | 3/2008 | Casebier et al. |
| 7,410,998 | B2 | 8/2008 | Nicolaou et al. |
| 7,485,283 | B2 | 2/2009 | Radeke et al. |
| 7,824,659 | B2 | 11/2010 | Casebier et al. |
| 7,847,092 | B2 | 12/2010 | Moon et al. |
| 2003/0044354 | A1 | 3/2003 | Carpenter et al. |
| 2003/0124054 | A1 | 7/2003 | Toyohara et al. |
| 2004/0033197 | A1 | 2/2004 | Madar et al. |
| 2004/0034239 | A1 | 2/2004 | Nicolaou et al. |
| 2005/0191238 | A1 | 9/2005 | Casebier et al. |
| 2005/0244332 | A1 | 11/2005 | Radeke et al. |
| 2006/0083681 | A1 | 4/2006 | Purohit et al. |
| 2007/0036716 | A1 | 2/2007 | Casebier et al. |
| 2007/0082879 | A1 | 4/2007 | Goodman |
| 2009/0104118 | A1 | 4/2009 | Radeke et al. |
| 2009/0297442 | A1 | 12/2009 | Hemstad |
| 2010/0236958 | A1 | 9/2010 | Veggeland et al. |
| 2011/0091374 | A1 | 4/2011 | Robinson et al. |

FOREIGN PATENT DOCUMENTS

| | | |
|---|---|---|
| EP | 0169375 A2 | 1/1986 |
| EP | 0727225 A2 | 8/1996 |
| JP | 63-15974 A | 7/1988 |
| WO | WO 91/14460 A1 | 10/1991 |
| WO | WO 92/17215 A1 | 10/1992 |
| WO | WO 94/22496 A1 | 10/1994 |
| WO | WO 95/33757 A1 | 12/1995 |
| WO | WO 00/78283 A1 | 12/2000 |
| WO | WO 02/20008 A1 | 3/2002 |
| WO | WO 03/002157 A1 | 1/2003 |
| WO | WO 03/065882 A2 | 8/2003 |
| WO | WO 03/082350 A2 | 10/2003 |
| WO | WO 03/086476 A1 | 10/2003 |
| WO | WO 2004/056400 A1 | 7/2004 |
| WO | WO 2005/012319 A1 | 2/2005 |
| WO | WO 2005/079391 A2 | 9/2005 |
| WO | WO 2005/105159 A2 | 11/2005 |
| WO | WO 2007/021858 A2 | 2/2007 |
| WO | WO 2009/108376 A2 | 9/2009 |
| WO | WO 2009/110984 A2 | 9/2009 |
| WO | WO 2011/097649 A2 | 8/2011 |

OTHER PUBLICATIONS

Bergmann et al., Noninvasive quantitation of myocardial blood flow in human subjects with oxygen-15-labeled water and positron emission tomography. J Am Coll Cardiol. Sep. 1989;14(3):639-52.

Cao et al., Synthesis and antifeedant activity of new oxadiazolyl 3(2H)-pyridazinones. J Agric Food Chem. Jan. 1, 2003;51(1):152-5.

Char et al., Reductive cleavage of acetals/ketals. Synthetic Communications. 1999;29(8):1257-1261.

Clark et al., The present role of nuclear cardiology in clinical practice. Q J Nucl Med Mol Imaging. Mar. 2005;49(1):43-58.

Clark, Fluoride ion as a base in organic synthesis. Chem Rev. 1980;80(5):429-52.

Di Carli et al., Cardiac PET-CT. J Thorac Imaging. Feb. 2007;22(1):101-6.

Di Carli et al., Clinical myocardial perfusion PET/CT. J Nucl Med. May 2007;48(5):783-93.

Garcia et al., What should we expect from cardiac PET? J Nucl Med. Jun. 1993;34(6):978-80.

Garrison et al., Reaction mechanisms in the radiolysis of peptides, polypeptides, and proteins. Chem Rev. 1987;87:381-98.

Ghesani et al., Role of F-18 FDG positron emission tomography (PET) in the assessment of myocardial viability. Echocardiography. Feb. 2005;22(2):165-77.

Glover et al., Journey to find the ideal PET flow tracer for clinical use: are we there yet? J Nucl Cardiol. Nov.-Dec. 2007;14(6):765-8.

Glover et al., Comparison between 201Tl and 99mTc sestamibi uptake during adenosine-induced vasodilation as a function of coronary stenosis severity. Circulation. Feb. 1, 1995;91(3):813-20.

Glover et al., Myocardial 99mTc-tetrofosmin uptake during adenosine-induced vasodilatation with either a critical or mild coronary stenosis: comparison with 201Tl and regional myocardial blood flow. Circulation. Oct. 7, 1997;96(7):2332-8.

Glover et al., Myocardial kinetics of Tc-MIBI in canine myocardium after dipyridamole. Circulation. Feb. 1990;81(2):628-37.

Higgins et al., [3H]dihydrorotenone binding to NADH: ubiquinone reductase (complex I) of the electron transport chain: an autoradiographic study. J Neurosci. Jun. 15, 1996;16(12):3807-16.

Higuchi et al., A new 18F-labeled myocardial PET tracer: myocardial uptake after permanent and transient coronary occlusion in rats. J Nucl Med. Oct. 2008;49(10):1715-22. Epub Sep. 15, 2008.

Huang et al., Rabbit myocardial 82Rb kinetics and a compartmental model for blood flow estimation. Am J Physiol. Apr. 1989;256(4 Pt 2):H1156-64.

Huisman et al., Initial characterization of an 18F-labeled myocardial perfusion tracer. J Nucl Med. Apr. 2008;49(4):630-6. Epub Mar. 14, 2008.

Igarashi et al., Summary of toxicology studies with Pyridaben. J Peticide Sci. 1994;14 pages:Technical Information.

Kann et al., Mitochondria and neuronal activity. Am J Physiol Cell Physiol. Feb. 2007;292(2):C641-57. Epub Nov. 8, 2006.

Knapp et al., Availability of rhenium-188 from the alumina-based tungsten-188/rhenium-188 generator for preparation of rhenium-188-labeled radiopharmaceuticals for cancer treatment. Anticancer Res. May-Jun. 1997;17(3B):1783-95.

Kroemer, Mitochondria in cancer. Oncogene. Aug. 7, 2006;25(34):4630-2.

Latli et al., Photoaffinity radioligand for NADH:ubiquinone oxidoreductase: [S-C3H2](trifluoromethyl)diazirinyl-pyridaben. J Labelled Compounds Radiopharm. 1998;41(3):191-9.

Lazewatsky et al., Dosimetry of BMS747158, a novel 18F labeled tracer for myocardial perfusion imaging, in nonhuman primates at rest. J Nucl Med. 2008;49(Supplement 1):15p.

Maddahi et al., First human study of of BMS747158, a novel F-18 labeled tracer for myocardial perfusion imaging. J Nucl Med. 2008;49:70P.

Miller et al., Synthesis of 11C, 18F, 15O, and 13N radiolabels for positron emission tomography. Angew Chem Int Ed Engl. 2008;47(47):8998-9033.

Mistry et al., Toxicological evaluation of BMS-747158, a PET myocardial perfusion imaging agent. The Toxicologist. 2008;102:476.

Miyoshi, Structure-activity relationships of some complex I inhibitors. Biochim Biophys Acta. May 6, 1998;1364(2):236-44.

Nekolla et al., Assessment of imaging properties of a new F-18 labelled flow tracer in a pig model. J Am Coll Cardiol. 2008;51:A170.

Nekolla et al., Evaluation of the novel myocardial perfusion positron-emission tomography tracer 18F-BMS-747158-02: comparison to 13N-ammonia and validation with microspheres in a pig model. Circulation. May 5, 2009;119(17):2333-42. Epub Apr. 20, 2009.

Okun et al., Three classes of inhibitors share a common binding domain in mitochondrial complex I (NADH:ubiquinone oxidoreductase). J Biol Chem. Jan. 29, 1999;274(5):2625-30.

Purohit et al., Quinazoline derivatives as MC-I inhibitors: evaluation of myocardial uptake using Positron Emission Tomography in rat and non-human primate. Bioorg Med Chem Lett. Sep. 1, 2007;17(17):4882-5. Epub Jun. 14, 2007.

Purohit et al., Synthesis and biological evaluation of pyridazinone analogues as potential cardiac positron emission tomography tracers. J Med Chem. May 22, 2008;51(10):2954-70. Epub Apr. 19, 2008.

Radeke et al., Synthesis and biological evaluation of the mitochondrial complex 1 inhibitor 2-[4-(4-fluorobutyl)benzylsulfanyl]-3-methylchromene-4-one as a potential cardiac positron emission tomography tracer. J Med Chem. Sep. 6, 2007;50(18):4304-15. Epub Aug. 15, 2007.

Ravert et al., Radiosynthesis of 3-[$^{18}$F]fluoropropyl and 4-[18F]fluorobenzyl triarylphosphonium ions. J Lab Comp Radiopharm. 2004;47(8):469-76.

Ritchie et al., Guidelines for clinical use of cardiac radionuclide imaging. Report of the American College of Cardiology/American Heart Association Task Force on Assessment of Diagnostic and Therapeutic Cardiovascular Procedures (Committee on Radionuclide Imaging), developed in collaboration with the American Society of Nuclear Cardiology. J Am Coll Cardiol. Feb. 1995;25(2):521-47.

Santi et al., Toxicology of rotenone. Farmaco Sci. Apr. 1965;20:270-9.

Schelbert et al., N-13 ammonia as an indicator of myocardial blood flow. Circulation. Jun. 1981;63(6):1259-72.

Schyler, PET tracers and radiochemistry. Ann Acad Med Singapore. Mar. 2004;33(2):146-54.

Soderquist et al., Reductive cleavage of acetals and ketals with 9-borabicyclo[3.3.1]nonane†. Org Process Res Dev. 2006;10(5):1076-9.

Talpade et al., In vivo labeling of mitochondrial complex I (NADH:ubiquinone oxidoreductase) in rat brain using [(3)H]dihydrorotenone. J Neurochem. Dec. 2000;75(6):2611-21.

Ueno et al., Comparison of the inhibitory action of natural rotenone and its stereoisomers with various NADH-ubiquinone reductases. Eur J Biochem. Oct. 1, 1994;225(1):411-7.

Vanbrocklin et al., Fluorine-18 labeled dihydrorotenone analogs: preparation and evaluation of PET mitochondrial probes. Journal of Labelled Compounds and Radiopharmaceuticals,Symposium abstracts (continue in part IV). 1994; 35:217-19.

Vanbrocklin et al., Mitochondrial avid radioprobes. Preparation and evaluation of 7′(Z)-[125I]iodorotenone and 7′(Z)-[125I]iodorotenol. Nucl Med Biol. Jan. 2007;34(1):109-16. Epub Nov. 28, 2006.

Wallace, A mitochondrial paradigm of metabolic and degenerative diseases, aging, and cancer: a dawn for evolutionary medicine. Annu Rev Genet. 2005;39:359-407.

Wang et al., Insights into amyloid-beta-induced mitochondrial dysfunction in Alzheimer disease. Free Radic Biol Med. Dec. 15, 2007;43(12):1569-73. Epub Sep. 21, 2007.

Yalamanchili et al., Mechanism of uptake and retention of F-18 BMS-747158-02 in cardiomyocytes: a novel PET myocardial imaging agent. J Nucl Cardiol. Nov.-Dec. 2007;14(6):782-8. Epub Oct. 22, 2007.

Yu et al., Assessment of 18F-labeled mitochondrial complex I inhibitors as PET myocardial perfusion imaging agents in rats, rabbits, and primates. Eur J Nucl Med Mol Imaging. Jan. 2009;36(1):63-72. Epub Aug. 21, 2008.

Yu et al., The next generation of cardiac positron emission tomography imaging agents: discovery of flurpiridaz f-18 for detection of coronary disease. Seminars Nucl Med. Jul. 2011;41(4):305-13.

International Preliminary Report on Patentability for PCT/US2009/001296, mailed Sep. 10, 2010.

International Preliminary Report on Patentability for PCT/US2009/001247, mailed Sep. 10, 2010.

International Search Report and Written Opinion for PCT/US2009/001296, mailed Sep. 30, 2009.

International Search Report and Written Opinion for PCT/US2009/001247, mailed Oct. 21, 2009.

International Search Report and Written Opinion for PCT/US2010/001120, mailed Dec. 28, 2010.

Bousquet, J.-C. et al., "Gd-DOTA: Characterization of a New Paramagnetic Complex," Radiology, vol. 166, No. 3, pp. 693-698 (1988).

Brown, M. et al., "Delineation of myocardial oxygen utilization with carbon-11-labeled acetate," Circulation, vol. 76, No. 3, pp. 687-696 (1987).

Esposti, M. D., "Inhibitors of NADH—ubiquinone reductase: an overview," Biochimica et Biophysica Acta, vol. 1364, pp. 222-235 (1998).

Gout, P. W. et al., "Sulfasalazine, a potent suppressor of lymphoma growth by inhibition of the $x_c$ cystine transporter: a new action for an old drug," Leukemia, vol. 15, pp. 1633-1640 (2001).

Han, H. et al., "Total Synthesis of 34-hydroxyasimicin and Its Photoactive Derivative for Affinity Labeling of the Mitochondrial Complex I," Chemistry—A European Journal, vol. 10, No. 9, pp. 2149-2158 (2004).

Jiang, S. et al., "Mimicry of annonaceous acetogenins: Enantioselective syntheiss of a (4R)-hydroxy analogue having potent antitumor activity," J Org. Chem., vol. 67, No. 10, pp. 3404-3408 (2002).

Krivokapich, J. et al., "13N Ammonia Myocardial Imaging at Rest and With Exercise in Normal Volunteers, Quantification of Absolute Myocardial Perfusion With Dynamic Positron Emission Tomography," Circulation, vol. 80, No. 5, pp. 1328-1337 (1989).

Lindell, S. D. et al., "The design and synthesis of novel inhibitors of NADH: ubiquinone oxidoreductase," Bioorganic & Medicinal Chemistry Letters, vol. 14, pp. 511-514 (2004).

Liu. S. et al., "Integrin avb3 directed radiopharmaceuticals for tumor imaging," Drugs of the Future, vol. 28, No. 6, pp. 551-564 (2003).

Magerstadt, M. et al., "Gd(DOTA): An Alternative to Gd(DTPA) as a T1,2 Relaxation Agent for NMR Imaging of Spectroscopy," Magnetic Resonance in Medicine, vol. 3, pp. 808-812 (1986).

Marshall, R. C. et al., "Kinetic Analysis of a $^{125}$I-iodorotenone as a deposited myocardial flow tracer: Comparison with $^{99m}$Tc-sestamibi," Journal of Nuclear Medicine, vol. 42, No. 2, pp. 272-281 (2001).

Marshall, R. C. et al., "Kinetic Analysis of a $^{18}$F-fluorodihydrorotenone as a deposited myocardial flow tracer: Comparison with $^{291}$Tl," Journal of Nuclear Medicine, vol. 45, No. 11, pp. 1950-1959 (2004).

Martarello, L. et al., "Synthesis and evaluation of a new fluorine-18 labeled rotenoid as a potential pet probe of mitochondrial complex I activity," Journal of Labelled Compounds and Radiopharmaceuticals, vol. 42, No. 11, pp. 1039-1050 (1999).

Miyoshi, H. et al., "Essential structural factors of annonaceous acetogenenins as potent inhibitors of mitochondrial complex I," Biochimica et Biophysica Acta, vol. 1365, No. 3, pp. 443-452 (1998).

Nakanishi, Y. et al., "Acetogenins as selective inhibitors of the human ovarian 1A9 tumor cell line," Journal of Medicinal Chemistry, vol. 46, No. 15, pp. 3185-3188 (2003).

Nicolaou, K. C. et al., "Combinatorial synthesis of novel and potent inhibitors of NADH: ubiquinone oxidoreductase," Chemistry & Biology, vol. 7, pp. 979-992 (2000).

Pauwels, E. K. J. et al., "Fluorine-18-radiolabeled pharmaceuticals for imaging with positron emission tomography, excluding [18F]-fluorodeoxyglucose," Drugs of the Future, vol. 27, pp. 655-667 (2002).

Runge, V. M. et al., "MR Imaging of Rat Brain Glioma: Gd-DTPA versus Gd-DOTA," Radiology, vol. 166, No. 3, pp. 835-838 (1988).

Schuler, F. et al., "Functional coupling of PSST and ND1 subunits in NADH: ubiquinone oxidoreductase established by photoaffinity labeling," Biochimica et Biophysica Acta, vol. 1506, pp. 79-87 (2001).

Vanbrocklin, H. F. et al., "(F-18)fluorodihydrorotenone: Synthesis and evaluation of a mitochondrial electron transport chain (ETC) complex I probe for PET," Journal of Nuclear Medicine, vol. 35, No. 5 Suppl., p. 73P (1994).

Walker, J. E., "The NADH: ubiquinone oxidoreductase (complex I) of respiratory chains," Quarterly Review of Biophysics, vol. 25, No. 3, pp. 253-324 (1992).

Yu, M. et al., "BMS-747158-02: a novel PET myocardial perfusion imaging agent," Journal of Nuclear Cardiology, vol. 14. No. 6, pp. 789-798 (2007).

Unger, Pesticide synthesis handbook. Technology and Engineering. 1996:523-4. Google books result.

International Search Report and Written Opinion mailed Mar. 15, 2007 in connection with Application No. PCT/US2006/031231.

International Preliminary Report on Patentability mailed Feb. 21, 2008 in connection with Application No. PCT/US2006/031231.

Berman D.S., Germano.G, Slomka, P.J., (2012). Improvement in PET myocardial perfusion image quality and quantification with Flurpiridaz F 18. Journal of Nuclear Cardiology 19(1): S38-45.

Berman et al., (2010) Comparison of 18F-BMS747158 and 82Rb PET vs SPECT for detection of myocardial ischemia. Journal of Nuclear Cardiology 17(4): 743. Abstract #31.17.

Case J.A, Lazewatsky. J., Hsu B-L., Maddahi J., Berman D., Bateman T, (2010). Automatic registration of F-18 labeled BMS-747158 stress and rest myocardial perfusion images using 6D cross-correlation optimization. Journal of Nuclear Medicine 51(Supplement 2): 1687.

Case J.A, Lazewatsky. J., Hsu, BL, Maddahi J, Berman DS, Bateman TM, (2010). Iterative technique for optimizing injected tracer dosage and acquisition time for F-18 labeled myocardial perfusion tracer Flurpiridaz F-18. Journal of Nuclear Cardiology 17(4): 726. Abstract # 9.17.

Case JA, Lazewatsky JL, Cullom SJ, Berman DS, Maddahi J, Bateman TM, (2011). Impact of image filtering, BMI, and gender on optimal dosage acquisition time product using a novel PET myocardial perfusion tracer: F-18 labeled Flurpiridaz. Journal of Nuclear Cardiology 18(4): 769-770. Asbtract #14.32.

Case JA., TM Bateman, M Luangamath, JL Lazewatsky, DS Berman, J Maddahi., (2010). Independence of myocardial functional parameters (LVEF, EDV, and ESV) across a large range of acquisition times and measured from a novel F-18 radiotracer, Flurpiridaz F-18. Journal of Nuclear Cardiology 17(4 Supplement 1): 725-726. Abstract #9.15.

Case, JA; Maddahi, J; Bengel, FM; Bateman, T; Dahlbom, M; Lazewatsky, J., (2009) Imaging properties of F-18 labeled myocardial perfusion PET agent, BMS747158: dosage, acquisition time and scanner type. Journal of Nuclear Medicine 50 (Supplement 2): 418. 2 pages.

Crane P., Hayes, M. Cesati R, Spencer K., Sanga M, Robinson S, Onthank D., (2011) Use of a tritiated ($^3$H) analog of flurpiridaz F18 to characterize the pharmacokinetics, metabolism and excretion in normal human subjects. AAAPS. (2011) Abstract.

Higuchi T; Huisman M.C., Nekolla S.G.; Wester H.J.; Poethko T; Schwaiger M; Casebier D.C., A Novel [F-18] labeled PET Tracer for the Characterization of Coronary Artery Disease: Preliminary Evaluation in a Coronary Occlusion Rat Model Circulation. 2007;116:II_658 Abstract #2947.

Hsu B, Logan J, Quirke A, Orlando L, Devine M, Dann R, Taillefer R, Lazewatsky J., (2011) Remote camera qualification (RCQ) of PET and PET/CT scanners for BMS747158 F18 myocardial perfusion phase 3 clinical trial using a standardized phantom procedure. J Nucl Med. 52 (Supplement 1):54.

Hsu B., Lazewatsky. J., Bateman T., Devine M., Maddahi J., Berman D. et al., (2010). Cardiac phantom simulation of dose injection parameters for one-day rest/stress myocardial perfusion tracer. Journal of Nuclear Medicine 51(Supplement 2): 320.

Huang S, Dahlbom M, Truong D, Lazewatsky JC, Washburn D, Schelbert H, Czernin J, Phelps M, Maddahi J, (2011). Evaluation of absolute mbf at rest and stress with Flurpiridaz F-18 injection PET in normal subjects and patients with coronary artery disease (CAD) and in two types of scanners. Journal of Nuclear Cardiology 18(4): 783-784. Abstract #26.19.

Huang S-C, Dahlbom M, Maddahi J, Truong D, Lazewatsky J, Washburn D, Schelbert H, Czernin J, Phelps M., (2011) Streamlined quantification of absolute MBF at rest and stress with flurpiridaz F-18 injection PET in normal subjects and patients with coronary artery disease (CAD). J Nucl Med. 52 (Supplement 1):1114.

Huisman M.; Higuchi T; Reder S; Nekolla S; Poethko T; Casebier D; Schwaiger M, First Preclinical Study of a New F-18 Labeled PET Tracer for Myocardial Perfusion Imaging Circulation. 2007;116:II_718 Abstract # 3193.

Kagan, M. Bozek J., Spencer, K., Hsu B., Mistry M., Onthank D., Robinson S., Yu M., Comparison of flurpiridaz F 18 and FDG for assessment of left ventricular tissue mass following myocardial infarction in rats. Journal of Nuclear Medicine;2011:52( Supp. 1):1097.

Lazewatsky J, Case J, Maddahi J, Berman D, Slomka P, O'Loughlin L, Quirke A, Washburn D., (2011) Relative defect radioactivity and perceived defect severity are proportional with flurpiridaz F18 PET myocardial perfusion imaging. J Nucl Med. 52 (Supplement 1):1115.

Lazewatsky J., M. J., Berman D., Bhat G., Sinha S., Devine M., (2010) Development of a method for the determination of dose ratio and minimum inter-injection interval for a one-day rest-stress protocol with BMS747158 PET myocardial perfusion agent. Journal of Nuclear Medicine 51(Supplement 2):600.

Maddahi J, Berman D, Taillefer R, Udelson R, Devine M, Lazewatsky J, Bhat G and Washburn D., (2011) Phase 2 clinical comparison of flurpiridaz F 18 injection PET and SPECT myocardial perfusion imaging for diagnosis of coronary artery disease. J Nucl Med. 52 (Supplement 1):59.

Maddahi J, Berman D.S., Taillefer R., Udelson J., Devine M, Lazewatsky J., Bhat G, Washburn D.,(2011) Phase 2 safety and clinical comparison of flurpiridaz F18 injection PET and SPECT myocardial perfusion imaging for diagnosis of coronary artery disease. European Heart Journal Supplements ;13( Supplement A ): A45. Abstract # 197.

Maddahi J., (2012). Properties of an ideal PET perfusion tracer: New PET tracer cases and data. Journal of Nuclear Cardiology. 19(Supplement 1): S30-37.

Maddahi J., B. F., Huang H., Czernin J., Schelbert H., Zhu Q., Lazewatsky J., Case, JA., Sparks R., Phelps ME.,, J. Czernin, et al., (2011). Phase I, First-in-Human Study of BMS747158, a Novel 18F-Labeled Tracer for Myocardial Perfusion PET: Dosimetry, Biodistribution, Safety, and Imaging Characteristics After a Single Injection at Rest. J Nucl Med 52: 1-9.

Maddahi J., C. J., Ehlgen A., Lazewatsky J., Zhi Q., Phelps M., (2010). Comparison of F-18 labeled BMS747158 PET and Tc-99m labeled spect myocardial perfusion imaging for detection and evaluation of coronary artery disease. Journal of the American College of Cardiology 55(10A): E616.

Maddahi J., Czernin J, Berman D, Taillefer R, Devine M, Lazewatsky J, Bhat G and Washburn D., (2011) Comparison of flurpiridaz F 18 PET injection and Tc-99m labeled SPECT myocardial perfusion imaging for identifying severity and extent of stress induced myocardial ischemia in phase 2 clinical trials. J Nucl Med. 52 (Supplement 1):444.

Maddahi J., Huang. S., Truong D., Lazewatsky JL, Ehlgen A., Schelbert H., Dzernin J, Phelps M (2010). Preliminary results of absolute quantification of rest and stress myocardial blood flow with Flurpridaz F-18 PET in normal and coronary artery disease patients in a single-center study. Journal of Nuclear Cardiology 17(4): 743. Abstract # 31.18.

Maddahi J., L. M., Czernin C., Ehgen A., Lazewatsky J., Devine M., (2010) F-18 labeled BMS747158 PET myocardial perfusion imaging identifies more severe and extensive stress induced myocardial ischemia than Tc-99m Sestamibi SPECT. Journal of Nuclear Medicine 51(Supplement 2): 1739.

Maddahi, J; Bengel, F; Huang, H; Czernin, J; Schelbert, H; Zhu, Q; Lazewatsky, J; Case, JA; Sparks, R; Phelps, ME., Phase 1 Human safety, dosimetry, Biodistribution and rest/stress myocardial imaging characteristics of F18 Labeled BMS 747158. (2009) Journal of the American College of Cardiology 53(10): A297. Abstract #1054-263.

Maddahi, J; Huang, H, Schiepers, C; Schelbert, H; Wijatyk, A; Lazewatsky, J; Zhu, Q; Phelps, M., (2009) Protocols for same day rest-stress PET imaging with the new F-18 labeled BMS747158 myocardial perfusion tracer. European Heart Journal;11(Supp B): S89. Abstract #433.

Maddahi, J; Huang, H; Czernin, J; Schelbert, H; Bengel, F; Wijatyk, A; Lazewatsky, J; Zhu, Q., (2009) Human safety, dosimetry, biodistribution, and rest-stress myocardial imaging characteristics of the new F-18 labeled BMS747158 myocardial perfusion PET tracer. European Heart Journal 11(Supplement): S89. Abstract #432.

Maddahi, J; Huang, S; Schiepers, C; Bengel, F; Czernin, J; Schelbert, H; Lazewatsky, J; Zhu, Q; Phelps, ME., (2009) Same day rest-stress protocols for PET imaging with the new F-18 labeled BMS747158 myocardial perfusion tracer. Journal of Nuclear Medicine 50(Supplement 2): 1173.

Mou et al., Preparation and biodistribution of [18F]FP2OP as myocardial perfusion imaging agent for positron emission tomography. Bioorg Med Chem. Feb. 2010;18(3):1312-20. Epub Dec. 26, 2009.

Nekolla S, Sibylle R, Higuchi T, Saraste A, Yu M, Robinson S, Casebier D and Schwaiger M., Evaluation of a new myocardial PET tracer 18F-BMS-747158-02 (18F-BMS): Comparison to 13N ammonia and validation with microspheres. J Nucl Med. 2008; 49 (Supplement 1):29P.

Nekolla S.G., Saraste A.., (2011). Novel F-18 Labeled PET Myocardial Perfusion Tracers: Bench to Bedside. Current Cardiology Reports 13: 145-150.

Sherif H, N. S., Saraste A., Reder S., Yu M., Robinson S, Schwaiger M, (2011). Simplified quantification of myocardial flow reserve with flurpiridaz F-18: Validation with Microspheres in a pig model. Journal of Nuclear Medicine 52: 617-624.

Sherif H, Saraste A, Higuchi T, Reder S, Weidl E, Poethko T, Weber A, Robinson S, Nekolla S, and Schwaiger M. Evaluation of the novel PET perfusion tracer 18F BMS747158-02 for measurement of myocardial infarct size in a rat model. J Nucl Med. 2008; 49 (Supplement 1):186P.

Sherif H. Nekolla SC. Schwaiger M, (2011). Reply: Simplified Quantification of Myocardial Flow Reserve with 18F-Flurpiridaz: Validation with Microspheres in a Pig Model. Journal of Nuclear Medicine 52(11): 1835-1836.

Sherif HM, Saraste A, Weidl E, Weber AW, Higuchi T, Reder S, Poethko T, Henriksen G, Casebier D, Robinson S, Wester HJ, Nekolla SG, Schwaiger M, Evaluation of a novel (18)F-labeled positron-emission tomography perfusion tracer for the assessment of myocardial infarct size in rats. Circulation: Cardiovascular Imaging. Mar. 2009;2(2):77-84.

Slomka PJ, M. J. L. M. L., Lazewatsky JL, Germano G., Berman DS, (2010) Multicenter development of normal perfusion and function limits for stress and rest flurpiridaz F-18 Cardiac PET. Journal of Nuclear Cardiology 17(4): 725. Abstract #9.14.

Tamarappoo B.K, N. R., Hayes S.W, Thomson L.E.J, Friedman J.D, Cheng V.Y, Slomka P.J, Kim J., Gransar H., Germano G., Ehlgen A., Berman D.S, (2010) Comparison of myocardial stress perfusion defect assessment using 99mTc Sestamibi SPECT vs 18F-BMS747158 PET. Journal of Nuclear Cardiology 17(4): 742. Abstract #31.14.

Woo J, Tamarappoo B, Dey D, Nakazato R, Le Meunier L, Ramesh A, Lazewatsky J, Germano G, Berman DS, Slomka PJ., (2011). Automatic 3D registration of dynamic stress and rest (82)Rb and flurpiridaz F 18 myocardial perfusion PET data for patient motion detection and correction. Medical Physics 38(11): 6313-26.

Yu et al., Evaluation of LMI1195, a Novel 18F-Labeled Cardiac Neuronal PET Imaging Agent, in Cells and Animal Models. Circulation: Cardiovascular Imaging 2011 4: 435-443.

Yu M, Guaraldi M, Kagan M, Azure M. and Robinson R., Cardiac imaging and uptake of BMS747158-02 under various experimental conditions. J Nucl Med. 2008; 49 (Supplement 1):187P.

Yu M, Guaraldi M, Kagan M, McDonald J., Hayes M., Yalamanchili P, Mistry M, Radeke H, Azure M, Casebier D, Robinson S,., Myocardial Perfusion Imaging with 18F-Chromone Based MC-1 Inhibitors. Molecular Imaging. 2006;5(3):372-3. Abstract ID: 642 Poster board space:105.

Yu M, Mistry M, Guaraldi M, Kagan M, McDonald J., Drew K, Hayes M, Yalamanchili P, Purohit A, Radeke H, Azure M, Hanson K, Robinson S, Casebier D., [18F]-RP1012: A Novel Myocardial Perfusion Imaging Agent for use with positron emission tomography (PET). Circulation Supplmement 2, 112(17), II-761, Abstract #3546, 2005.

Yu M, Yalamanchili P., Purohit A, Radeke H, Azure M, Mistry M, , Hayes M, Hanson K, Guaraldi M, Drew K, McDonald J, Wexler E, Su F., Benetti R, Casebier D, Robinson S., In-vivo Assessment of Mitochondrial Complex-1 Inhibitors as Myocardial Perfusion Imaging Agents (MPIA). Circulation Supplement 2, 112 (17), II-474, Abstract #2283, 2005.

Yu M, Bozek J, Guaraldi M, Kagan M, Azure M, Robinson SP., Cardiac imaging and safety evaluation of BMS747158, a novel PET myocardial perfusion imaging agent, in chronic myocardial compromised rabbits. J Nuclear Cardiology. 2010;17(4):631-6.

Yu M, Guaraldi M.T, Bozek J, Kagan M, Azure M, Radeke Cdebaca M.H, Robinson S.P., Effects of Food Intake and Anesthetic on Cardiac Imaging and Uptake of BMS-747158-02 in Comparison with FDG. Journal Nuclear Cardiology. Sep.-Oct. 2009;16(5):763-8.

Yu M, Robinson S.P. A novel cardiac PET imaging agent. International Hospital Equipment and Solutions. 2009; 35(4):14-5.

International Preliminary Report on Patentablitiy for PCT/US2010/001120, mailed Oct. 27, 2011.

International Search Report and Written Opinion for PCT/US2011/024109, mailed Oct. 24, 2011.

CONTRAST AGENTS FOR MYOCARDIAL PERFUSION IMAGING

CROSS REFERENCE TO RELATED APPLICATION

This application is a divisional application of U.S. application Ser. No. 11/055,498 filed Feb. 10, 2005 now U.S. Pat. No. 7,344,702 which claims the benefit of priority under 35 U.S.C. §119(e) from the provisional application 60/544,861 filed Feb. 13, 2004, the contents of which are herein incorporated by reference.

The present disclosure relates to novel compounds comprising imaging moieties, and their use for diagnosing certain disorders in a patient.

Mitochondria are membrane-enclosed organelles distributed through the cytosol of most eukaryotic cells. Mitochondria are especially concentrated in myocardium tissue.

Complex 1 ("MC-1") is a membrane-bound protein complex of 46 dissimilar subunits. This enzyme complex is one of three energy-transducing complexes that constitute the respiratory chain in mammalian mitochondria. This NADH-ubiquinone oxidoreductase is the point of entry for the majority of electrons that traverse the respiratory chain, eventually resulting in the reduction of oxygen to water (*Q. Rev. Biophys.* 1992, 25, 253-324).

Known inhibitors of MC-1 include deguelin, piericidin A, ubicidin-3, rolliniastatin-1, rolliniastatin-2 (bullatacin), capsaicin, pyridaben, fenpyroximate, amytal, MPP+, quinolines, and quinolones (*BBA* 1998, 1364, 222-235).

The present disclosure is based, in part, on the recognition that interrupting the normal function of mitochondria could advantageously concentrate certain compounds in the mitochondria, and hence in the mitochondria-rich myocardium tissue. If these compounds were labeled with an imaging moiety, such a build up could be detected, thereby providing valuable diagnostic markers for myocardial perfusion imaging. For purposes of this specification, a compound is referred to as "labeled" when an imaging moiety is attached to the compound.

In one embodiment the present disclosure provides a method of imaging myocardial perfusion comprising administering to a patient a contrast agent which comprises an imaging moiety and a compound selected from deguelin, pyridaben, pyridimifen, tebufenpyrad, fenazaquin, a deguelin analog, a pyridaben analog, a pyridimifen analog, a tebufenpyrad analog, and an fenazaquin analog; and scanning the patient using diagnostic imaging. In another embodiment the imaging moiety is a radioisotope for nuclear medicine imaging, a paramagnetic species for use in MRI imaging, an echogenic entity for use in ultrasound imaging, a fluorescent entity for use in fluorescence imaging, or a light-active entity for use in optical imaging.

In another embodiment the present disclosure provides a contrast agent comprising an imaging moiety and a compound selected from deguelin, pyridaben, pyridimifen, tebufenpyrad, fenazaquin a deguelin analog, a pyridaben analog, a pyridimifen analog, a tebufenpyrad analog, and an fenazaquin analog. In another embodiment the imaging moiety is a radioisotope for nuclear medicine imaging, a paramagnetic species for use in MRI imaging, an echogenic entity for use in ultrasound imaging, a fluorescent entity for use in fluorescence imaging, or a light-active entity for use in optical imaging.

In another embodiment the paramagnetic species for use in MRI imaging is $Gd^{3+}$, $Fe^{3+}$, $In^{3+}$, or $Mn^{2+}$.

In another embodiment the echogenic entity for use in ultrasound imaging is a fluorocarbon encapsulated surfactant microsphere.

In another embodiment the radioisotope for nuclear medicine imaging is $^{11}c$, $^{13}N$, $^{18}F$, $^{123}I$, $^{125}I$, $^{99m}Tc$, $^{95}Tc$, $^{111}In$, $^{62}Cu$, $^{64}CU$, $^{67}Ga$, or $^{68}Ga$. In another embodiment the imaging moiety is $^{18}F$. In another embodiment the imaging moiety is $^{99m}Tc$.

In another embodiment the present disclosure provides a contrast agent comprising an imaging moiety and a compound selected from deguelin, pyridaben, pyridimifen, tebufenpyrad, fenazaquin a deguelin analog, a pyridaben analog, a pyridimifen analog, a tebufenpyrad analog, and an fenazaquin analog wherein the contrast agent is of formula (I)

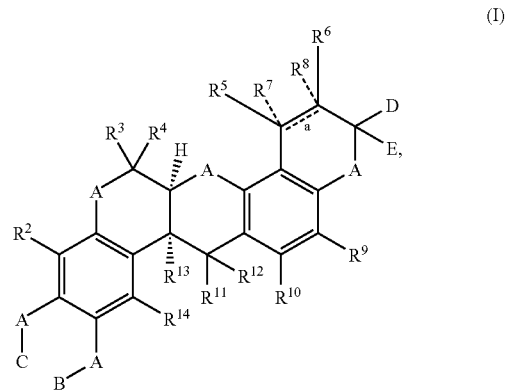

(I)

wherein each A is independently selected from O, $CHR^1$, S, and $NR^1$;

B is selected from hydrogen, $C_1$-$C_6$ alkyl optionally substituted with an imaging moiety, and an imaging moiety;

C is selected from hydrogen, $C_1$-$C_6$ alkyl optionally substituted with an imaging moiety, an imaging moiety, and a bond to B;

D is selected from hydrogen, $C_1$-$C_6$ alkyl optionally substituted with an imaging moiety, and an imaging moiety;

E is selected from hydrogen, $C_1$-$C_{60}$ alkyl optionally substituted with an imaging moiety, and an imaging moiety; or E and D, together with the carbon atom to which they are attached, form a double bond; or E and D, together with the carbon atom to which they are attached, form a cyclopropyl ring;

$\overline{\overline{a}}$ is a single or a double bond;

$R^1$, $R^2$, $R^3$, $R^4$, $R^9$, $R^{10}$, $R^{13}$, and $R^{14}$, are each independently selected from hydrogen, $C_1$-$C_6$ alkyl optionally substituted with an imaging moiety, and an imaging moiety;

$R^5$ and $R^6$ are each independently selected from hydrogen, $C_1$-$C_6$ alkyl optionally substituted with an imaging moiety, halo, hydroxy, and an imaging moiety;

when present, $R^7$ and $R^{80}$ are independently selected from hydrogen, $C_1$-$C_6$ alkyl optionally substituted with an imaging moiety, halo, hydroxy, and an imaging moiety; or $R^5$ and $R^7$ together form an oxo group; or $R^6$ and $R^8$ together form an oxo group; or $R^7$ is O and $R^8$ is a bond to $R^7$;

provided that when $\overline{\overline{a}}$ is a double bond, $R^7$ and $R^8$ are absent;

$R^{11}$ is hydrogen or hydroxy;

$R^{12}$ is selected from hydrogen, $C_1$-$C_6$ alkyl optionally substituted with an imaging moiety, and an imaging moiety; or $R^{11}$ and $R^{12}$ together form an oxo group or =$CHR^1$;

with the proviso that at least one imaging moiety is present in formula (I).

In another embodiment

A is O;

B and C are each independently $CH_3$ or $CH_2{}^{18}F$;

D and E are each independently $CH_3$ or $CH_2{}^{18}F$;

$R^5$, $R^6$, $R^9$, and $R^{10}$ are each independently hydrogen or $^{18}F$; and $R^{11}$ and $R^{12}$ together form an oxo group.

In another embodiment the contrast agent is selected from

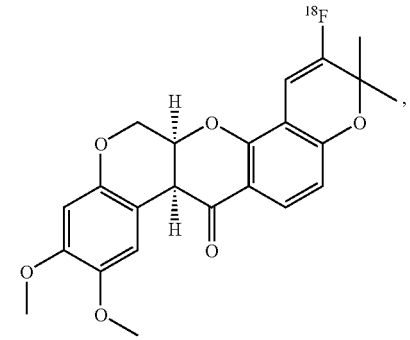

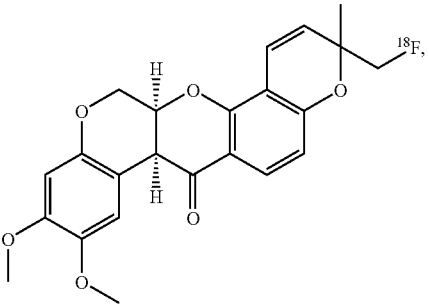

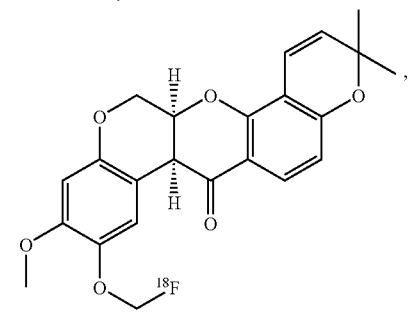

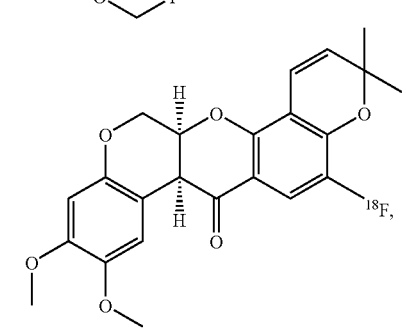

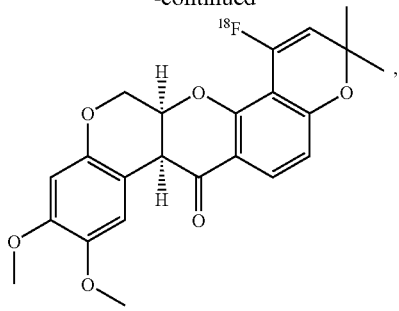

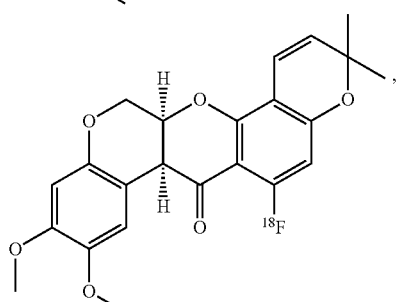

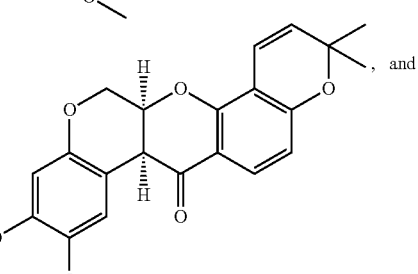

, and

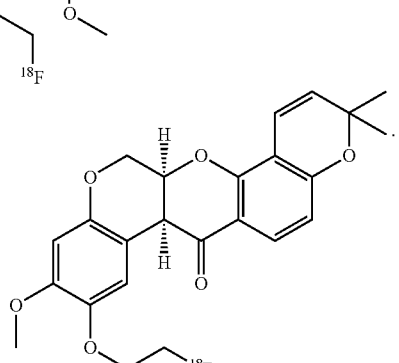

In another embodiment the present disclosure provides a contrast agent comprising an imaging moiety and a compound selected from deguelin, pyridaben, pyridimifen, tebufenpyrad, fenazaquin a deguelin analog, a pyridaben analog, a pyridimifen analog, a tebufenpyrad analog, and an fenazaquin analog wherein the contrast agent is of formula (II),

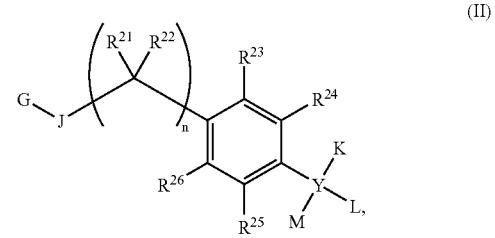

(II)

wherein

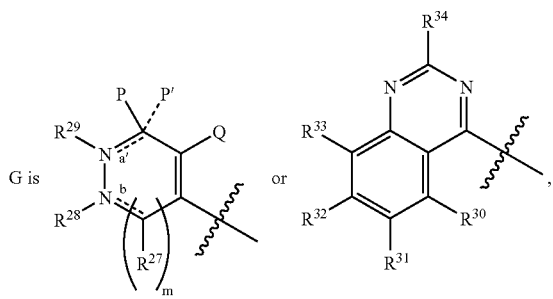

wherein m is 0 or 1;

--a'-- and --b-- each independently represent a single or a double bond;

$R^{27}$, $R^{30}$, $R^{31}$, $R^{32}$, $R^{33}$, and $R^{34}$ are independently selected from hydrogen, $C_1$-$C_6$ alkyl optionally substituted with an imaging moiety, and an imaging moiety;

when present, $R^{28}$ is selected from hydrogen and $C_1$-$C_6$ alkyl optionally substituted with an imaging moiety, provided that when --b-- is a double bond, $R^{28}$ is absent;

when present, $R^{29}$ is $C_1$-$C_6$ alkyl optionally substituted with an imaging moiety, provided that when --a'-- is a double bond, $R^{29}$ is absent;

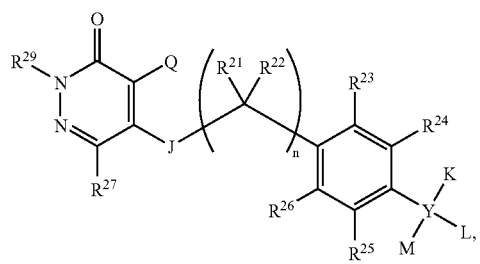

wherein $R^{35}$, $R^{36}$, $R^{37}$, $R^{38}$, and $R^{39}$ are independently selected from hydrogen, $C_1$-$C_6$ alkyl optionally substituted with an imaging moiety, and an imaging moiety;

when present, P' is hydrogen; or

P and P' together form an oxo group;

provided that when --a'-- is a double bond, P' is absent;

Q is halo or haloalkyl;

J is selected from N($R^{27}$), S, O, C(=O), C(=O)O, NHCH$_2$CH$_2$O, a bond, and C(=O)N($R^{27}$), with each group being drawn with its left end attached to G and its right end attached to the carbon substituted with $R^{21}$ and $R^{22}$;

when present, K is selected from hydrogen, alkoxyalkyl, alkyloxy, aryl, $C_1$-$C_6$ alkyl optionally substituted with an imaging moiety, heteroaryl, and an imaging moiety;

when present, L is selected from hydrogen, alkoxyalkyl, alkyloxy, aryl, $C_1$-$C_6$ alkyl optionally substituted with an imaging moiety, heteroaryl, and an imaging moiety;

M is selected from hydrogen, alkoxyalkyl, alkyloxy, aryl, $C_1$-$C_6$ alkyl optionally substituted with an imaging moiety, heteroaryl, and an imaging moiety; or L and M, together with the atom to which they are attached, form a three- or four-membered carbocyclic ring;

n is 0, 1, 2, or 3;

$R^{21}$, $R^{22}$, $R^{23}$, $R^{24}$, $R^{25}$, and $R^{26}$ are independently selected from hydrogen, $C_1$-$C_6$ alkyl optionally substituted with an imaging moiety, and an imaging moiety; and Y is selected from a bond, carbon, and oxygen; provided that when Y is a bond, K and L are absent and M is selected from aryl and heteroaryl; and provided that when Y is oxygen, K and L are absent and M is selected from hydrogen, alkoxyalkyl, aryl, $C_1$-$C_6$ alkyl optionally substituted with an imaging moiety, and heteroaryl;

provided that at least one imaging moiety is present in formula (II).

In another embodiment $R^{29}$ is $C_1$-$C_6$ alkyl wherein the $C_1$-$C_6$ alkyl is tert-butyl.

In another embodiment $R^{28}$ is $C_1$-$C_6$ alkyl wherein the $C_1$-$C_6$ alkyl is methyl.

In another embodiment the present disclosure provides a contrast agent comprising an imaging moiety and a compound selected from deguelin, pyridaben, pyridimifen, tebufenpyrad, fenazaquin a deguelin analog, a pyridaben analog, a pyridimifen analog, a tebufenpyrad analog, and an fenazaquin analog wherein the contrast agent is of formula (III)

(III)

wherein:

J is selected from N($R^{27}$), S, O, C(=O), C(=O)O, NHCH$_2$CH$_2$O, a bond, or C(=O)N($R^{27}$), with each group being drawn with its left end attached to G and its right end attached to the carbon substituted with $R^{21}$ and $R^{22}$;

when present, K is selected from hydrogen, alkoxyalkyl, alkyloxy, aryl, $C_1$-$C_6$ alkyl optionally substituted with an imaging moiety, heteroaryl, and an imaging moiety;

when present, L is selected from hydrogen, alkoxyalkyl, alkyloxy, aryl, $C_1$-$C_6$ alkyl optionally substituted with an imaging moiety, heteroaryl, and an imaging moiety;

M is selected from hydrogen, alkoxyalkyl, alkyloxy, aryl, $C_1$-$C_6$ alkyl optionally substituted with an imaging moiety, heteroaryl, and an imaging moiety; or L and M, together with the atom to which they are attached, form a three- or four-membered carbocyclic ring;

Q is halo or haloalkyl;

n is 0, 1, 2, or 3;

$R^{21}$, $R^{22}$, $R^{23}$, $R^{24}$, $R^{25}$, $R^{26}$, and $R^{27}$ are independently selected from hydrogen, $C_1$-$C_6$ alkyl optionally substituted with an imaging moiety, and an imaging moiety;

$R^{29}$ is $C_1$-$C_6$ alkyl optionally substituted with an imaging moiety; and Y is selected from a bond, carbon, and oxygen; provided that when Y is a bond, K and L are absent and M is selected from aryl and heteroaryl; and provided that when Y is oxygen, K and L are absent and M is selected from hydrogen, alkoxyalkyl, arc, $C_1$-$C_6$ alkyl optionally substituted with an imaging moiety, and heteroaryl;

provided that at least one imaging moiety is present in formula (III).

In another embodiment J is O and $R^{29}$ is $C_1$-$C_6$ alkyl wherein the $C_1$-$C_6$ alkyl is tert-butyl, In another embodiment the contrast agent is selected from

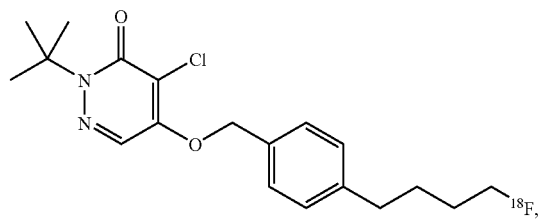

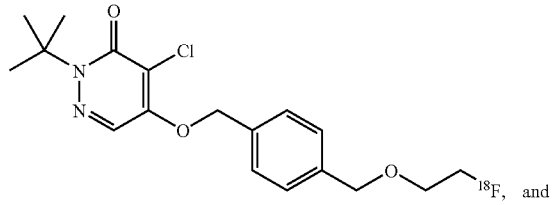

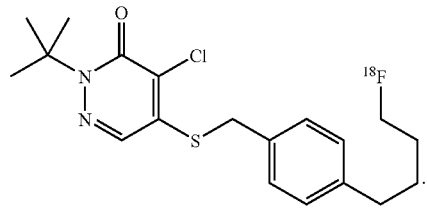

In another embodiment the present disclosure provides a contrast agent comprising an imaging moiety and a compound selected from deguelin, pyridaben, pyridimifen, tebufenpyrad, fenazaquin a deguelin analog, a pyridaben analog, a pyridimifen analog, a tebufenpyrad analog, and an fenazaquin analog wherein the contrast agent is of formula (IV):

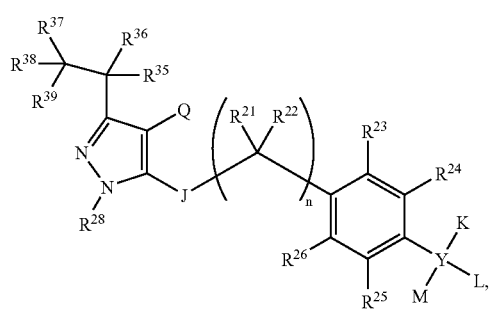

wherein:

J is selected from $N(R^{27})$, S, O, $C(=O)$, $C(=O)O$, $NHCH_2CH_2O$, a bond, and $C(=O)N(R^{27})$, with each group being drawn with its left end attached to G and its right end attached to the carbon substituted with $R^{21}$ and $R^{22}$;

when present, K is selected from hydrogen, alkoxyalkyl, alkyloxy, aryl, $C_1$-$C_6$ alkyl optionally substituted with an imaging moiety, heteroaryl, and an imaging moiety;

L is selected from hydrogen, alkoxyalkyl, alkyloxy, aryl, $C_1$-$C_6$ alkyl optionally substituted with an imaging moiety, heteroaryl, and an imaging moiety;

M is selected from hydrogen, alkoxyalkyl, alkyloxy, aryl, $C_1$-$C_6$ alkyl optionally substituted with an imaging moiety, heteroaryl, and an imaging moiety; or L and M, together with the atom to which they are attached, form a threes or four-membered carbocyclic ring;

Q is halo or haloalkyl;

n is 0, 1, 2, or 3;

$R^{21}$, $R^{22}$, $R^{23}$, $R^{24}$, $R^{25}$, $R^{26}$, $R^{27}$, $R^{28}$, $R^{35}$, $R^{36}$, $R^{37}$, $R^{38}$, and $R^{39}$ are independently selected from hydrogen, $C_1$-$C_6$ alkyl optionally substituted with an imaging moiety, and an imaging moiety; and Y is selected from a bond, carbon, and oxygen, provided that when Y is a bond, K and L are absent and M is selected from aryl and heteroaryl; and provided that when Y is oxygen, K and L are absent and M is selected from hydrogen, alkoxyalkyl, aryl, $C_1$-$C_6$ alkyl optionally substituted with an imaging moiety, and heteroaryl;

provided that at least one imaging moiety is present in formula (IV).

In another embodiment J is $C(=O)N(H)$, and $R^{28}$ is $C_1$-$C_6$ alkyl wherein the $C_1$-$C_6$ alkyl is methyl.

In another embodiment the contrast agent is selected from

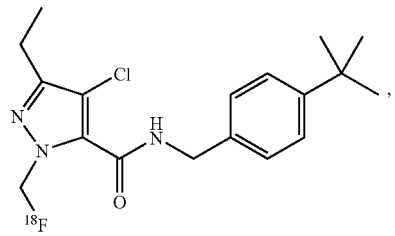

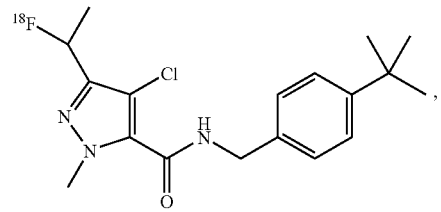

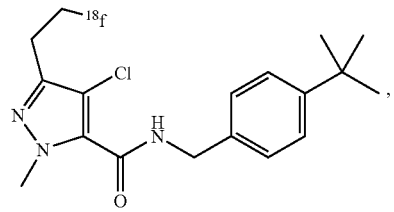

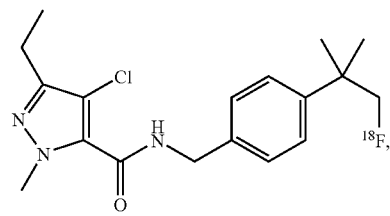

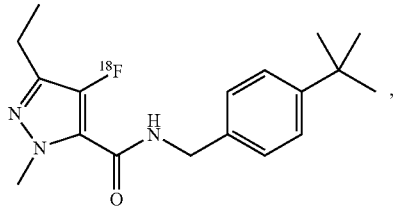

-continued

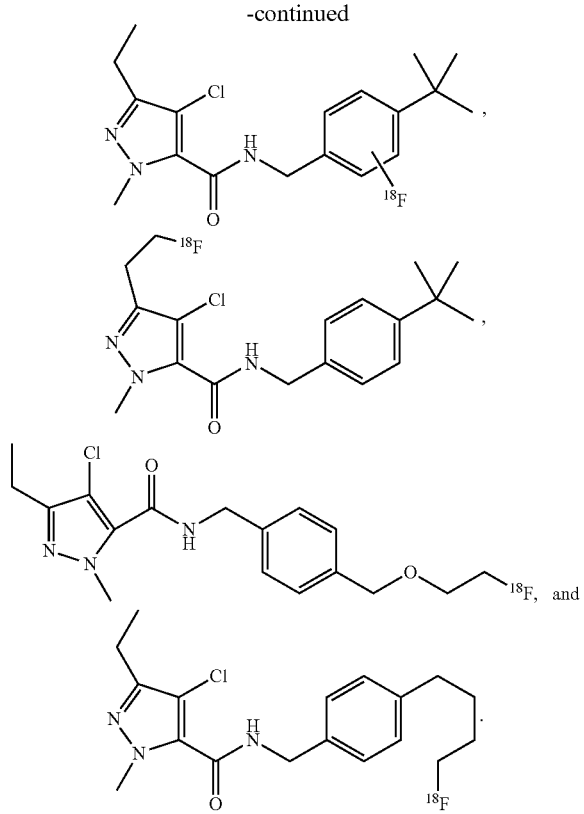

In another embodiment the present disclosure provides a contrast agent comprising an imaging moiety and a compound selected from deguelin, pyridaben, pyridimifen, tebufenpyrad, fenazaquin a deguelin analog, a pyridaben analog, a pyridimifen analog, a tebufenpyrad analog, and an fenazaquin analog wherein the contrast agent is of formula (V)

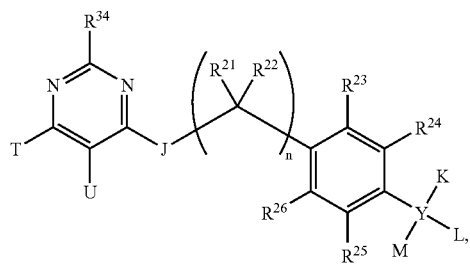

wherein

J is selected from $N(R^{27})$, S, O, C(=O), C(=O)O, $NHCH_2CH_2O$, a bond, and $C(=O)N(R^{27})$;

K is selected from hydrogen, alkoxyalkyl, alkyloxy, aryl, $C_1$-$C_6$ alkyl optionally substituted with an imaging moiety, heteroaryl, and an imaging moiety;

when present, L is selected from hydrogen, alkoxyalkyl, alkyloxy, aryl, $C_1$-$C_6$ alkyl optionally substituted with an imaging moiety, heteroaryl, and an imaging moiety;

when present, M is selected from hydrogen, alkoxyalkyl, alkyloxy, aryl, $C_1$-$C_6$ alkyl optionally substituted with an imaging moiety, heteroaryl, and an imaging moiety; or L and M, together with the atom to which they are attached, form a three- or four-membered carbocyclic ring;

T and U are independently selected from hydrogen, alkoxy, alkoxyalkyl, $C_1$-$C_6$ alkyl optionally substituted with an imaging moiety, halo, and an imaging moiety; or T and U, together with the carbon atoms to which they are attached, form a five- to six-membered aromatic or non-aromatic ring containing zero to two heterotoms selected from oxygen, nitrogen, and sulfur; wherein said ring is optionally substituted with one, two, or three substituents independently selected from $C_1$-$C_6$ alkyl optionally substituted with an imaging moiety and an imaging moiety;

n is 0, 1, 2, or 3; and $R^{21}$, $R^{22}$, $R^{23}$, $R^{24}$, $R^{25}$, $R^{26}$, $R^{27}$, and $R^{34}$ are independently selected from hydrogen, $C_1$-$C_6$ alkyl optionally substituted with an imaging moiety, and an imaging moiety;

Y is selected from a bond, carbon, and oxygen, provided that when Y is a bond, K and L are absent and M is selected from aryl and heteroaryl; and provided that when Y is oxygen, K and L are absent and M is selected from hydrogen, alkoxyalkyl, aryl, $C_1$-$C_6$ alkyl optionally substituted with an imaging moiety, and heteroaryl;

provided at least one imaging moiety is present in formula (V).

In another embodiment J is O.

In another embodiment the present disclosure provides a contrast agent comprising an imaging moiety and a compound selected from deguelin, pyridaben, pyridimifen, tebufenpyrad, fenazaquin a deguelin analog, a pyridaben analog, a pyridimifen analog, a tebufenpyrad analog, and an fenazaquin analog wherein the contrast agent is of formula (VI)

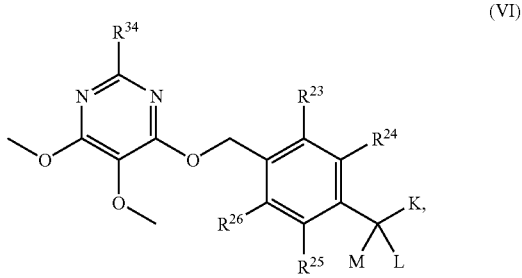

wherein $R^{23}$, $R^{24}$, $R^{25}$, $R^{26}$, and $R^{34}$ are independently selected from hydrogen, $C_1$-$C_6$ alkyl optionally substituted with an imaging moiety, and an imaging moiety;

provided that at least one imaging moiety is present in formula (VI).

In another embodiment the contrast agent is selected from

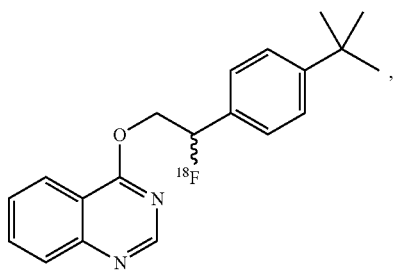

-continued

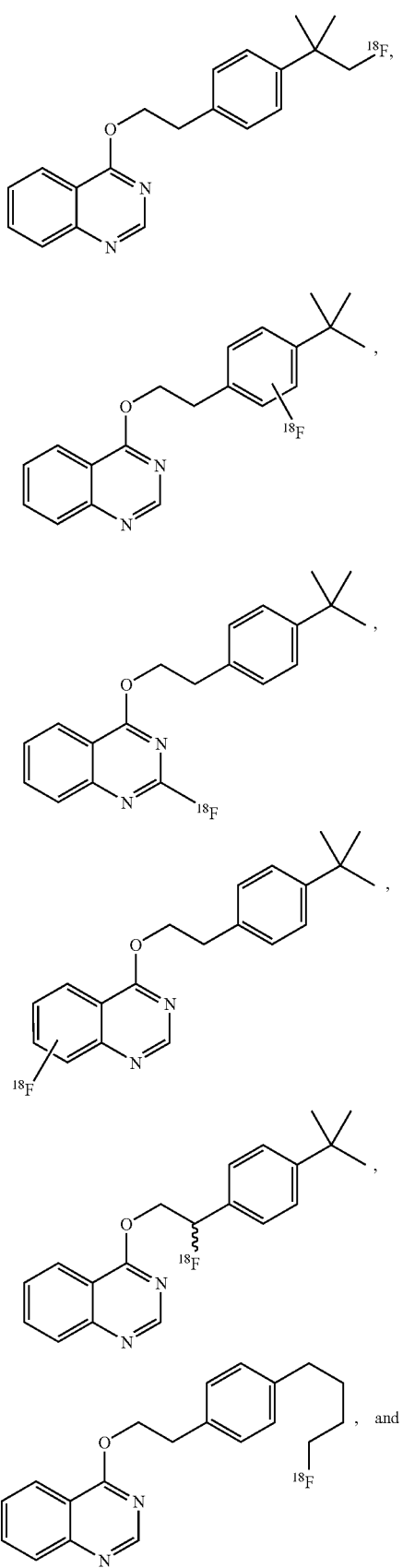

-continued

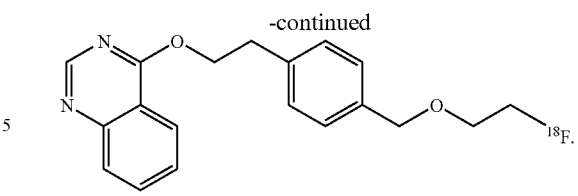

Imaging Moieties

Nuclear medicine contrast agents of the present disclosure include $^{11}C$, $^{13}N$, $^{18}F$, $^{123}I$, $^{125}I$, $^{99m}Tc$, $^{95}Tc$, $^{111}In$, $^{62}Cu$, $^{64}Cu$, $^{67}Ga$, and $^{68}Ga$. $^{11}C$-Palmitate has been used to probe fatty acid oxidation and $^{11}C$-acetate has been used to assess oxidative metabolism in the myocardium (*Circulation* 1987, 76, 687-696). $^{13}N$-Ammonia has been used widely to image myocardial perfusion (*Circulation* 1989, 80, 1328-37). Agents based on $^{18}F$ have been used as imaging agents for hypoxia and cancer (*Drugs of the Future* 2002, 27, 655-667). 15-(p-($^{123}I$)-iodophenyl)-pentadecanoic acid and 15-(p-($^{123}I$)-iodophenyl)-3(R,S)-methylpentadecanoic acid are two iodinated agents that have been used for imaging myocardial metabolism. In one embodiment, the imaging moiety employed in the present contrast agents is $^{18}F$. Further imaging moieties of the present disclosure may be comprised of one or more X-ray absorbing or "heavy" atoms of atomic number 20 or greater, further comprising an optional linking moiety, L, between the parent molecular moiety and the X-ray absorbing atoms. A frequently used heavy atom in X-ray contrast agents is iodine. Recently, X-ray contrast agents comprised of metal chelates (U.S. Pat. No. 5,417,959) and polychelates comprised of a plurality of metal ions (U.S. Pat. No. 5,679,810) have been disclosed. More recently, multinuclear cluster complexes have been disclosed as X-ray contrast agents (U.S. Pat. No. 5,804,161, WO 91/14460, and WO 92/17215). In certain embodiments of the present disclosure the specific metals used in the X-ray contrast agents include Re, Sm, Ho, Lu, Pm, Y, Bi, Pd, Gd, La, Au, Au, Yb, Dy, Cu, Rh, Ag, and Ir.

MRI contrast agents of the present disclosure may be comprised of one or more analog moieties attached to one or more paramagnetic metal ions, further comprising an optional linking moiety, L, between the analog moieties and the paramagnetic metal ions. The paramagnetic metal ions may be present in the form of metal chelates or complexes or metal oxide particles. U.S. Pat. Nos. 5,412,148, and 5,760,191, describe examples of chelators for paramagnetic metal ions for use in MRI contrast agents. U.S. Pat. Nos. 5,801,228, 5,567,411, and 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents. Examples of specific metals include $Gd^{3+}$, $Fe^{3+}$, $In^{3+}$, and $Mn^{2+}$.

The ultrasound contrast agents of the present disclosure may comprise a plurality of analog moieties attached to or incorporated into a microbubble of a biocompatible gas, a liquid carrier, and a surfactant microsphere, further comprising an optional linking moiety, L, between the analog moieties and the microbubble. In this context, the term "liquid carrier" means aqueous solution and the term "surfactant" means any amphiphilic material which may produce a reduction in interfacial tension in a solution. A list of suitable surfactants for forming surfactant microspheres is disclosed, for example, in EP0727225A2. The term "surfactant microsphere" includes microspheres, nanospheres, liposomes, vesicles and the like. The biocompatible gas can be any physiologically accepted gas, including, for example, air, or a fluorocarbon, such as a $C_3$-$C_5$ perfluoroalkane, which provides the difference in echogenicity and thus the contrast in ultrasound imaging. The gas may be encapsulated, contained, or otherwise constrained in or by the microsphere to which is attached the analog moiety, optionally via a linking group. The attachment can be covalent, ionic or by van der Waals forces. Specific examples of such contrast agents include, for example, lipid encapsulated perfluorocarbons with a plurality of tumor neovasculature receptor binding peptides, polypeptides or peptidomimetics. Examples of gas filled imaging moieties include those found in U.S. patent application Ser. No. 09/931,317, filed Aug. 16, 2001, and U.S. Pat. Nos. 5,088,499, 5,547,656, 5,228,446, 5,585,112, and 5,846,517.

Chelators

Many approaches to labeling compounds with $^{99m}Tc$ are known, including direct labeling of the compound or inclusion of a chelating moiety ("chelator"). In one embodiment, the chelator is DADT, MAG3, MAMA, PAMA, or DOTA.

The compounds of the disclosure may optionally contain a chelator ("C") In certain embodiments of the compounds of the disclosure, the chelator is a surfactant capable of forming an echogenic substance-filled lipid sphere or microbubble. In certain other embodiments, the chelator is a bonding unit having a formula selected from

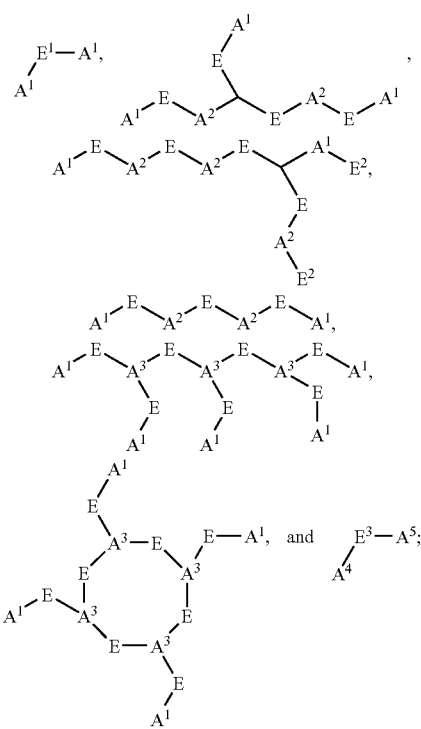

wherein each $A^1$ is independently selected from —$NR^{46}R^{47}$, —$NHR^{53}$, —SH, —S(Pg), —OH, —$PR^{46}R^{47}$, —$P(O)R^{48}R^{49}$, and a bond to the compound that binds MC-1;

each $A^2$ is independently selected from $N(R^{53})$, $N(R^{46})$, S, O, $P(R^{46})$, and —$OP(O)(R^{48})O$—;

$A^3$ is N;

$A^4$ is selected from OH and $OC(=O)C_1$-$C_{20}$ alkyl;

$A^5$ is $OC(=O)C_1$-$C_{20}$ alkyl;

each E is independently selected from $C_1$-$C_{16}$ alkylene substituted with 0-3 $R^{50}$, $C_6$-$C_{10}$ arylene substituted with 0-3 $R^{50}$, $C_3$-$C_{10}$ cycloalkylene substituted with 0-3 $R^{50}$, heterocyclyl-$C_1$-$C_{10}$ alkylene substituted with 0-3 $R^{50}$, $C_6$-$C_{10}$ aryl-$C_1$-$C_{10}$ alkylene substituted with 0-3 $R^{50}$, and heterocyclylene substituted with 0-3 $R^{50}$;

$E^1$ is selected from a bond and E;

each $E^2$ is independently selected from $C_1$-$C_{16}$ alkyl substituted with 0-3 $R^{50}$, $C_6$-$C_{10}$ aryl substituted with 0-3 $R^{50}$, $C_3$-$C_{10}$ cycloalkyl substituted with 0-3 $R^{50}$, heterocyclyl-$C_1$-$C_{10}$ alkyl substituted with 0-3 $R^{50}$, $C_6$-$C_{10}$ aryl-$C_1$-$C_{10}$ alkyl substituted with 0-3 $R^{50}$, $C_1$-$C_{10}$ alkyl-$C_6$-$C_{10}$ aryl substituted with 0-3 $R^{50}$, and heterocyclyl substituted with 0-3 $R^{50}$;

$E^3$ is $C_1$-$C_{10}$ alkylene substituted with 1-3 $R^{59}$;

Pg is a thiol protecting group;

$R^{46}$ and $R^{47}$ are each independently selected from a bond to the compound that binds MG-1, hydrogen, $C_1$-$C_{10}$ alkyl substituted with 0-3 $R^{50}$, aryl substituted with 0-3 $R^{50}$, $C_3$-$C_{10}$ cycloalkyl substituted with 0-3 $R^{50}$, heterocyclyl-$C_1$-$C_{10}$ alkyl substituted with 0-3 $R^{50}$, $C_6$-$C_{10}$ aryl-$C_1$-$C_{10}$ alkyl substituted with 0-3 $R^{50}$, and heterocyclyl substituted with 0-3 $R^{50}$;

$R^{48}$ and $R^{49}$ are each independently selected from a bond to the compound that binds MC-1, —OH, $C_1$-$C_{10}$ alkyl substituted with 0-3 $R^{50}$, aryl substituted with 0-3 $R^{50}$, $C_3$-$C_{10}$ cycloalkyl substituted with 0-3 $R^{50}$, heterocyclyl-$C_1$-$C_{10}$ alkyl substituted with 0-3 $R^{50}$, $C_6$-$C_{10}$ aryl-$C_1$-$C_{10}$ alkyl substituted with 0-3 $R^{50}$, and heterocyclyl substituted with 0-3 $R^{50}$;

each $R^{50}$ is independently selected from a bond to the compound that binds MC-1, =O, halo, trifluoromethyl, cyano, —$CO_2R^{51}$, —$C(=O)R^{51}$, —$C(=O)N(R^{51})_2$, —CHO, —$CH_2OR^{51}$, —$OC(=O)R^{51}$, —$OC(=O)OR^{51}$, —$OR^{51}$, —$OC(=O)N(R^{51})_2$, —$NR^{51}C(=O)R^{51}$, —$NR^{51}C(=O)OR^{51}$, —$NR^{51}C(=O)N(R^{51})_2$, —$NR^{51}SO_2N(R^{51})_2$, —$NR^{51}SO_2R^{51}$, —$SO_3H$, —$SO_2R^{51}$, —$SR^{51}$, —$S(=O)R^{51}$, —$SO_2N(R^{51})_2$, —$N(R^{51})_2$, —NHC(=S)$NHR^{51}$, =$NOR^{51}$, $N_2$, —$C(=O)NHOR^{51}$, —$C(=O)NHN(R^{51})_2$, —$OCH_2CO_2H$, 2-(1-morpholino) ethoxy, $C_1$-$C_5$ alkyl, $C_2$-$C_4$ alkenyl, $C_3$-$C_6$ cycloalkyl, $C_3$-$C_6$ cycloalkylmethyl, $C_2$-$C_6$ alkoxyalkyl, aryl substituted with 0-2 $R^{51}$, and heterocyclyl;

each $R^{51}$ is independently selected from a bond to the compound that binds MC-1, hydrogen, $C_1$-$C_6$ alkyl, phenyl, benzyl, and $C_{1-6}$ alkoxy;

$R^{53}$ is a co-ordinate bond to a metal;

each $R^{59}$ selected from $R^{61}$, =O, —$CO_2R^{60}$, —$C(=O)R^{60}$, —$C(=O)N(R^{60})_2$, —$CH_2OR^{60}$, —$OR^{60}$, —$N(R^{60})_2$, and $C_2$-$C_4$ alkenyl;

each $R^{60}$ is independently selected from $R^{61}$, hydrogen, $C_1$-$C_6$ alkyl, phenyl, benzyl, and trifluoromethyl; and $R^{61}$ is a bond to the compound that binds MC-1;

wherein at least one of $A^1$, $R^{46}$, $R^{47}$, $R^{48}$, $R^{49}$, $R^{50}$, $R^{51}$, and $R^{61}$ is a bond to the compound that binds MC-1.

Methods of Making

Typically $^{18}F$ labeled compounds are synthesized by $S_n2$ displacement of an appropriate leaving group. These leaving groups are preferrably sulfonic acid esters such as toluenesulfonate (tosylate, TsO), methanesulfonate (mesylate, MsO), or trifluoromethanesulfonate (triflate, TfO). The leaving group may also be a halide, a phosphinieoxide (via Mitsunobu reaction), or an internal leaving group (such as an epoxide or cyclic sulfate). These compounds are made from highly activated, dry $K^{18}F$, that is made "hotter" by the addition of cryptands such as krytofix[2.2.2]. Purification is generally via salt removal by reverse-phase chromatography (Sep-Pak).

Representative methods of making the contrast agents are described in the following examples. The foregoing chemical transformations may be conducted using techniques which would be readily apparent to one of ordinary skill in the art, once armed with the teachings in the present applications. Representative reaction solvents include, for example, DMF, NMP, DMSO, THF, ethyl acetate, dichloromethane, and chloroform. The reaction solution may be kept neutral or basic by the addition of an amine such as triethylamine or DIEA. Reactions may be carried out at ambient temperatures and protected from oxygen and water with a nitrogen atmosphere.

Temporary protecting groups may be used to prevent other reactive functionality, such as amines, thiols, alcohols, phenols, and carboxylic acids, from participating in the reaction. Representative amine protecting groups include, for example, tert-butoxycarbonyl and trityl (removed under mild acidic conditions), Fmoc (removed by the use of secondary amines such as piperidine), and benzyloxycarbonyl (removed by strong acid or by catalytic hydrogenolysis). The trityl group may also used for the protection of thiols, phenols, and alcohols. In certain embodiments the carboxylic acid protecting groups include, for example, ter-butyl ester (removed by mild acid), benzyl ester (usually removed by catalytic hydrogenolysis), and alkyl esters such as methyl or ethyl (usually removed by mild base). All protecting groups may be removed at the conclusion of synthesis using the conditions described above for the individual protecting groups, and the final product may be purified by techniques which would be readily apparent to one of ordinary skill in the art, once armed with the present disclosure.

Use

The contrast agents of the present disclosure may be used in a method of imaging, including methods of imaging in a patient comprising administering the contrast agent to the patient by injection, infusion, or any other known method, and imaging the area of the patient wherein the event of interest is located.

The useful dosage to be administered and the particular mode of administration will vary depending upon such factors as age, weight, and particular region to be treated, as well as the particular contrast agent used, the diagnostic use contemplated, and the form of the formulation, for example, suspension, emulsion, microsphere, liposome, or the like, as will be readily apparent to those skilled in the art.

Typically, dosage is administered at lower levels and increased until the desirable diagnostic effect is achieved. In one embodiment, the above-described contrast agents may be administered by intravenous injection, usually in saline solution, at a dose of about 0.1 to about 100 mCi per 70 kg body weight (and all combinations and subcombinations of dosage ranges and specific dosages therein), or preferably at a dose of about 0.5 to about 50 mCi. Imaging is performed using techniques well known to the ordinarily skilled artisan.

For use as nuclear medicine contrast agents, the compositions of the present disclosure, dosages, administered by intravenous injection, will typically range from about 0.5 µmol/kg to about 1.5 mmol/kg (and all combinations and subcombinations of dosage ranges and specific dosages therein), preferably about 0.8 µmol/kg to about 1.2 mmol/kg.

For use as MRI contrast agents, the compositions of the present disclosure may be used in a similar manner as other MRI agents as described in U.S. Pat. Nos. 5,155,215; 5,087, 440; *Magn. Reson. Med.* 1986, 3, 808; *Radiology* 1988, 166, 835; and *Radiology* 1988, 166, 693. Generally, sterile aqueous solutions of the contrast agents may be administered to a patient intravenously in dosages ranging from about 0.01 to about 1.0 mmoles per kg body weight (and all combinations and subcombinations of dosage ranges and specific dosages therein).

The ultrasound contrast agents of the present disclosure may be administered by intravenous injection in an amount from about 10 to about 30 µL (and all combinations and subcombinations of dosage ranges and specific dosages therein) of the echogenic gas per kg body weight or by infusion at a rate of approximately 3 µL/kg/min.

Another aspect of the present disclosure is diagnostic kits for the preparation of diagnostic agents for detecting, imaging, and/or monitoring myocardial perfusion. Diagnostic kits of the present disclosure comprise one or more vials containing the sterile, non-pyrogenic, formulation comprising a predetermined amount of a reagent of the present disclosure, and optionally other components such as one or two ancillary ligands such as tricine and 3-[bis(3-sulfophenyl)phosphine] benzenesulfonic acid (TPPTS), reducing agents, transfer ligands, buffers, lyophilization aids, stabilization aids, solubilization aids and bacteriostats. The kits may also comprise a reducing agent, such as, for example, tin(II).

Buffers useful in the preparation of contrast agents and kits include, for example, phosphate, citrate, sulfosalicylate, and acetate buffers. A more complete list can be found in the United States Pharmacopoeia.

Lyophilization aids useful in the preparation of contrast agents and kits include, for example, mannitol, lactose, sorbitol, dextran, FICOLL® polymer, and polyvinylpyrrolidine (PVP).

Stabilization aids useful in the preparation of contrast agents and kits include, for example, ascorbic acid, cysteine, monothioglycerol, sodium bisulfite, sodium metabisulfite, gentisic acid, and inositol.

Solubilization aids useful in the preparation of contrast agents and kits include, for example, ethanol, glycerin, polyethylene glycol, propylene glycol, polyoxyethylene sorbitan monooleate, sorbitan monolocate, polysorbates, poly(oxyethylene)-poly(oxypropylene)-poly(oxyethylene) block copolymers ("Pluronics") and lecithin. In certain embodiments the solubilizing aids are polyethylene glycol and Pluronics.

Bacteriostats useful in the preparation of contrast agents and kits include, for example, benzyl alcohol, benzalkonium chloride, chlorbutanol, and methyl, propyl, or butyl paraben.

A component in a diagnostic kit can also serve more than one function. For example, a reducing agent for a radionuclide can also serve as a stabilization aid, or a buffer can also serve as a transfer ligand, or a lyophilization aid can also serve as a transfer, ancillary, or co-ligand.

The compounds herein described may have asymmetric centers. Unless otherwise indicated, all chiral, diastereomeric and racemic forms are included in the present disclosure. Many geometric isomers of olefins, C=N double bonds, and the like can also be present in the compounds described herein, and all such stable isomers are contemplated in the present disclosure. It will be appreciated that compounds of the present disclosure may contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present disclosure. The D- and L-isomers of a particular amino acid are designated herein using the conventional 3-letter abbreviation of the amino acid, as indicated by the following examples: D-Leu, or L-Leu.

For the sake of simplicity, connection points ("—") are not depicted. When an atom or compound is described to define a variable, it is understood that it is intended to replace the variable in a manner to satisfy the valency of the atom or compound. For example, if a variable A" was identified as $C(R^{80})=C(R^{80})$, both carbon atoms would form a part of the chain in order to satisfy their respective valences.

When any variable occurs more than one time in any substituent or in any formula, its definition in each occurrence is independent of its definition at every other occurrence. Thus, for example, if a group, or plurality of groups, is shown to be substituted with 0-2 $R^{80}$, then said group(s) may optionally be substituted with up to two $R^{80}$, and $R^{80}$ at each occurrence in each group is selected independently from the defined list of possible $R^{80}$. Also, by way of example, for the group —N($R^{81}$)$_2$, each of the two $R^{81}$ substituents on N is independently selected from the defined list of possible $R^{81}$. Combinations of substituents and/or variables are permissible only if such combinations result in stable compounds. When a bond to a substituent is shown to cross the bond connecting two atoms in a ring, then such substituent may be bonded to any atom on the ring.

Definitions

The number of carbon atoms in any particular group is denoted before the recitation of the group. For example, the term "$C_6$-$C_{10}$aryl" denotes an aryl group containing from six to ten carbon atoms, and the term "$C_6$-$C_{10}$aryl-$C_1$-$C_{10}$alkyl," refers to an aryl group of six to ten carbon atoms attached to the parent molecular moiety through an alkyl group of one to ten carbon atoms.

The term "alkenyl," as used herein, refers to a straight or branched chain hydrocarbon containing at least one carbon-carbon double bond.

The term "alkoxy," as used herein, refers to a $C_1$-$C_6$ alkyl group attached to the parent molecular moiety through an oxygen atom.

The term "alkoxyalkyl," as used herein, refers to a $C_1$-$C_6$ alkyl group substituted with one, two, or three alkoxy groups.

The term "alkyl," as used herein, refers to a group derived from a straight or branched chain saturated hydrocarbon.

The term "alkylaryl," as used herein, refers to an alkyl group attached to the parent molecular moiety through an aryl group.

The term "alkylene," as used herein, refers to a divalent group derived from a straight or branched chain saturated hydrocarbon.

The term "alkyloxy," as used herein, refers to a $C_1$-$C_6$ alkyl group attached to the parent molecular moiety through an oxygen atom.

The term "analog moiety," as used herein, refers to the compounds of the present disclosure excluding the imaging moiety or moieties.

The term "aryl," as used herein, refers to a phenyl group, or a bicyclic fused ring system wherein one or more of the rings is a phenyl group. Bicyclic fused ring systems consist of a phenyl group fused to a monocyclic cycloalkenyl group, a monocyclic cycloalkyl group, or another phenyl group. The aryl groups of the present invention can be attached to the parent molecular moiety through any substitutable carbon atom in the group. Representative examples of aryl groups include, but are not limited to, anthracenyl, azulenyl, fluorenyl, indanyl, indenyl, naphthyl, phenyl, and tetrahydronaphthyl.

The term "arylalkyl," as used herein, refers to an alkyl group substituted with one, two, or three aryl groups.

The term "arylalkylene," as used herein, refers to a divalent arylalkyl group, where one point of attachment to the parent molecular moiety is on the aryl portion and the other is on the alkyl portion.

The term "arylene," as used herein, refers to a divalent aryl group.

As used herein, the terms "ancillary" or "co-ligands" refers to ligands that serve to complete the coordination sphere of the radionuclide together with the chelator or radionuclide bonding unit of the reagent. For radiopharmaceuticals comprising a binary ligand system, the radionuclide coordination sphere comprises one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprising two chelators or bonding units from one or two reagents and one ancillary or co-ligand are both considered to comprise binary ligand systems. For radiopharmaceuticals comprising a ternary ligand system, the radionuclide coordination sphere comprises one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to comprise a ternary ligand system.

Ancillary or co-ligands useful in the preparation of radiopharmaceuticals and in diagnostic kits useful for the preparation of said radiopharmaceuticals comprise one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "bacteriostat" is a component that inhibits the growth of bacteria in a formulation either during its storage before use of after a diagnostic kit is used to synthesize a radiopharmaceutical.

The term "bubbles" or "microbubbles," as used herein, refers to vesicles which are generally characterized by the presence of one or more membranes or walls surrounding an internal void that is filled with a gas or precursor thereto. Exemplary bubbles or microbubbles include, for example, liposomes, micelles, and the like.

The terms "chelator" and "bonding unit," as used herein, refer to the moiety or group on a reagent that binds to a metal ion through one or more donor atoms.

The term "contrast agent," as used herein, refers to an agent used to highlight specific areas so that organs, blood vessels, and/or tissues are more visible. By increasing the visibility of the surfaces being studied, the presence and extent of disease and/or injury can be determined.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3,1.1] heptyl, and adamantyl.

The term "$C_3$-$C_{10}$ cycloalkylene," as used herein, refers to a divalent cycloalkyl group containing from three to ten carbon atoms.

The term "diagnostic imaging," as used herein, refers to a procedure used to detect a contrast agent.

A "diagnostic kit" or "kit" comprises a collection of components, termed the formulation, in one or more vials which are used by the practicing end user in a clinical or pharmacy setting to synthesize diagnostic radiopharmaceuticals. The kit preferably provides all the requisite components to synthesize and use the diagnostic pharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes, shielding, imaging equipment, and the like. Contrast agents are provided to the end user in their final form in a formulation contained typically in one vial, as either a lyophilized solid or an aqueous solution. The end user typically reconstitutes the lyophilized material with water or saline and withdraws the patient dose or just withdraws the dose from the aqueous solution formulation as provided.

The term "donor atom," as used herein, refers to the atom directly attached to a metal by a chemical bond.

The terms "halo" and "halogen," as used herein, refer to F, Cl, Br, or I.

The term "haloalkyl," as used herein, refers to a $C_1$-$C_6$ alkyl group substituted by one, two, three, or four halogen atoms.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a four- to six-membered aromatic or non-aromatic ring containing zero, one, or two additional heteroatoms selected from N, O, and S. The heteroaryl groups are attached to the parent molecular moiety through any substitutable carbon or nitrogen atom in the group. Representative examples of heteroaryl groups include, but are not limited to, benzoxadiazolyl, benzoxazolyl, benzofuranyl, benzothienyl, furanyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl.

The term "heterocyclyl," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group. The heterocyclyl groups of the present invention can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

The term "heterocyclylalkyl," as used herein, refers to an alkyl group substituted with one, two, or three heterocyclyl groups.

The term "heterocyclylalkylene," as used herein, refers to a divalent heterocyclylalkyl group, where one point of attachment to the parent molecular moiety is on the heterocyclyl portion and the other is on the alkyl portion.

The term "heterocyclylene," as used herein, refers to a divalent heterocyclyl group.

The term "hydroxy," as used herein, refers to —OH.

The term "imaging moiety," as used herein, refer to a portion or portions of a molecule that allow for the detection, imaging, and/or monitoring of the presence and/or progression of a condition(s), pathological disorder(s), and/or disease(s).

The term "linking group," as used herein, refers to a portion of a molecule that serves as a spacer between two other portions of the molecule. Linking groups may also serve other functions as described herein. Examples of linking groups include linear, branched, or cyclic alkyl, aryl, ether, polyhydroxy, polyether, polyamine, heterocyclic, aromatic, hydrazide, peptide, peptoid, or other physiologically compatible covalent linkages or combinations thereof.

As used herein, the term "lipid" refers to a synthetic or naturally-occurring amphipathic compound which comprises a hydrophilic component and a hydrophobic component. Lipids include, for example, fatty acids, neutral fats, phosphatides, glycolipids, aliphatic alcohols and waxes, terpenes and steroids. Exemplary compositions which comprise a lipid compound include suspensions, emulsions and vesicular compositions.

"Liposome" refers to a generally spherical cluster or aggregate of amphipathic compounds, including lipid compounds, typically in the form of one or more concentric layers, for example, bilayers. They may also be referred to herein as lipid vesicles.

A "lyophilization aid" is a component that has favorable physical properties for lyophilization, such as the glass transition temperature, and is generally added to the formulation to improve the physical properties of the combination of all the components of the formulation for lyophilization.

The term "oxo," as used herein, refers to =O.

As used herein, the phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt," as used herein, represents salts or zwitterionic forms of the compounds of the present invention which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

By "reagent" is meant a compound of this disclosure capable of direct transformation into a metallopharmaceutical of this disclosure. Reagents may be utilized directly for the preparation of the metallopharmaceuticals of this disclosure or may be a component in a kit of this disclosure.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include, for example, stannous chloride, stannous fluoride, formamidine sulfinic acid, ascorbic acid, cysteine, phosphines, and cuprous or ferrous salts. Other reducing agents are described, for example, in Brodack et. al., PCT Application 94/22496.

A "stabilization aid" is a component that is typically added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting preferentially with species that degrade other components or the metallopharmaceuticals.

By "stable compound" or "stable structure" is meant herein a compound that is sufficiently robust to survive isolation to a useful degree of purity from a reaction mixture, and formulation into an efficacious pharmaceutical agent.

A "solubilization aid" is a component that improves the solubility of one or more other components in the medium required for the formulation.

The term "thiol protecting group," as used herein, refers to a group intended to protect a thiol group against undesirable reactions during synthetic procedures. Any thiol protecting group known in the art may be used. Examples of thiol protecting groups include, but are not limited to, the following: acetaimidomethyl, benzamidomethyl, 1-ethoxyethyl, benzoyl, and triphenylmethyl.

A "transfer ligand" is a ligand that forms an intermediate complex with a metal ion that is stable enough to prevent unwanted side-reactions but labile enough to be converted to a contrast agent. The formation of the intermediate complex is kinetically favored while the formation of the metallopharmaceutical is thermodynamically favored. Transfer ligands useful in the preparation of contrast agents and in diagnostic kits useful for the preparation of diagnostic radiopharmaceuticals include, for example, gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

As used herein, the term "vesicle" refers to a spherical entity which is characterized by the presence of an internal void. In one embodiment vesicles are formulated from lipids, including the various lipids described herein. In any given vesicle, the lipids may be in the form of a monolayer or bilayer, and the mono- or bilayer lipids may be used to form one or more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

As used herein, the term "vesicular composition" refers to a composition which is formulate from lipids and which comprises vesicles.

The present disclosure will now be described in connection with certain embodiments which are not intended to limit its scope. On the contrary, the present disclosure covers all alternatives, modifications, and equivalents as can be included within the scope of the claims. Thus, the following examples will illustrate one practice of the present invention, it being understood that the examples are for the purposes of illustration of certain embodiments and are presented to provide what is believed to be the most useful and readily understood description of its procedures and conceptual aspects.

Synthesis of Fenazaquin Analog:

EXAMPLE 1A

Synthesis of 4-[4-(2-Hydroxyethyl)phenyl]-4-oxo-butyric acid methyl ester

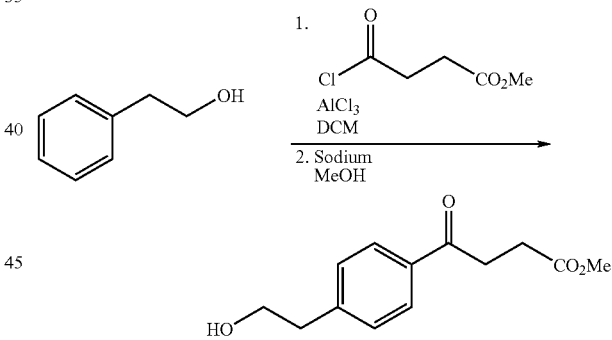

To a dry 250 mL flask under a nitrogen atmosphere was added phenethyl alcohol (2.50 g, 0.02 mol), anhydrous dichloromethane (150 mL), and methyl-4-chloro-4-oxobutyrate (6.02 g, 0.04 mol). The contents of the flask were cooled to 0° C. with an ice bath. To the solution was added aluminum chloride (25 g, 0.2 mol) in portions being careful to avoid a violent exotherm. The resulting yellowish mixture was stirred for 3 hours. At this point the reaction was quenched with ice water. The mixture was diluted with dichloromethane and transferred to a separatory funnel. The organic layer was washed with a saturated solution of sodium bicarbonate, brine and then dried over magnesium sulfate. Filtration and concentration of the filtrate under reduced pressure provided a crude yellow oil. The oil was suspended in anhydrous methanol (100 mL) and sodium metal was added to the mixture until a pH of 9 was obtained. The mixture was stirred for 3 hours. The volume was reduced and then diluted with ethyl acetate. The solution was transferred to a separatory flannel and washed with aqueous 0.05 N hydrochloric acid, brine and dried over magnesium sulfate. The solution was concentrated under reduced pressure to give a crude yellow oil with a mass of 5.88 g. Column chromatography [silica gel; eluent hexanes-ethyl acetate (3:2)] provided the desired product (2.69 g, 57%). $^1$H (CDCl$_3$) δ(ppm): 2.65 (t, 2H); 2.81 (t, 2H); 3.19 (t, 2H); 3.6 (s, 3H); 3.75 (t, 2H); 7.22 (d, 2H); 7.81 (d, 2H). $^{13}$C (CDCl$_3$) δ(ppm): 27.76, 33.03, 38.66, 51.52, 62.68, 127.97, 128.99, 134.47, 144.78, 173.21, 197.64.

EXAMPLE 1B

Synthesis of 4-[4-(2-hydroxyethyl)phenyl]butyric acid methyl ester

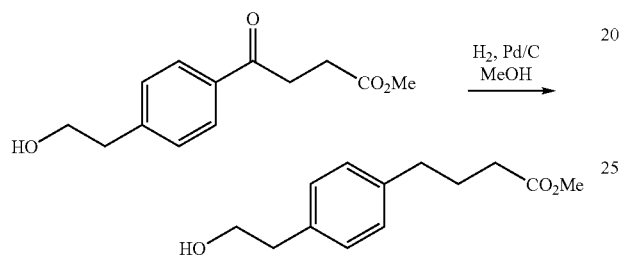

A mixture of Example 1A (2.50 g, 11 mmol), 10% Pd/C (0.25 g, 0.23 mmol of Pd metal) in anhydrous methanol (25 mL) was first degassed to remove air (two vacuum/H$_2$ cycles) after which it was capped and a balloon filled with H$_2$ was applied to it for 12 hours. After this time the reaction mixture was filtered through diatomaceous earth (Celite®) and the filtrate was concentrated under reduced pressure to give 2.32 g of crude material. Column chromatography [silica gel; eluent hexanes-ethyl acetate (2:1)] provided the desired product (0.92 g, 39%). $^1$H (CDCl$_3$) δ(ppm): 1.91-1.96 (m, 2H); 2.32 (t, 2H); 2.62 (t, 2H); 2.83 (t, 2H); 3.66 (s, 3H); 3.85 (t, 2H); 7.11-7.15 (m, 4H).

EXAMPLE 1C

Synthesis of 4-{4-[2-(quinazolin-4-yloxy)ethyl]phenyl}butyric acid methyl ester

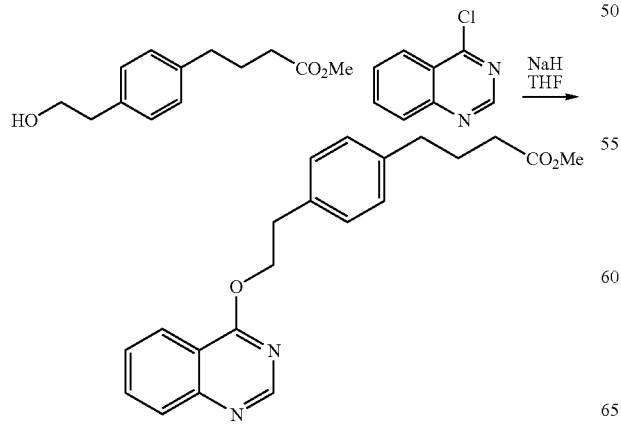

A dry 50 mL flask was fitted with an addition funnel. To the flask were added 4-chloroquinazoline (592 mg, 3.6 mmol), anhydrous tetrahydrofuran (10 mL), and 60 wt % sodium hydride (187 mg, 4.7 mmol). A solution of Example 1B (800 mg, 3.6 mmol) in anhydrous tetrahydrofuran (10 mL) was added dropwise using the addition funnel. The reaction was stirred for 3.5 hours. The reaction was diluted with ethyl acetate and quenched by the addition of aqueous 0.1 N hydrochloric acid. The mixture was transferred to a separatory funnel and washed with brine. The organic layer was dried over magnesium sulfate, filtered, and concentrated. Column chromatography [silica gel; eluent hexanes-ethyl acetate (4:1)] provided the desired product (538 mg, 43%). $^1$H (CDCl$_3$) δ ppm): 1.92-1.98 (m, 2H); 2.33 (t, 2H); 2.64 (t, 2H); 3.19 (t, 2H); 3.66 (s, 3H); 4.79 (t, 2H); 7.15 (d, 2H); 7.27 (d, 2H); 7.57 (t, 1H); 7.83 (t, 1H); 7.94 (d, 1H); 8.15 (d, 1H); 8.80 (s, 1H). 26.68, 33.59, 34.93, 35.03, 51.67, 67.89, 116.48, 123.72, 127.23, 127.82, 128.87, 129.24, 133.74, 135.76, 139.90, 151.08, 154.56, 166.89, 174.10.

EXAMPLE 1D

Synthesis of 4-{4-[2-(Quinazolin-4-yloxy)ethyl]phenyl}butan-1-ol

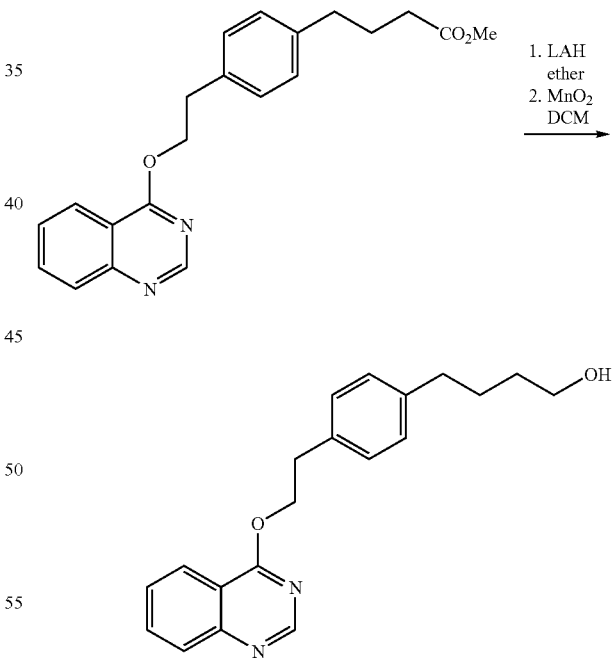

To a dry 15 mL flask was added lithium aluminum hydride (233 mg, 6.0 mmol) and anhydrous diethyl ether (3 mL). The mixture was cooled with an ice bath. A solution of Example 1C (538 mg, 1.54 mmol) in anhydrous diethyl ether (3 mL) was slowly added with vigorous stirring. The bath was removed and the slurry was stirred for 15 minutes. The reaction was quenched with water (0.233 mL), aqueous 15% sodium hydroxide (0.233 mL) and water (0.699 mL). The white solid was filtered and the filtrate was dried over magnesium sulfate, filtered, and concentrated under reduced pressure to give a clear oil. The oil was then dissolved in anhydrous dichloromethane (10 mL) and manganese(IV) oxide (500 mg, 5.8 mmol) was added to the solution. The mixture was stirred for 12 hours. Filtration through diatomaceous earth (Celite®) followed by concentration of the filtrate under reduced pressure afforded 395 mg of crude product. Column chromatography [silica gel; eluent pentane-ethyl acetate (2:3)] provided the desired product (225 mg, 49%). $^1$H (CDCl$_3$) δ(ppm): 1.55-1.61 (m, 2H); 1.65-1.68 (m, 2H); 2.61 (t, 2H); 3.17 (t, 2H); 3.64 (t, 2H); 4.79 (t, 2H); 7.12 (d, 2H); 7.23 (d, 2H); 7.56 (t, 1H); 7.82 (t, 1H); 7.93 (d, 1H); 8.14 (d, 1H); 8.77 (s, 1H). $^{13}$C(CDCl$_3$) δ(ppm): 27.52, 32.31, 34.89, 35.21, 62.81, 67.74, 116.67, 123.54, 127.08, 127.49, 128.63, 128.98, 133.61, 135.23, 140.64, 150.68, 154.29, 166.79.

EXAMPLE 1E

Synthesis of Toluene-4-sulfonic acid 4-{4-[2-(quinazolin-4-yloxyethyl]phenyl}butyl ester

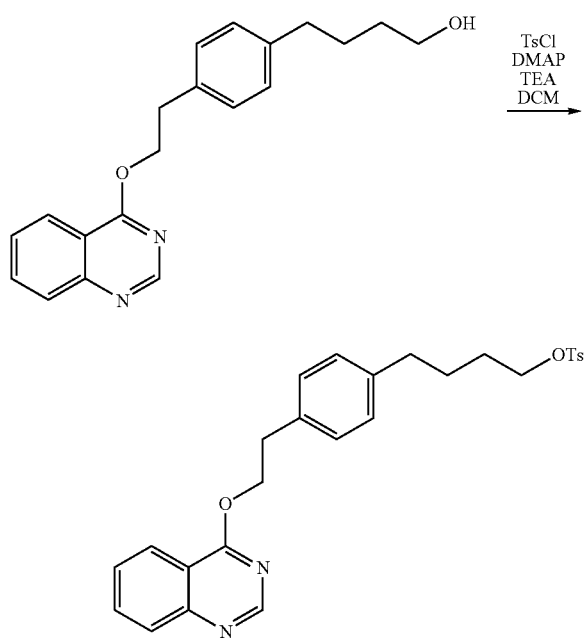

To a dry 10 mL flask was added p-toluenesulfonyl chloride (32.5 mg, 0.17 mmol), 4-(dimethylamino)pyridine (20.7 mg, 0.17 mmol), Example 1D (50.0 mg, 0.16 mmol), anhydrous dichloromethane (1 mL) and triethylamine (17.2 mg, 0.17 mmol). The resulting solution was stirred for 2 hours, concentrated under reduced pressure, and purified by column chromatography [silica gel; eluent pentane-ethyl acetate (1.86:1)] to provide the desired product (52 mg, 70%). $^1$H (CDCl$_3$) δ(ppm): 1.64-1.68 (m, 4H); 2.44 (s, 3H); 2.56 (t, 2H); 3.19 (t, 2H); 4.04 (t, 2H); 4.78 (t, 2H); 7.08 (d, 2H); 7.26 (d, 2H); 7.57 (t, 1H); 7.78 (d, 2H); 7.84 (t, 1H); 8.14 (d, 1H); 8.80 (s, 1H).

EXAMPLE 1F

Synthesis of 4-{2-[4-(4-Fluorobutyl)phenyl]ethoxy}quinazoline

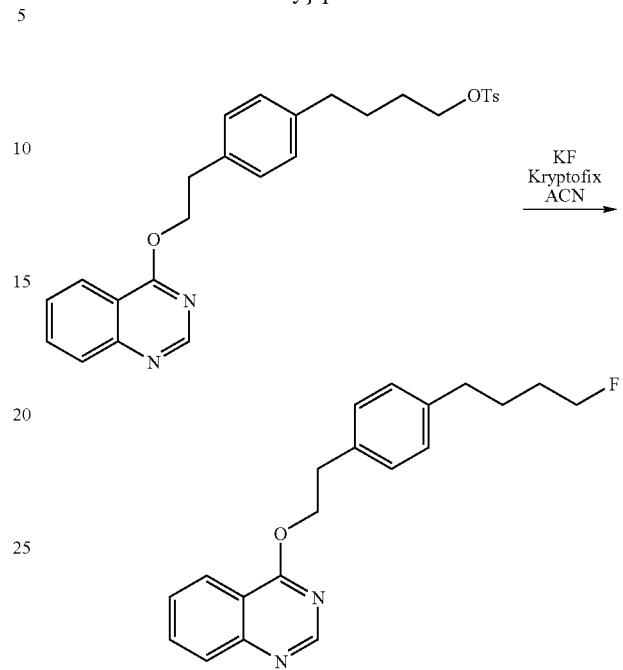

A dry 5 mL flask was fitted with a reflux condenser. To the flask was added potassium fluoride (6.1 mg, 0.1 mmol), kryptofix (40 mg, 0.1 mmol) and anhydrous acetonitrile (0.5 mL). To the resulting solution was added a solution of Example 1E (25 mg, 0.05 mmol) in anhydrous acetonitrile (1 mL). The flask was placed in a 90° C. oil bath. The solution was stirred for 1 hour. After cooling the reaction mixture was diluted with diethyl ether, transferred to a separatory funnel, and washed with aqueous (0.1 N hydrochloric acid, saturated aqueous solution of sodium bicarbonate, and then brine. The organic layer was dried with magnesium sulfate, filtered, and concentrated under reduced pressure. Column chromatography [silica gel; eluent hexanes-ethyl acetate (3:1)] provided the desired product (10.7 mg, 63%). $^1$H (CDCl$_3$) δ(ppm): 1.65-1.73 (m, 4H); 2.63 (t, 2H); 3.17 (t, 2H); 4.40 (t, 1H); 4.48 (t, 1H); 4.77 (t, 2H); 7.13 (d, 2H); 7.24 (d, 2H); 7.55 (1H); 7.82 (t, 1H); 7.92 (d, 1H); 8.13 (d, 1H); 8.78 (s, 1H). $^{13}$C (CDCl$_3$) δppm): 27.19 (d, $^4J_{CF}$=4.5), 30.20 (d, $^3J_{CF}$=19.5), 35.15 (d, $^2J_{CF}$=27.0), 67.94, 84.17 (d, $^1J_{CF}$=163.3), 116.93, 123.75, 127.26, 127.84, 128.82, 129.23, 129.42, 133.77, 135.62, 138.21, 140.54, 151.08, 154.59. $^{19}$F(CDCl$_3$, CFCl$_3$ internal standard) δ(ppm): −218.59 (t of t, J=−27.6, −50.4). Synthesis of Pyridaben Analogs:

EXAMPLE 2A

Synthesis of Butyric acid 4-phenylbutyl ester

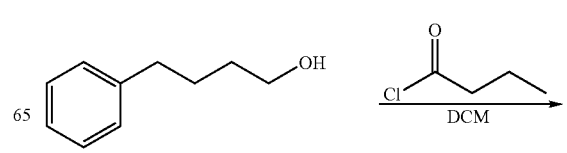

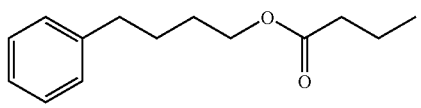

To 4-phenyl-1-butanol (7.0 g, 0.047 mol) was added anhydrous dichloromethane (20 mL). A solution of butyryl chloride (4.79 g, 0.045 mol) in anhydrous dichloromethane (20 mL) was added dropwise. The solution was stirred for 36 hours. At this point the reaction was concentrated under reduced pressure to give a crude oil. Column chromatography [silica gel; eluent hexanes-ethyl acetate (3:1)] provided the desired product (9.8 g, 94%) as a clear viscous liquid. $^1$H (CDCl$_3$) δ(ppm): 0.94 (t, 3H); 1.61-1.71 (m, 6H); 2.27 (t, 2H); 2.64 (t, 2H); 4.08 (t, 2H); 7.16-7.19 (m, 3H); 7.25-7.29 (m, 2H),

EXAMPLE 2B

Synthesis of 4-(4-Hydroxybutyl)benzoic acid methyl ester

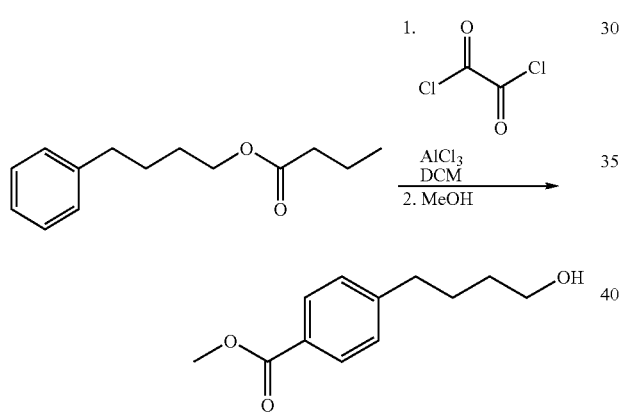

To aluminum chloride (6.7 g, 0.05 mol) in a dry 250 mL round bottom flask was added anhydrous dichloromethane (100 mL). The flask was cooled in a 0° C. ice bath. Oxalyl chloride (6.4 g, 0.05 mol) was added dropwise to the flask. The mixture was allowed to stir for 5 minutes. A solution of Example 2A (9.8 g, 0.044 mol) in anhydrous dichloromethane (50 mL) was then added dropwise. The mixture was allowed to stir for 4 hours at 0° C. The reaction mixture was poured into a separatory funnel containing ice and brine. The organic layer was washed with brine and dried over magnesium sulfate. Filtration and concentration under reduced pressure provided 9.1 g of yellow oil. 9.0 g of this oil was suspended in methanol and the pH adjusted to 2 and stirred for 48 hours. The reaction mixture was concentrated under reduced pressure. Column chromatography [silica gel; eluent hexanes-ethyl acetate (2.57:1)] provided the desired product (2.80 g, 31%) as a clear viscous liquid. $^1$H (CDCl$_3$) δ(ppm): 1.56-1.61 (m, 2H); 1.63-1.73 (m, 2H); 2.67 (t, 2H); 3.64 (t, 2H); 3.88 (s, 3H); 7.23 (d, 2H); 7.93 (d, 2H).

EXAMPLE 2C

Synthesis of 4-[4-(tert-Butyldimethylsilanyloxy)butyl]benzoic acid methyl ester

To Example 2B (1.0 g, 4.8 mmol) was added anhydrous dimethylformamide (10 mL), imidazole (0.5 g, 7.2 mmol) and tert-butyldimethylsilyl chloride (1.08 g, 7.3 mmol). The solution was stirred in a water bath for 2 hours. The reaction mixture was diluted with ethyl acetate, poured into a separatory funnel, washed with water (20 mL, 5×) then washed with a saturated sodium bicarbonate solution (20 mL, 2×). The organic layer was dried with magnesium sulfate, filtered, and concentrated under reduced pressure to give the desired product (1.17 g, 75%) which was used without further purification in the next step.

EXAMPLE 2D

Synthesis of {4-[4-(tert-Butyldimethylsilanyloxy)butyl]phenyl}-methanol

To Example 2C (1.17 g, 3.6 mmol) was added anhydrous diethyl ether (14 mL). The solution was cooled to 0° C. with an ice bath. Lithium aluminum hydride (0.28 g, 7.2 mmol) was added to the solution in portions. The mixture was stirred for 1 hour. To the reaction mixture was added distilled water (0.28 mL) and the mixture was stirred for 5 minutes. Next was added an aqueous 15% sodium hydroxide solution and the mixture was stirred for 5 minutes. Lastly distilled water (0.84 mL) was added and the mixture was stirred for 5 minutes. The white solid was removed by filtration. The filtrate was dried with magnesium sulfate, filtered, and concentrated to give 1.23 g of crude product. Column chromatography [silica gel;

EXAMPLE 2E

Synthesis of 2-tert-Butyl-5-{4-[4-(tert-butyldimethylsilanyloxy)butyl]benzyloxy}-4-chloro-2H-pyridazin-3-one

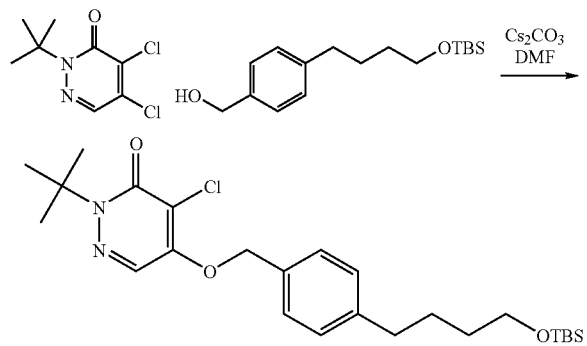

To a dry 25 mL round bottom flask, fitted with a reflux condenser, was added the product of Example 2D (0.41 g, 1.4 mmol), 2-tert-butyl-4,5-dichloro-2H-pyridazin-3-one (0.93 g, 4.2 mmol), cesium carbonate (1.37 g, 4.2 mmol), and anhydrous dimethylformamide (11 mL). The reaction flask was placed in a 68° C. oil bath and the reaction was stirred for 12 hours. The reaction flask was removed from the oil bath and allowed to cool. The mixture was diluted with ethyl acetate, transferred to a separatory funnel and washed with water (25 mL, 5×). The organic layer was dried with magnesium sulfate, filtered, and concentrated under reduced pressure to give 1.3 g of crude product. Column chromatography [silica gel; eluent hexanes-ethyl acetate (9:1)] provided the desired product (594 mg, 89%). $^1$H (CDCl$_3$) δ(ppm): 0.05 (s, 6H); 0.90 (s, 9H); 1.64 (s, 9H); 2.65 (t, 2H); 3.64 (t, 2H); 5.23 (s, 2H); 7.23 (d, 2H); 7.33 (d, 2H); 7.74 (s, 1H). $^{13}$C(CDCl$_3$) δ(ppm): 18.57, 26.19, 27.75, 28.09, 32.58, 35.61, 63.14, 66.57, 72.14, 118.46, 125.41, 127.44, 129.23, 132.38, 143.72, 154.02, 159.30.

EXAMPLE 2F

Synthesis of 2-tert-Butyl-4-chloro-5-[4-(4-hydroxybutyl)-benzyloxy]-2H-pyridazin-3-one

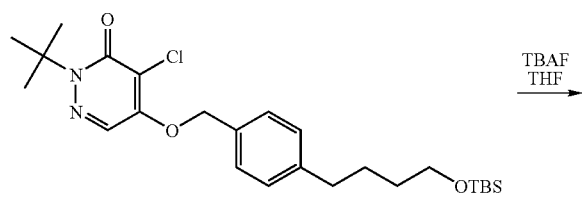

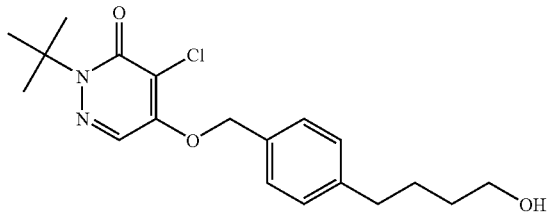

To the product of Example 2E (594 mg, 1.45 mmol) was added anhydrous tetrahydrofuran (3 mL) and a 1.0 M solution of tert-butylammonium fluoride in tetrahydrofuran (2.9 mL, 2.9 mmol). The solution was stirred for 1 hour then concentrated under reduced pressure. Column chromatography [silica gel; eluent pentane-ethyl acetate (1.8:1)] provided the desired product (410 mg, 77%). $^1$H (CDCl$_3$) δ(ppm): 1.61-1.64 (m, 11H); 1.67-1.74 (m, 2H); 2.68 (t, 2H); 3.68 (t, 2H); 5.23 (s, 2H); 7.23 (d, 2H); 7.33 (d, 2H); 7.74 (s, 1H). $^{13}$C (CDCl$_3$) δ(ppm): 27.43, 27.86, 32.56, 35.35, 62.74, 66.36, 71.88, 118.27, 125.18, 127.27, 128.99, 132.28, 143.17, 153.78, 159.07.

EXAMPLE 2G

Synthesis of Toluene-4-sulfonic acid 4-[4-(1-tert-butyl-5-chloro-6-oxo-1,6-dihydro-pyridazin-4-yloxymethyl)-phenyl]-butyl ester

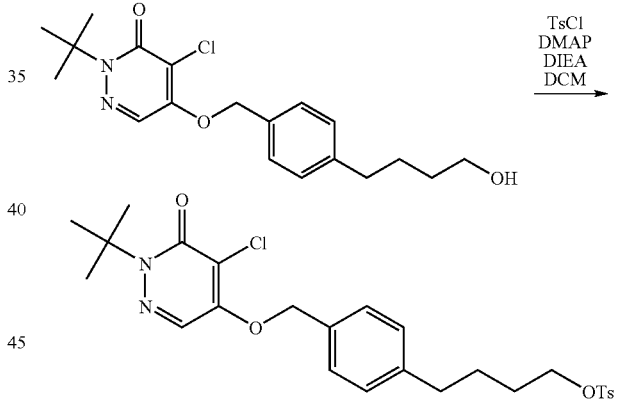

To a 5 mL round bottom flask was added the product of Example 2F (200 mg, 0.55 mmol), p-toluenesulfonyl chloride (125 mg, 0.66 mmol), 4-(dimethylamino)pyridine (80 mg, 0.66 mmol), diisopropylethylamine (85 mg, 0.66 mmol) and anhydrous dichloromethane (2 mL). The resulting solution was stirred for 2 hours. The reaction mixture was diluted with ethyl acetate, transferred to a separatory funnel and washed with a solution of aqueous 0.1 N hydrochloric acid and then washed with brine. The organic layer was dried with magnesium sulfate, filtered, and concentrated under reduced pressure to give 299 mg of crude product. Column chromatography [silica gel; eluent pentane-ethyl acetate (3:1)] provided the desired product (197 mg, 69%). $^1$H (CDCl$_3$) δ(ppm): 1.62-1.70 (m, 13H); 2.43 (s, 3H); 2.58 (t, 2H); 4.03 (t, 2H); 7.15 (d, 2H); 7.29-7.33 (m, 4H); 7.72 (s, 1H); 7.77 (d, 2H). $^{13}$C(CDCl$_3$) δ(ppm): 21.63, 26.98, 27.86, 28.34, 34.80, 66.37, 70.23, 71, 81, 118.25, 125.12, 127.32, 127.87, 128.93, 129.82, 132.48, 133.15, 142.40, 144.72, 153.75, 159.05.

EXAMPLE 2H

Synthesis of 2-tert-butyl-4-chloro-5-(4-(4-fluorobutyl)benzyl)oxy 3(2H) pyridazinone

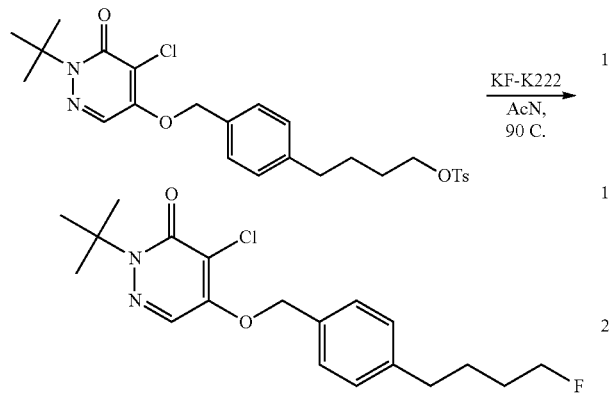

The product of Example 2G (57 mg, 0.10 mmol) was dissolved in 1 mL acetonitrile and to this was added a mixture of KF-K222 (1:1; 0.164 mmol) dissolved in 1 mL acetonitrile. The entire mixture was then immersed in an oil bath at 90° C. and heated at reflux for 15 minutes at which point the reaction was shown to be complete by TLC. The volatile components were removed in vacuo and the crude oil was purified by flash silica gel chromatography (hexanes-ethyl acetate (4:1)) to provide 28 mg of the desired product as a oil which solidified upon standing. $^1$H (CDCl$_3$) δ(ppm): 1.6 (s, 9H), 1.7 (m, 4H), 2.6 (t, 2H), 4.44 (d of t, 2H, J=47.4 & 6 Hz), 5.2 (s, 2H), 7.2 (d, 2H, J=8.4 Hz), 7.3 (d, 2H, J=8.4 Hz), 7.71 (s, 1H). $^{13}$C (CDCl$_3$) δ(ppm): 26.8 ($^3J_{CF}$=4.65 Hz), 27.8, 29.8 ($^2J_{CF}$=19.8 Hz), 35.1, 66.3, 71.8, 83.8 ($^1J_{CF}$=163.8 Hz), 118.2, 125.1, 127.2, 128.9, 132.3, 142.8, 153, 159. $^{19}$F(CDCl$_3$, CFCl$_3$ as internal standard) δ(ppm): −218.6 (t of t, J=−27.6, −50.4)

EXAMPLE 3A

Synthesis of (±)-1-tert-butyldimethylsilyloxy-2-hydroxybutane

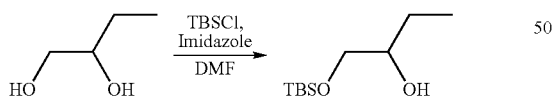

A 50 mL round bottom flask was charged with (±)-1,2-butanediol (1 g, 11.09 mmol) and to it was added dimethylformamide (8 mL) followed by tert-butyldimethylsilyl chloride (2.5 g, 16.64 mmol) and imidazole (1.88 g, 27.7 mmol). The reaction mixture was stirred for 10 hours after which it was diluted with dichloromethane and poured into a separatory funnel and washed with water (80 mL) and brine and dried over magnesium sulfate. After filtration and concentration the crude oil was purified by silica gel flash chromatography (hexanes:ethylacetate) to obtain 1 gm of pure desired product in 45% yield. $^1$H (CDCl$_3$) δ(ppm): 3.6 (m, 1H). 3.5 (m, 1H), 3.4 (m, 1H), 2.4 (s, 1H), 1.44 (m, 2H), 0.99 (t, 3H), 0.9 (s, 9H), 0.06 (s, 6H).

EXAMPLE 3B

Synthesis of (±)-4-(1-tertbutyldimethylsilyloxy but-2-oxy)methylbenzoate

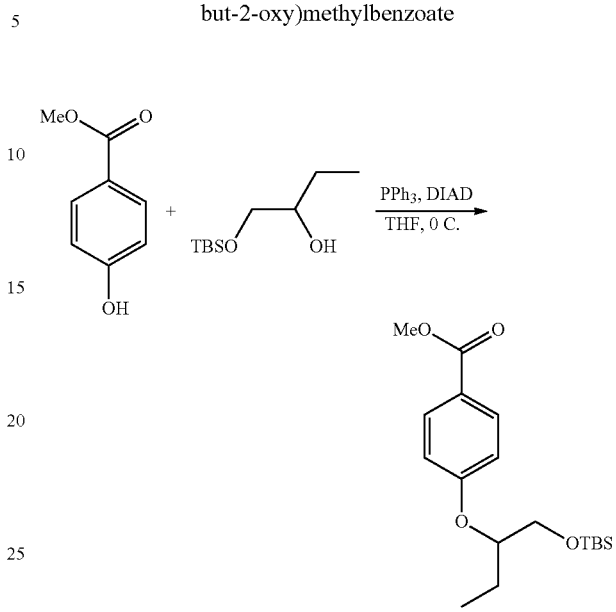

4-Hydroxymethylbenzoate (1.1 g, 7.34 mmol), the product of Example 3A (0.75 g, 3.67 mmol) and triphenylphosphine (1.972 g, 7.34 mmol) were added to a round bottom flask and 8 mL tetrahydrofuran was added. The flask was cooled in an ice bath to 0° C. after which diisopropylazodicarboxylate (1.485 g, 7.34 mmol) was added via syringe. The reaction mixture was stirred for 2 hours after which the reaction was deemed complete by thin layer chromatography. All the solvent was removed under reduced pressure and the crude oil directly subjected to purification by silica gel flash chromatography (hexanes: diethyl ether) to obtain 1.0 gm (83%) of the desired compound as a thick oil. $^1$H (CDCl$_3$) δ(ppm): 7.9 (d, 2H), 6.9 (d, 2H), 4.3 (p, 1H, J=5.4 Hz), 3.9 (s, 3H), 3.7 (2H), 1.78 (m, 1H), 1.7 (m, 1H), 0.9 (t, 3H), J=7.8 Hz), 0.89 (s, 9H), 0.05 (s, 3H), 0.01 (s, 3H). $^{13}$C(CDCl$_3$) δ (ppm): 166.8, 162.8, 131.5, 122.3, 115.2, 80, 64.5, 51.7, 25.8, 24.1, 18.2, 9.5, −5.3.

EXAMPLE 3C

Synthesis of (±)-4-(1-tertbutyldimethylsilyloxy but-2-oxy)benzylalcohol

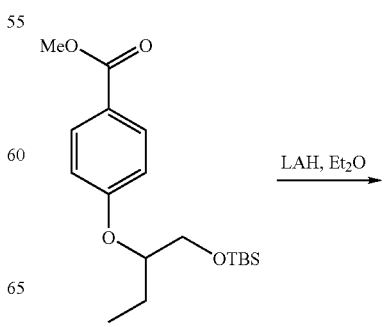

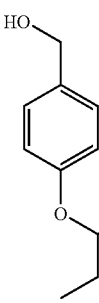

To a solution of the product of Example 3B (1 g, 2.95 mmol) in ether (15 mL) was added lithium aluminum hydride (0.336 g, 8.8 mmol) and the mixture was stirred under nitrogen for 1.5 hours. The reaction was complete as shown by TLC by this time and was quenched by addition of 0.336 mL water, 0.336 mL of 15% NaOH solution and 1.00 mL water in succession. The resulting mixture was stirred for an additional 20 minutes after which the white precipitate formed was filtered and washed with ether. The filtrate was then dried over magnesium sulfate. Filtration and removal of the solvent gave 0.50 g (54%) of the desired product as a white solid. $^1$H (CDCl$_3$) δ (ppm): 7.2 (d, 2H), 6.9 (d, 2H), 4.3 (p, 1H), 3.77 (d of d, 1H), 3.66 (d of d, 1H), 1.77-1.72 (m, 1H), 1.68-1.61 (m, 1H), 1.5 (t, 1H, J=5.4 Hz), 0.9 (t, 3H, J=7.8 Hz), 0.89 (s, 9H), 0.04 (s, 3H), 0.01 (s, 3H). $^{13}$C (CDCl$_3$) δ (ppm): 158.5, 133, 128.4, 116.1, 80.1, 65, 64.5, 25.8, 24.1, 18.2, 9.5, −5.3

EXAMPLE 3D

Synthesis of (±)-2-tert-butyl 4-chloro-5-(4-(1-tertbutyldimethylsilyloxy but-2-oxy)benzyl)oxy 3(2H)-pyridazinone

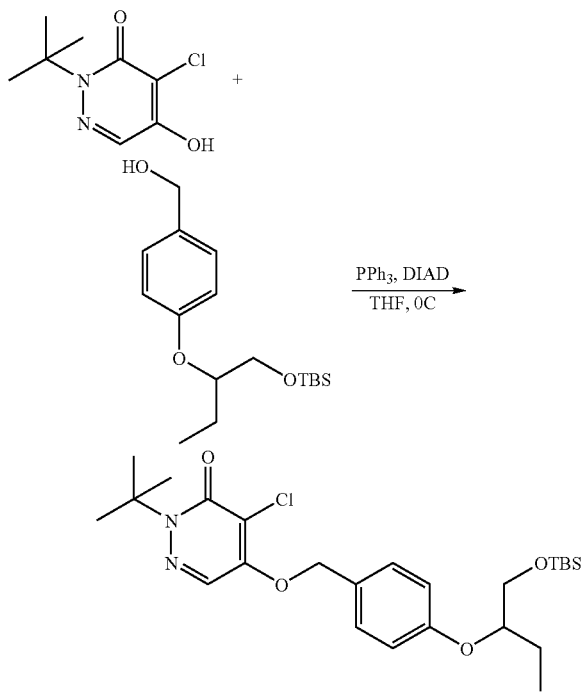

(±)-2-Tert-butyl-4-chloro-5-hydroxy-3(2H)-pyridazinone (0.48 g, 2.417 mmol) was charged to a 100 mL round bottom flask and tetrahydrofuran (40 ml) was added. After the solution turned clear, Example 3C (0.5 g, 1.611 mmol) and triphenylphosphine (0.633 g, 2.417 mmol) were added to the flask and the flask was cooled to 0° C. Diisopropyl azodicarboxylate (0.488 g, 2.417 mmol, 0.468 mL) was then added via a syringe and the reaction was stirred for two hours after which time it was shown to be complete by TLC. The contents of the flask were then concentrated in vacuo and the crude oil obtained was purified by flash chromatography using silica gel (hexanes:ethyl acetate) to obtain 0.33 g of the desired compound as an oil. $^1$H (CDCl$_3$) δ (ppm): 7.72 (s, 1H), 7.2 (d, 2H), 6.9 (d, 2H), 5.2 (s, 2H), 4.2 (p, 1H), 3.75 (d of d, 1H), 3.68 (d of d, 1H), 1.75 (m, 2H), 1.65 (m, 1H), 1.6 (s, 9H), 0.99 (t, 3H), 0.85 (s, 9H), 0.04 (s, 3H), 0.02 (s, 3H). $^{13}$C (CDCl$_3$) δ (ppm): 159.6, 159.3, 154, 129, 126.9, 125, 118.5, 116.5, 80.3, 72.1, 66.5, 64.8, 28.1, 26, 24.4, 18.4, 9.6, −5.3

EXAMPLE 3E

Synthesis of (±)-2-tert-butyl-4-chloro-5-(4-(1-hydroxy-but-2-oxy)benzyl)oxy-3(2H)-pyridazinone

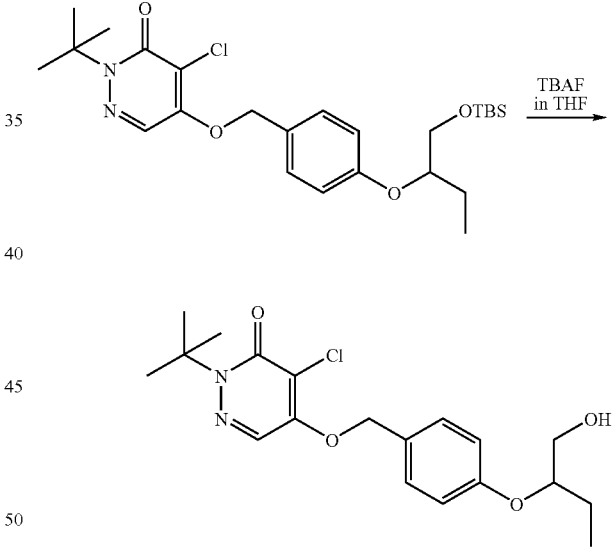

To the product of Example 3D (0.3 g, 0.6 mmol) in a 10 mL round bottom flask was added tetrahydrofuran (2 mL). Upon solution, tetrabutylammonium fluoride (1.8 mmol, 1.8 mL, 1 M solution in THF) was added and the reaction mixture was stirred for 90 minutes. The contents were then concentrated under reduced pressure and the crude mixture purified by flash chromatography using silica gel (hexanes:ethyl acetate) to obtain 185 mg (80%) of pure desired product. $^1$H (CDCl$_3$) δ (ppm): 7.74 (s, 1H), 7.3 (d, 2H), 6.9 (d, 2H), 5.2 (s, 2H), 4.3 (m, 1H), 3.81-3.77 (two br s, 2H), 1.84 (hr t, 1H), 1.77-1.69 (m, 2H), 1.64 (s, 9H), 0.98 (t, 3H); $^{13}$C (CDCl$_3$) δ (ppm): 159.2, 158.9, 153.9, 129.2, 127.5, 125.4, 116.6, 80.4, 71.9, 66.5, 64.2, 28, 23.5, 9.7.

EXAMPLE 3F

Synthesis of (±)-2-tert-butyl 4-chloro 5-(4-(1-tosyloxy-but-2-oxy)benzyl)oxy 3(2H)-pyridazinone

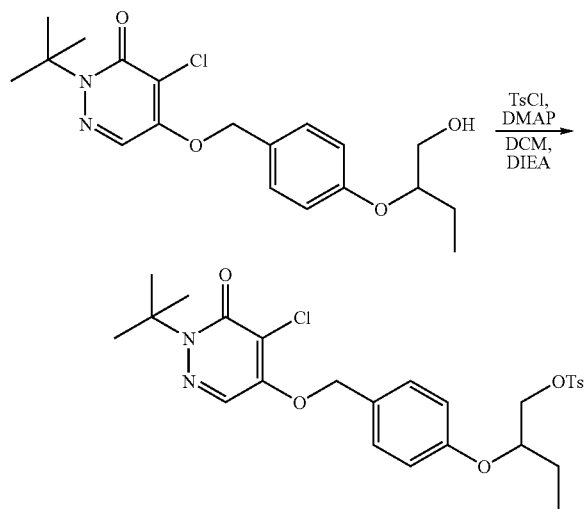

Into a 10 mL round bottom flask was added the product of Example 3E (0.05 g, 0.13 mmol) followed by dichloromethane (2 mL). Toluenesulfonyl chloride (0.075 g, 0.39 mmol), 4-N,N-dimethylaminopyridine (0.048 g, 0.39 mmol) and diisopropylethylamine (0.05 g, 0.39 mmol, 68.7 µl) were then added in succession to the reaction mixture and this was stirred for 35 minutes. Water was then added to the mixture and the solution poured into a separatory funnel and the layers separated. The organic layer was washed with water and brine and dried over magnesium sulfate. The crude oil obtained after filtration and concentration was purified by silica gel flash chromatography (hexanes:ethyl acetate) to obtain 54 mg (77%) of the desired compound as a thick colorless oil. $^1$H (CDCl$_3$) δ (ppm): 7.74 (3H, two singlets), 7.3 (m, 4H), 6.8 (d, 2H), 5.2 (s, 2H), 4.38 (p, 1H), 4.15 (m, 2H), 2.44 (s, 3H), 1.72 (m, 2H), 1.6 (s, 9H), 0.95 (t, 3H); $^{13}$C (CDCl$_3$) δ (ppm): 159.2, 158.5, 153.9, 145.1, 133, 130, 129, 128.1, 127.2, 125.4, 118.5, 116.5, 71.9, 70.2, 66.6, 28.1, 24.2, 21.8, 9.4.

EXAMPLE 3G

Synthesis of (±)-2-tert-butyl-4-chloro 5-(4-(1-fluoro-but-2-oxy)benzyl)oxy-3(2H)-pyridazinone

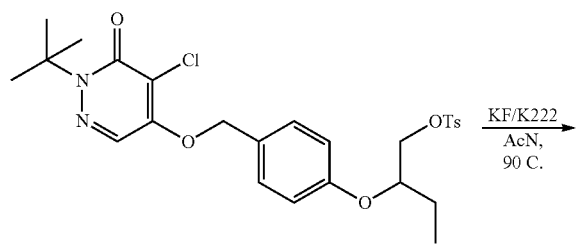

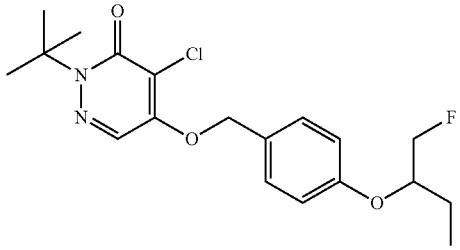

The product of Example 3F (28 mg, 52.4 µmol) was dissolved in 0.5 mL acetonitrile in a 5 mL flask and to this was added a solution of potassium fluoride (4.5 mg, 78.6 µmol) and Kryptofix 222 (29.6 mg, 78.6 µmol) in 0.5 mL acetonitrile. The above solution was then immersed in a oil bath preheated to 90° C. The reaction was allowed to stir for 90 minutes after which all the volatiles were removed under reduced pressure and the crude mixture purified by preparative thin layer chromatography to obtain 13 mg (65%) of pure desired compound. $^1$H (CDCl$_3$) δ (ppm): 7.72 (s, 1H), 7.3 (d, 2H), 6.9 (d, 2H), 5.23 (s, 2H), 4.57-4.59 (m, 2H), 4.4 (m, 4H), 1.74 (m, 2H), 1.6 (s, 9H), 1.0 (t, 3H). $^{13}$C (CDCl$_3$) δ (ppm): 159, 158.7, 153.7, 129, 127.5, 125.2, 118.3, 116.4, 83.85 (d, $^1J_{CF}$=172.2), 78, 71.1, 66.3, 27.8, 23.2, 9.48. $^{19}$F (CDCl$_3$, CFCl$_3$ as internal standard) δ (ppm): −228 (d of t, J=−19, −60 Hz)

EXAMPLE 4A

Synthesis of 4-(3-hydroxypropoxy)-benzoic acid methyl ester

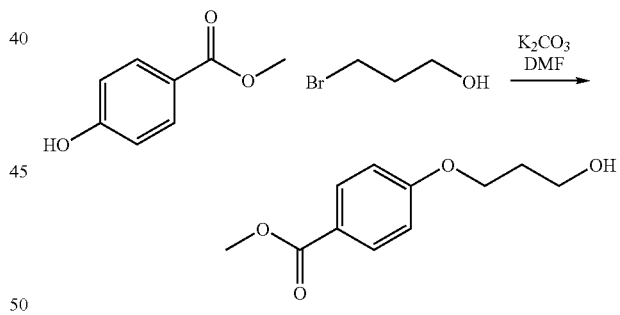

To a 250 mL flask was added 3-bromo-1-propanol (4.17 g, 0.03 mol), anhydrous dimethylformamide (40 mL), methyl-4-hydroxybenzoate (3.0 g, 0.02 mol) and potassium carbonate (4.15 g, 0.03 mol). The flask was placed in a 50° C. oil bath and stirred for 12 hours. After cooling the reaction was diluted with ethyl acetate, transferred to separatory funnel, washed with aqueous 0.1 N hydrochloric acid, water then brine. The organic layer was dried with magnesium sulfate, filtered, and concentrated under reduced pressure to give 5.14 g of crude oil. Column chromatography [silica gel; eluent hexanes-ethyl acetate (1.68:1)] provided the desired product (1.25 g, 30%) as a white powder. $^1$H (CDCl$_3$) δ(ppm): 2.04-2.08 (m, 2H); 3.86-3.88 (m, 5H); 4.17 (t, 2H); 6.91 (d, 2H); 7.98 (d, 2H); $^{13}$C (CDCl$_3$) δ(ppm): 31.89, 51.81, 59.88, 65.50, 114.06, 122.67, 131.57, 162.60, 166.84.

EXAMPLE 4B

Synthesis of 4-[3-(tert-Butyldimethylsilanyloxy)propoxy]benzoic acid methyl ester

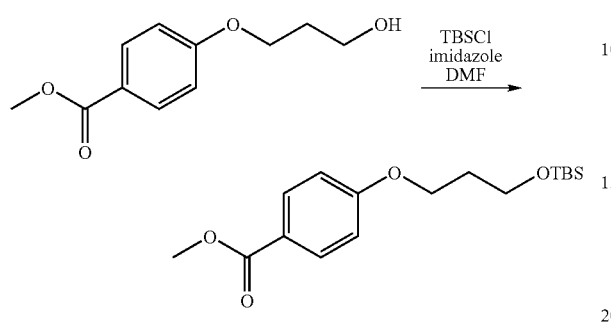

To a 50 mL flask was added Example 4A (300 mg, 1.4 mmol), anhydrous dimethylformamide (4 mL), tert-butyldimethylsilyl chloride (317 mg, 2.1 mmol), and imidazole (146 mg, 2.1 mmol). The resulting solution was stirred for 2 hours. At this point the reaction was diluted with ethyl acetate and transferred to a separatory funnel. The organic phase was washed with aqueous 0.1 N hydrochloric acid (2×), water (2×), then brine. The organic layer was then dried over magnesium sulfate, filtered, and concentrated. Column chromatography [silica gel; eluent hexanes-ethyl acetate (9.5:1)] provided the desired product (413 mg, 91%). $^1$H (CDCl$_3$) δ (ppm): 0.03 (s, 6H); 0.87 (s, 9H); 1.97-2.01 (m, 2H); 3.79 (t, 2H); 3.87 (s, 3H); 4.11 (t, 2H); 6.90 (d, 2H); 7.97 (d, 2H); $^{13}$C (CDCl$_3$) δ(ppm): 18.30, 25.89, 32.3, 51.78, 59.27, 64.67, 114.08, 122.43, 131.56, 162.90, 166.90

EXAMPLE 4C

Synthesis of {4-[3-(tert-Butyldimethylsilanyloxy)propoxy]phenyl}methanol ether

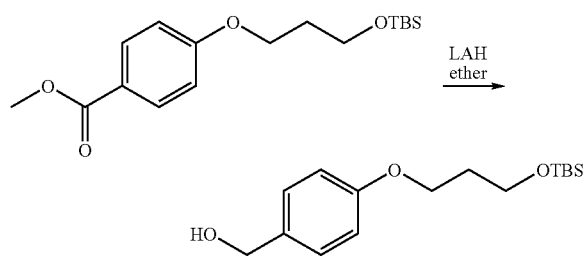

Example 4B (396 mg, 1.22 mmol) was added to a dry 50 mL flask along with anhydrous diethyl ether (10 mL). The flask was lowered into an ice bath. Lithium aluminum hydride (93 mg, 2.44 mmol) was added in portions to the reaction flask. The mixture was allowed to stir in the bath for 2 hours. The reaction was quenched with water (0.093 mL), aqueous 15% sodium hydroxide (0.093 mL) then water (0.279 mL). The white solid was filtered off and the filtrate was dried over magnesium sulfate, filtered, and concentrated to give the desired product (291 mg, 80%). $^1$H (CDCl$_3$) δ(ppm): 0.04 (s, 6H); 0.88 (s, 9H); 1.95-1.99 (m, 2H); 3.79 (t, 2H); 4.05 (t, 2H); 4.60 (s, 2H); 6.88-6.89 (m, 2H); 7.25-7.27 (m, 2H); (CDCl$_3$) δ(ppm): 18.30, 25.91, 32.41, 59.50, 64.57, 65.10, 114.59, 128.60, 132.97, 158.75.

EXAMPLE 4D

Synthesis of 2-tert-butyl-4-chloro-5-{4-[3-(tert-butyldimethylsilanyloxy)propoxy]benzyloxy}-2H-pyridazin-3-one

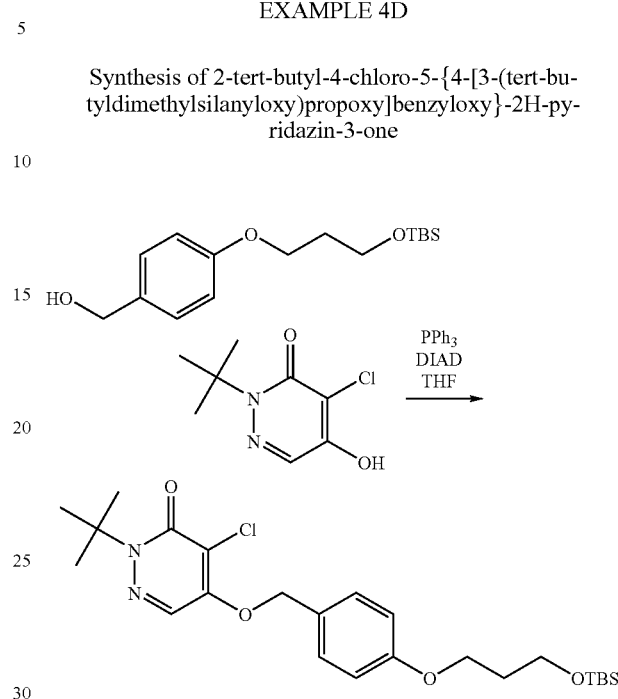

To a dry 25 mL flask was added Example 4C (211 mg, 0.71 mmol) and anhydrous tetrahydrofuran (3 mL). The flask was cooled in an ice bath. To the flask was added triphenylphosphine (187 mg, 0.71 mmol) and 2-tert-butyl-4-chloro-5-hydroxy-2H-pyridazin-3-one (142 mg, 0.71 mmol). Lastly, diisopropyl azodicarboxylate (144 mg, 0.71 mmol) was added. The reaction mixture was allowed to stir in the ice bath for 1 hour. At this point the mixture was diluted with diethyl ether and transferred to a separatory funnel. The organic solution was washed with water and then brine, dried over magnesium sulfate, filtered, and concentrated under reduced pressure. Column chromatography [silica gel; eluent hexanes-ethyl:acetate (9:1)] provided the desired product (106 mg, 31%). $^1$H (CDCl$_3$) δ(ppm): 0.03 (s, 6H); 0.87 (s, 9H); 1.62 (s, 9H); 1.95-1.99 (m, 2H); 3.79 (t, 2H); 4.06 (t, 2H); 5.23 (s, 2H); 6.91-6.92 (m, 2H); 7.30-7.31 (m, 2H); 7.72 (s, 1); $^{13}$C (CDCl$_3$) δ(ppm): 18.29, 25.90, 27.87, 32.34, 59.41, 64.63, 66.30, 71.89, 114.90, 118.34, 125.34, 126.68, 128.92, 153.79, 159.07, 159.55

EXAMPLE 4E

Synthesis of 2-tert-butyl-4-chloro-5-[4-(3-hydroxypropoxy)-benzyloxy]-2H-pyridazin-3-one

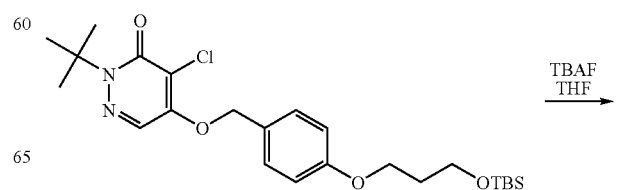

-continued

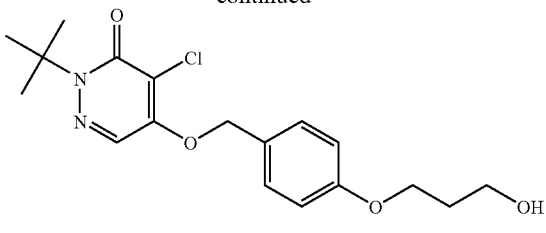

To a dry 10 mL flask was added Example 4D (100 mg, 0.21 mmol) along with anhydrous tetrahydrofuran (2 mL). To the flask was added a solution of 1.0 M tetrabutylammonium fluoride in tetrahydrofuran (0.42 mL, 0.42 mmol). The solution was stirred for 2 hours. At this point the reaction was concentrated under reduced pressure. Preparatory thin layer chromatography [silica gel; eluent hexanes-ethyl:acetate (1:1)] provided the desired product (57.8 mg, 76%). $^1$H (CDCl$_3$) δ (ppm): 1.62 (s, 9H); 2.02-2.06 (m, 2H); 3.86 (t, 2H); 4.13 (t, 2H); 5.30 (s, 2H); 6.92-6.93 (m, 2H); 7.31-7.32 (m, 2H); 7.71 (s, 1H); $^{13}$C (CDCl$_3$) δ ppm): 27.87, 31.97, 60.24, 65.67, 66.34, 71.81, 114.91, 118.37, 125.31, 127.06, 128.98, 153.76, 159.07, 159.27.

EXAMPLE 4F

Synthesis of toluene-4-sulfonic acid 3-[4-(1-tert-butyl-5-chloro-6-oxo-1,6-dihydro-pyridazin-4-yloxymethyl)phenoxy]propyl ester

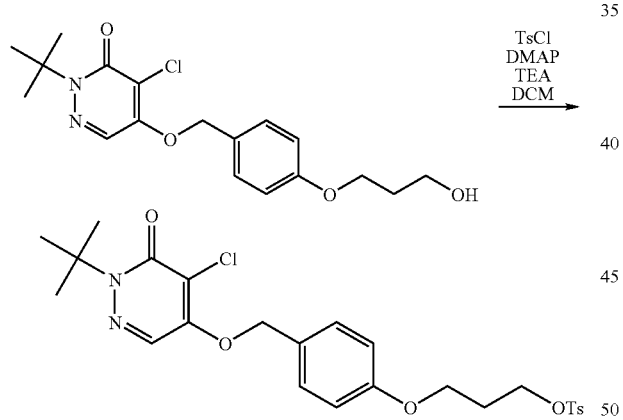

To a dry 5 mL flask was added Example 4E (40 mg, 0.11 mmol), 4-methyl-benzenesulfonyl chloride (31 mg, 0.16 mmol), 4-(dimethylamino)pyridine (20 mg, 0.16 mmol), diisopropylethylamine (16.6 mg, 0.16 mmol) and anhydrous dichloromethane (0.6 mL). The resulting solution was stirred for 1 hour. The reaction mixture was concentrated under reduced pressure. Preparatory thin layer chromatography [silica gel; eluent pentane-ethyl acetate (3:2)] provided the desired product (18.6 mg, 33%). $^1$H (CDCl$_3$) δ(ppm): 1.62 (s, 9H); 2.09-2.13 (m, 2H); 2.37 (s, 3H); 3.95 (t, 2H); 4.23 (t, 2H); 5.22 (s, 2H); 6.78 (d, 2H); 7.23 (d, 2H); 7.29 (d, 2H); 7.73-7.75 (m, 3H). $^{13}$C (CDCl$_3$) δ ppm): 21.60, 27.85, 28.81, 63.15, 66.35, 66.87, 71.75, 114.76, 118.27, 125.18, 127.11, 127.83, 128.94, 129.80, 132.79, 144.80, 163.72, 158.90, 159.03.

EXAMPLE 4G

Synthesis of 2-tert-butyl-4-chloro-5-[4-(3-fluoropropoxy)benzyloxy]-2H-pyridazin-3-one

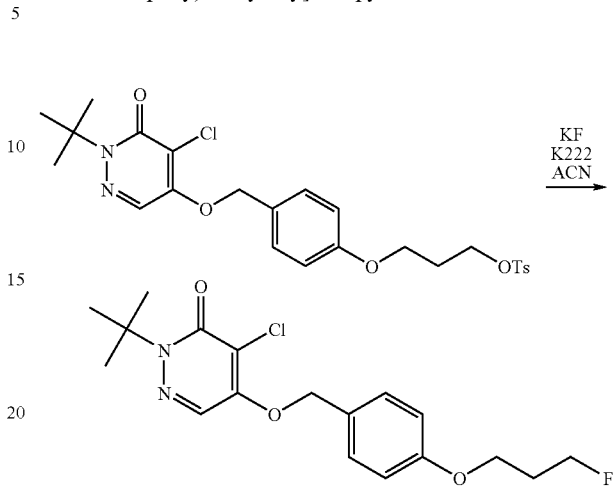

To a scintillation vial containing a suspension of Example 4F (4.5 mg, 8.64×10$^{-3}$ mmol) in anhydrous acetonitrile (0.25 mL) was added a solution of potassium fluoride (1.6 mg, 4.07×10$^{-2}$ mmol) and kryptofix (15.0 mg, 4.07×10$^{-2}$ mmol) in anhydrous acetonitrile (0.25 mL). The vial was capped and lowered into a 90° C. oil bath. The reaction was allowed to stir for 40 minutes. The reaction was cooled and concentrated under reduced pressure. Preparatory thin layer chromatography [silica gel; eluent pentane-ethyl acetate (3:2)] provided the desired product (0.8 mg, 25%). $^1$H (CDCl$_3$) δ(ppm): 1.62 (s, 9H); 2.14-2.20 (m, 2H); 4.09-4.11 (m, 2H); 4.60 (t, 1H); 4.68 (t, 1H); 5.24 (s, 2H); 6.92 (d, 2H); 7.32 (d, 2H); 7.72 (s, 1H); $^{19}$F(CDCl$_3$, CFCl$_3$ as internal standard) δ(ppm): −222.66 (t of t, J=28.2, −50.4)

EXAMPLE 5A

Synthesis of 4-(2-hydroxyethoxymethyl)benzoic acid methyl ester

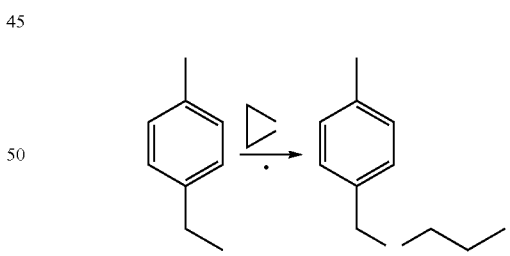

Ethylene oxide (1.10 mL) was added to the cooled stirring solution dropwise followed by the addition of boron trifluoride etherate (0.51 ml). The reaction mixture was stirred for 45 minutes and then warmed to room temperature for 30 minutes to boil off any excess of ethylene oxide in the reaction mixture. The reaction mixture was then diluted with brine. The aqueous layer was extracted with dichloromethane (3 times). All of the organic layers were combined, dried over Na$_2$SO$_4$, filtered, and concentrated to provide an oil. The crude material was purified using silica gel:chromatography (4:1 pentane:ethyl acetate) to provide the desired product (537 mg, 2.56 mmol) in 17% yield. $^1$H (CDCl$_3$ δ.36, 600

Mhz): δ (2H, d, J=8.4 Hz), 7.41 (2H, d, J=8.5 Hz), 4.62 (3H, s), 3.92 (2H, s), 3.78 (m, 2H), 3.63 (2H, m); $^{13}C$ (CDCl$_3$ 167.1, 143.5, 130.0, 129.8, 127.5, 72.9, 72.0, 150 MHz): δ 62.1, 52.3.

EXAMPLE 5B

Synthesis of 4-[2-(tert-butyldimethylsilanyloxy)ethoxymethyl]benzoic acid methyl ester

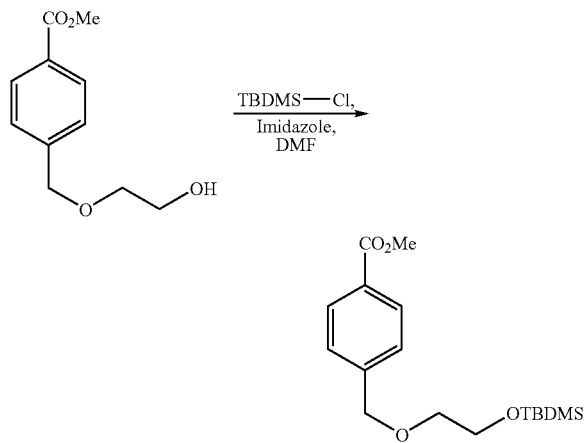

To a solution of the product of Example 5A (544.5 mg, 2.59 mmol) in anhydrous DMF (26 mL) was added imidazole (264 mg, 3.89 mmol) and TBDMS-Cl (586 mg, 3.89 mmol). The reaction mixture stirred at room temperature overnight and was quenched with water. The aqueous layer was extracted with ethyl acetate (3×). All combined organic layers were dried over Na$_2$SO$_4$, filtered, and concentrated. The crude material was purified using silica gel chromatography (4:1 pentane:ethyl acetate) to provide the desired product (677.5 mg, 2.19 mmol) in 84% yield. $^1H$ (CDCl$_3$ 8.01, 600 MHz): δ (2H, d, J=8.3 Hz), 7.42 (2H, d, J=8.4 Hz), 4.63 (2H, s), 3.91 (2H, s), 3.82 (2H, t, J=5.0), 3.58 (2H, t, J=5.1 Hz), 0.91 (9H, s), 0.07 (6H, s); $^{13}C$(CDCl$_3$ 166.5, 143.5, 129.2, 128.8, 126.5, 72.1, 71.6, 150 MHz): δ 62.3, 51.5, 25.4, 17.9, −5.8.

EXAMPLE 5C

Synthesis of {4-[2-(tert-butyldimethylsilanyloxy)ethoxymethyl]phenyl}methanol

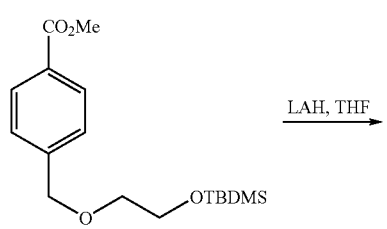

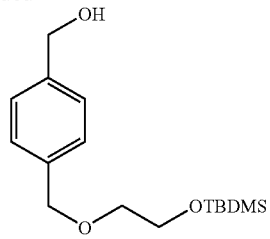

To a solution of the product of Example 5B (670 mg, 2.18 mmol) dissolved in anhydrous THF (22 mL) was added a solution of LAH (1.0 M solution in THF, 2.18 mL, 2.18 mmol) dropwise. After completion of addition the reaction mixture was stirred at room temperature for 3 hours. The reaction mixture was diluted with water. The aqueous layer was extracted with ethyl acetate (3×). All combined organic layers were dried over Na$_2$SO$_4$, filtered, and concentrated to provide an oil (587 mg, 1.98 mmol), which was used in the next step without any further purification (91% yield). $^1H$ (CDCl$_3$ 7.34 (4H, s), 4.68 (2H, s), 4.57 (2H, s), 3.80, 600 MHz): δ (2H, t, J=5.2 Hz), 3.56 (21H, t, J=5.3 Hz), 1.69 (1H, br s), 0.90 (9H, s), 0.07 (6H, s); $^{13}C$(CDCl$_3$ 140.4, 138.3, 128.0, 127.2, 73.2, 71.9, 65.4, 150 MHz): δ 63.0, 26.2, 18.6, −5.0.

EXAMPLE 5D

Synthesis of 2-tert-butyl-5-{4-[2-(tert-boutyldimethylsilanyloxyethoxymethyl]benzyloxy}-4-chloro-2H-pyridazin-3-one To solution of the product of Example 5C (437 mg, 1.48 mmol) and 2-tert-butyl-4-chloro-5-hydroxy-2H-pyridazin-3-one (250 mg, 1.23 mmol) dissolved in anhydrous THF (12 mL) was added solid PPh$_3$ (485 mg, 1.85 mmol) and diisopropyl azodicarboxylate (DIAD, 0.358 mL, 1.85 mmol). After completion of addition the reaction mixture continued to stir at room temperature. After 20 hours, the reaction mixture was diluted with water. The aqueous layer was separated and extracted with ethyl acetate (3×). All combined organic layers were dried over Na$_2$SO$_4$, filtered, and concentrated to provide an oil. The crude material was purified using silica gel (4:1 pentane:ethyl acetate) to provide the desired product 528 mg, 1.10 mmol) in 89% yield. $^1H$ (CDCl$_3$ 7.70 (1H, s), 7.38

(4H, m), 5.30 (2H, s), 4.58, 600 MHz): δ (2H, s), 3.80 (2H, t, J=5.4 Hz), 3.57 (2H, t, J=5.4 Hz), 1.63 (9H, br s), 0.90 (9H, s), 0.07 (6H, s); $^{13}$C(CDCl$_3$159.0, 153.7, 138.8, 134.4, 128.3, 127.3, 150 MHz): δ 125.1, 118.5, 72.8, 71.7, 71.6, 66.4, 61.9, 29.7, 27.9, 25.6, −5.1; HRMS calcd for C$_{24}$H$_{37}$ClN$_2$O$_4$Si: 481.228389, found 481.2282.

EXAMPLE 5E

Synthesis of 2-tert-butyl-4-chloro-5-[4-(2-hydroxy-ethoxymethyl)benzyloxy]-2H-pyridazin-3-one

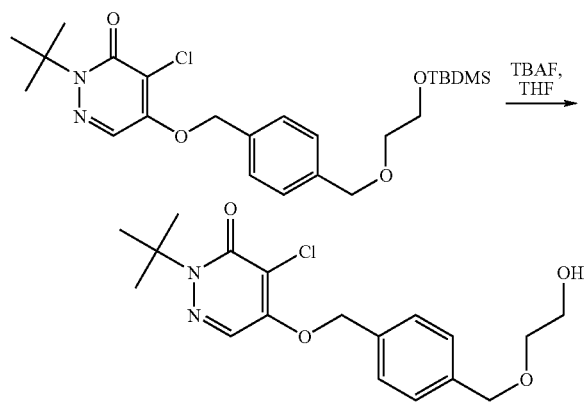

To a solution of the product of Example 5D (528 mg, 1.09 mmol) dissolved in anhydrous THF (11 mL) was added a solution of TBAF (1.0 M solution in THF, 1.65 mL, 1.65 mmol) dropwise. After completion of addition the reaction was stirred at room temperature for 1 hour and then quenched with water. The aqueous layer was separated and extracted with ethyl acetate (3×). All combined organic layers were dried over Na$_2$SO$_4$, filtered, and concentrated to provide an oil. The crude material was purified using silica gel chromatography (4:1 hexanes:ethyl acetate) to provide the desired product (311 mg, 0.850 mmol) in 78% yield. $^1$H (CDCl$_3$, 600 MHz): δ 7.70 (1H, s), 7.38 (4H, m), 5.30 (2H, s), 4.56 (2H, s), 3.76 (2H, t, J=4.9 Hz), 3.60 (2H, t, J=4.8 Hz), 2.00 (1H, br s), 1.61 (9H, br s); $^{13}$C (CDCl$_3$159.0, 153.6, 150 MHz): δ 138.8, 134.4, 128.2, 127.2, 125.1, 118.3, 72.8, 71.6, 71.6, 66.4, 61.9, 27.8; HRMS calcd for C$_{18}$H$_{23}$ClN$_2$O$_4$: 367.141911, found 367.1419.

EXAMPLE 5F

Synthesis of toluene-4-sulfonic acid 2-[4-(1-tert-butyl-5-chloro-6-oxo-1,6-dihydro-pyridazin-4-yloxymethyl)-benzyloxy]-ethyl ester

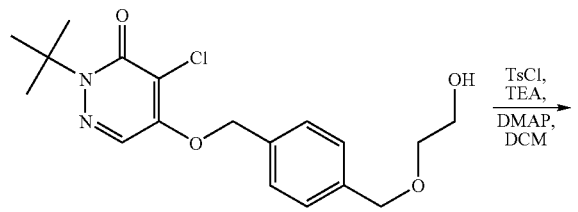

-continued

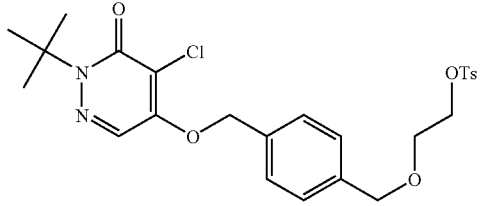

To a solution of the product of Example 5E (200 mg, 0.546 mmol) dissolved in anhydrous dichloromethane (5.50 mL) was added TsCl (125 mg, 0.656 mmol), DMAP (100 mg, 0.819 mmol) and triethylamine (0.091 mL, 0.656 mmol). The reaction mixture continued stirring at room temperature. After 22 hours the reaction mixture was diluted with water. The aqueous layer was separated and extracted with ethyl acetate (3×). All combined organic layers were dried over Na$_2$SO$_4$, filtered, and concentrated to provide an oil. The crude material was purified using silica gel:chromatography (3:2 pentane:ethyl acetate) to provide the desired product (232 mg, 0.447 mmol) in 82% yield. $^1$H (CDCl$_3$7.79, 600 MHz): δ (2H, d, J=8.3 Hz), 7.71 (1H, s), 7.38 (2H, d, J=8.2 Hz), 7.32 (4H, m), 5.30 (2H, s), 4.50 (2H, s), 4.21 (2H, m), 3.69 (2H, m), 2.43 (3H, s), 1.63 (9H, br s); $^{13}$C (CDCl$_3$ 159.0, 153.7, 144.8, 138.8, 150 MHz): δ 134.4, 133.1, 129.8, 128.1, 128.0, 127.2, 125.1, 118.4, 72.8, 71.7, 69.2, 67.8, 66.4, 27.9, 21.6; HRMS calcd for C$_{25}$H$_{29}$ClN$_2$O$_6$: 521.150762, found 521.1503.

EXAMPLE 5G

Synthesis of 2-tert-butyl-4-chloro-5-[4-(2-fluoro-ethoxymethyl)-benzyloy]-2H-pyridazin-3-one

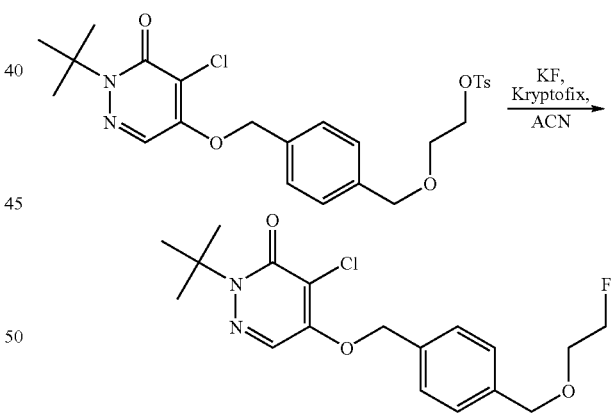

To a solution of the product of Example 5F (50 mg, 0.096 mmol) in anhydrous acetonitrile (1.0 mL) was added KF (11.2 mg, 0.192 mmol) and Kryptofix (72.4 mg, 0.192 mmol). After completion of addition the reaction mixture was heated to 90° C. After 10 minutes, the reaction mixture was cooled down to room temperature and diluted with water. The aqueous layer was separated and extracted with ethyl acetate (3×). All combined organic layers were dried over Na$_2$SO$_4$, filtered, and concentrated to provide an oil. The crude material was purified using silica gel chromatography (4:1 pentane: ethyl acetate) to provide the desired product (28 mg, 0.076 mmol) in 79% yield $^1$H (DMSO-d$_6$, 600 MHz): δ 8.22 (1H, s), 7.45 (2H, d, J=8.20 Hz), 7.39 (2H, d, J=8.24 Hz), 5.42 (2H, s), 4.60 (1H, m), 4.54 (2H, s), 4.52 (1H, m), 3.71 (1H, m), 3.66 (1H, m), 1.57 (9H, s); [13]157.8, 153.8, 138.6, C (DMSO-d6, 150 MHz): δ 134.6, 127.8, 127.7, 126.2, 115.6, 83.5 (82.4), 71.6, 71.2, 69.1(69.0), 65.3, 27.4; [19]F (DMSO-$d_6$-221.74 (1F, m), 564 MHz): δ HRMS calcd for $C_{18}H_{22}ClFN_2O_3$: 369.137575, found 369.1377.

EXAMPLE 6A

Synthesis of 1-(4-hydroxymethylphenoxy)propan-2-one

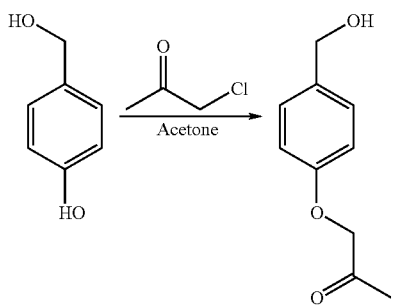

To a stirred solution of 4-hydroxybenzyl alcohol (1.0 g, 8.06 mmol) in acetone (80 mL) was added potassium carbonate (1.34 g, 9.68 mmol) and chloroacetone (0.771 mL, 9.68 mmol). After completion of addition the reaction mixture was heated to reflux. After 20 hours the reaction mixture was cooled down to room temperature and the solvent was removed. Water and ethyl acetate were added to the crude material. The aqueous layer was separated and extracted with ethyl acetate (3×, 100 mL). All combined organic layers were dried over $Na_2SO_4$, filtered, and concentrated to provide an oil. The crude material was purified using silica gel chromatography (gradient from 4:1 to 1:1 pentane:ethyl acetate) to provide the desired product (0.981 g, 5.45 mmol) in 98% yield. [1]H (CDCl$_3$, 600 MHz): δ 7.30 (2H, d, J=8.7 Hz), 6.87 (2H, d, J=8.7 Hz), 4.63 (2H, d, J=5.7 Hz), 4.54 (2H, s), 2.27 (3H, s), 1.66 (1H, t, J=5.8 Hz); [13]C (CDCl$_3$, 150 MHz): δ 205.7, 157.3, 134.3, 128.8, 114.6, 73.1, 64.8, 26.6.

EXAMPLE 6B

Synthesis of 1-(4-hydroxymethyl-phenoxy)-propan-2-ol

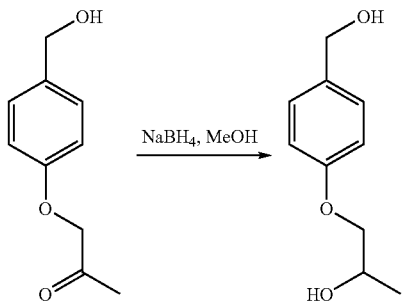

To a solution of 1-(4-hydroxymethylphenoxy)-propan-2-one (1.26 g, 6.99 mmol) dissolved in methanol (60 mL) was added solid NaBH$_4$ (0.32 g, 8.39 mmol). After completion of addition the reaction mixture was stirred at room temperature overnight. The reaction mixture was diluted with water, and the aqueous layer was extracted with ethyl acetate (3×). All combined organic layers were dried over $Na_2SO_4$, filtered, and concentrated to provide an oil (1.24 g, 6.81 mmol), which was used in the next step without any further purification (98% yield). [1]H (CDCl$_3$7.29, 600 MHz): δ (2H, d, J=8.4 Hz), 6.90 (2H, d, J=8.5 Hz), 4.62 (2H, s), 4.21 (1H, m), 3.94 (1H, dd, J=9.2, 3.1 Hz), 3.82 (1H, m), 1.29 (3H, d, J=6.4 Hz).

EXAMPLE 6C

Synthesis of 2-tert-butyl-4-chloro-5-[4-(2-hydroxypropoxy)benzyloxy]-2H-pyridazin-3-one

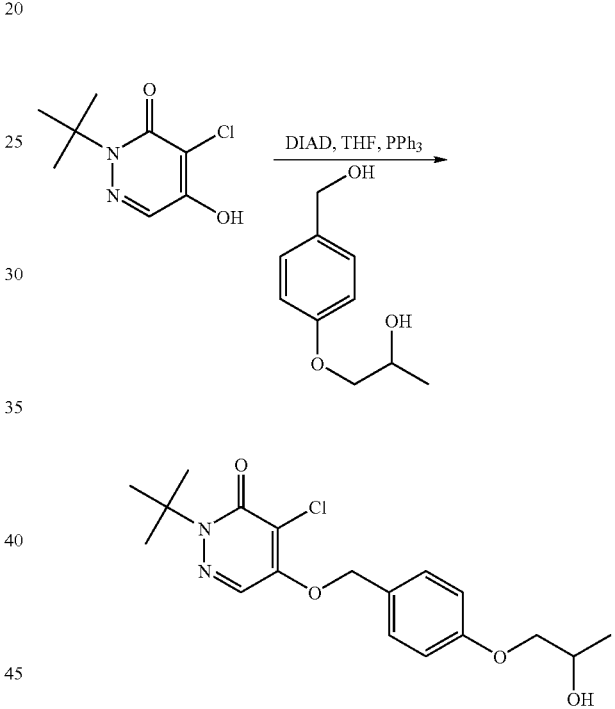

To solution of the product of Example 6B (269 mg, 1.48 mmol) and 2-tert-butyl-4-chloro-5-hydroxy-2H-pyridazin-3-one (250 mg, 1.23 mmol) dissolved in anhydrous THF (18.5 mL) was added solid PPh$_3$ (485 mg, 1.85 mmol) and DIAD (0.358 mL, 1.85 mmol). After completion of addition the reaction mixture continued to stir at room temperature. After 20 hours, the reaction mixture was diluted with water. The aqueous layer was separated and extracted with ethyl acetate (3×). All combined organic layers were dried over $Na_2SO_4$, filtered, and concentrated to provide an oil. The crude material was purified using silica gel chromatography (1:1 pentane:ethyl acetate) to provide the desired product (234 mg, 0.634 mmol) in 51% yield. [1]H (CDCl$_3$ 7.71 (1H, s), 7.33 (2H, d, 600 MHz): δ J=8.7 Hz), 6.94 (2H, d, J=8.7 Hz), 5.24 (2H, s), 4.19 (1H, m), 3.95 (1H, dd, J=9.2, 3.1 Hz), 3.81 (1H, dd, J=9.2, 7.7 Hz), 1.62 (9H, s) 1.29 (3H, d, J=6.4 Hz).

EXAMPLE 6D

Synthesis of toluene-4-sulfonic acid 2-[4-(1-tert-butyl-5-chloro-6-oxo-1,6-dihydro-pyridazin-4-yloxymethyl)-phenoxy]-1-methyl-ethyl ester

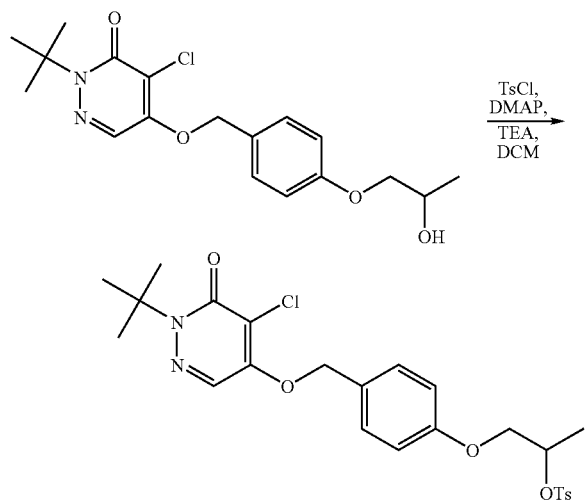

To a solution of the product of Example 6C (200 mg, 0.546 mmol) dissolved in anhydrous dichloromethane (6.0 mL) was added TsCl (125 mg, 0.656 mmol), DMAP (100 mg, 0.819 mmol) and triethylamine (0.0914 mL, 0.656 mmol). The reaction mixture continued stirring at room temperature. After 22 hours the reaction mixture was diluted with water. The aqueous layer was separated and extracted with ethyl acetate (3×). All combined organic layers were dried over $Na_2SO_4$, filtered, and concentrated to provide an oil. The crude material was purified using silica gel:chromatography (70:30 pentane:ethyl acetate) to provide the desired product (166 mg, 0.319 mmol) in 58% yield. $^1$H (CDCl$_3$ 7.80 (2H, d, 600 MHz): δ J=8.3 Hz), 7.72 (1H, s), 7.32 (2H, d, J=7.9 Hz), 7.29 (2H, d, J=8.7 Hz), 6.74 (2H, d, J=8.7 Hz), 5.22 (2H, s), 4.19 (1H, m), 4.02 (1H, dd, J=10.4, 6.0 Hz), 3.93 (1H, dd, J=10.4, 4.5 Hz), 2.44 (3H, s), 1.63 (9H, s) 1.42 (3H, d, J=6.5 Hz); $^{13}$C (CDCl$_3$ 158.9, 150 MHz): δ 158.3, 153.6, 144.6, 133.8, 129.6, 128.8, 127.8, 127.4, 125.1, 118.0, 114.7, 76.8, 71.5, 69.7, 66.2, 27.7, 21.5, 17.6.; HRMS calcd for $C_{25}H_{29}ClN_2O_6S$: 521.150762, found 521.1505.

EXAMPLE 6E

Synthesis of 2-tert-butyl-4-chloro-5-[4-(2-fluoropropoxy)benzyloy]-2H-pyridazin-3-one

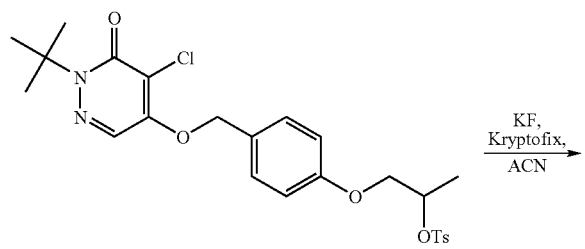

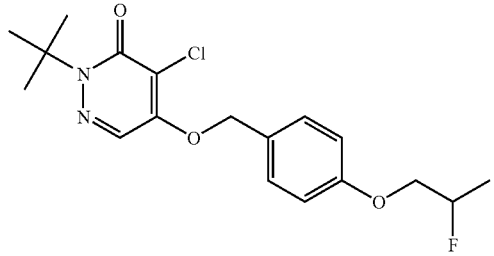

To a solution of the product of Example 6E (50 mg, 0.096 mmol) in anhydrous acetonitrile (1.0 mL) was added KF (11.2 mg, 0.192 mmol) and Kryptofix (72.4 mg, 0.192 mmol). After completion of addition the reaction mixture was heated to 90° C. After 40 minutes, the reaction mixture was cooled down to room temperature and diluted with water. The aqueous layer was separated and extracted with ethyl acetate (3×). All combined organic layers were dried over $Na_2SO_4$, filtered, and concentrated to provide an oil. The crude material was purified using a preparative silica gel thin layer chromatography plate (4:1 pentane:ethyl acetate) to isolate the desired product (12.5 mg, 0.034 mmol) in 41% yield (based on recovererd starting material), in addition to unreacted starting material (5.8 mg, 0.011 mmol). $^1$H (CDCl$_3$, 600 MHz): δ 7.73 (1H, s) 7.34 (2H, d, J=8.6 Hz), 6.95 (2H, d, J=8.6 Hz), 5.25 (2H, s), 5.06-4.96 (1H, m), 4.06 (2H, m), 1.63 (9H, s) 1.47 (311, dd, J=6.4, 23.6 Hz); $^{13}$C (DMSO-d$_6$, 158.4, 157.8, 153.9, 129.8, 127.6, 126.2, 115.5, 114.6, 89.150 MHz); δ (88.0), 71.2, 70.4 (70.3), 65.3, 27.4, 16.9 (16.8); $^{19}$F (DMSO-d$_6$, −178.20 (1F, m); 564 MHz): δ HRMS calcd for $C_{18}H_{22}ClFN_2O_3$: 369.137575, found 369.1370.

EXAMPLE 7A

Synthesis of 4-(3-oxobutyl)benzoic acid methyl ester

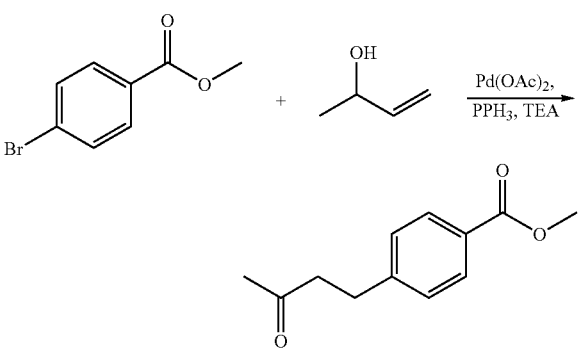

To a solution of methyl-4-bromobenzoate (1.0 g, 4.65 mmol) in triethylamine (13 mL) was added 3-buten-2-ol (1 mL, 11.63 mmol), palladium (II) acetate (0.104 g, 0.465 mmol), and then triphenylphosphine (0.244 g, 0.93 mmol). The reaction was stirred in a 75° C. oil bath overnight under nitrogen atmosphere. Monitoring by TLC (3:1 hexane:ethyl acetate) showed the product and aryl bromide. The reaction was cooled to room temperature and then concentrated. Water was then added followed by extraction with ethyl acetate. The organic layer was washed with water and brine, dried over $Na_2SO_4$, filtered and concentrated. The crude product was purified by flash column chromatography (5:1 to 3:1 hexane:

ethyl acetate) to obtain the product (250 mg, 26% yield). $^1$H NMR (600 MHz, CDCl$_3$): δ 7.95 (d, 2H, J=8.4 Hz), 7.25 (d, 2H, J=8.4 Hz), 3.90 (s, 3H), 2.95 (t, 2H, J=7.45 Hz), 2.77 (t, 2H, J=7.68 Hz), 2.14 (s, 3H).

EXAMPLE 7B

Synthesis of 2-tert-butyl-4-chloro-5-[4-(3-hydroxybutyl)benzyloxy]-2H-pyridazin-3-one

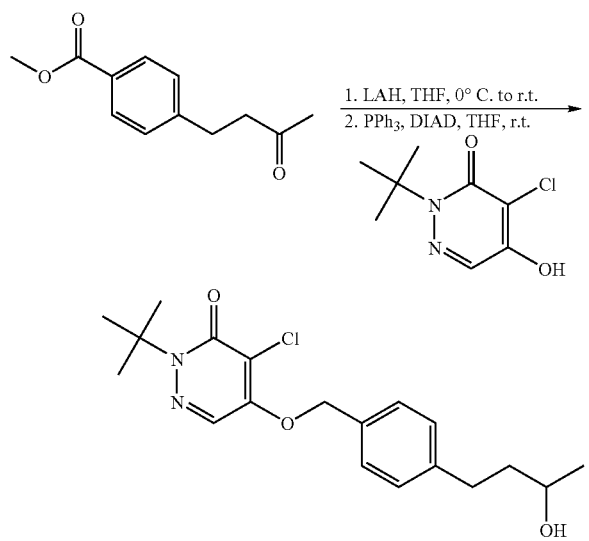

To a solution of the product of Example 7A (505 mg, 2.447 mmol) in THF (19 mL) at 0° C. was added a 1M solution (in THF) of lithium aluminum hydride (12.2 mL, 12.237 mmol) dropwise. After completion of addition the ice bath was removed and the reaction was stirred at room temperature for 1 hour under nitrogen atmosphere. Then, in succession, was added water (183 μL), 15% NaOH solution (183 μL), and water (548 μL). The reaction stirred for an additional 15 minutes before it was filtered and washed with THF. The filtrate was then concentrated under reduced pressure to obtain 4-(4-hydroxymethyl-phenyl)butan-2-ol as a brown oil (314 mg, 71% yield). Then to a solution of 2-tert-butyl-4-chloro-5-hydroxy-2H-pyridazin-3-one (234 mg, 1.155 mmol) in THF (45 mL) was added 4-(4-hydroxymethylphenyl)butan-2-ol (312 mg, 1.732 mmol), triphenylphosphine (454 mg, 1.732 mmol), and then diisopropyl azodicarboxylate (DIAD, 335 μL, 1.732 mmol). The reaction was stirred at room temperature overnight under nitrogen atmosphere. Thin layer chromatography (100% ethyl acetate) indicated consumption of the pyridazinone starting material and the reaction was concentrated. The crude material was purified by flash column chromatography (4:1 hexane:ethyl acetate to 100% ethyl acetate) to obtain a clear oil (200 mg, 48% yield). $^1$H NMR (600 MHz, CDCl$_3$); δ 7.73 (s, 1H), 7.32 (d, 2H, J=8.0), 7.24 (d, 2H, J=8.0), 5.30 (s, 1H), 5.27 (s, 2H), 3.83 (m, 1H), 2.80-2.76 (m, 1H), 2.71-2.66 (m, 1H), 1.63 (s, 9H), 1.23 (d, 3H, J=6.2); $^{13}$C(CDCl$_3$ 159.3, 153.9, 143.2, 132.5, 129.2, 127.6, 125.4, 150 MHz): δ HRMS calcd for C118.5, 73.4, 67.6, 66.6, 40.9, 32.0, 28.1, 23.9.$_{19}$H$_{25}$ClN$_2$O$_3$: 365.162647, found 365.1624.

EXAMPLE 7C

Synthesis of toluene-4-sulfonic acid 3-[4-(1-tert-butyl-5-chloro-6-oxo-1,6-dihydro-pyridazin-4-yloxymethyl)-phenyl]-1-methylpropyl ester

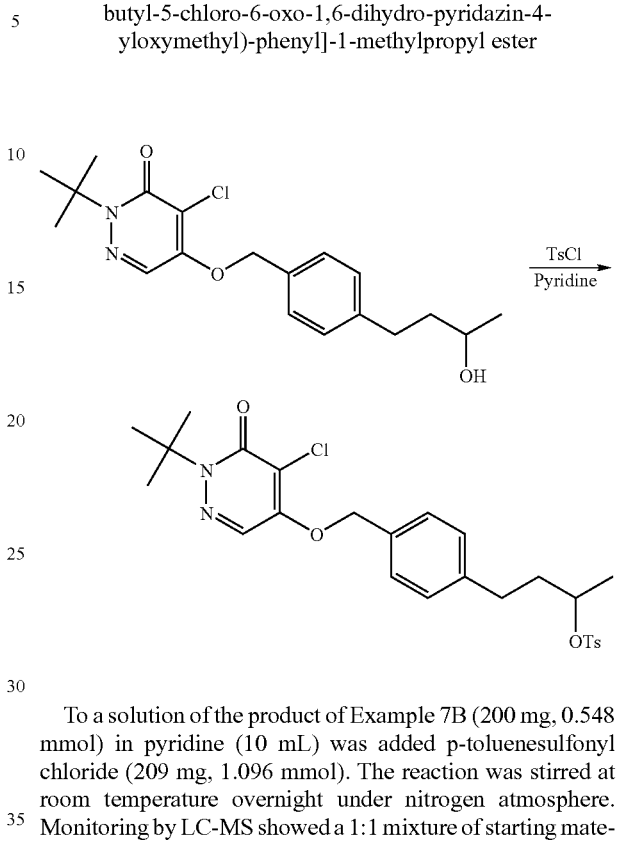

To a solution of the product of Example 7B (200 mg, 0.548 mmol) in pyridine (10 mL) was added p-toluenesulfonyl chloride (209 mg, 1.096 mmol). The reaction was stirred at room temperature overnight under nitrogen atmosphere. Monitoring by LC-MS showed a 1:1 mixture of starting material and product. The reaction was diluted with ethyl acetate and washed with 5% CuSO$_4$ until a light blue aqueous solution was maintained. The organic layer was then dried over Na$_2$SO$_4$, filtered, and concentrated. The crude material was purified by flash column chromatography (3:1 hexane:ethyl acetate to 100% ethyl acetate) to recover the starting material (90 mg) and the product as a clear oil (74 mg, 47% yield based on recovered starting material). $^1$H NMR (600 MHz, CDCl$_3$): 7.80 (d, 2H, J=8.3 Hz), 7.72 (s, 1H), 7.33 (d, 2H, J=8.0 Hz), 7.30 (d, 2H, J=8.1 Hz), 7.13 (d, 2H, J=8.1 Hz), 5.27 (s, 2H), 4.66 (m, 1H), 2.65 (m, 1H), 2.54 (m, 1H), 2.45 (s, 3H), 1.94 (m, 1H), 1.81 (m, 1H), 1.63 (s, 9H), 1.26 (s, 3H).

EXAMPLE 7D

Synthesis of 2-tert-butyl-4-chloro-5-[4-(3-fluorobutyl)benzyloxy]-2H-pyridazin-3-one

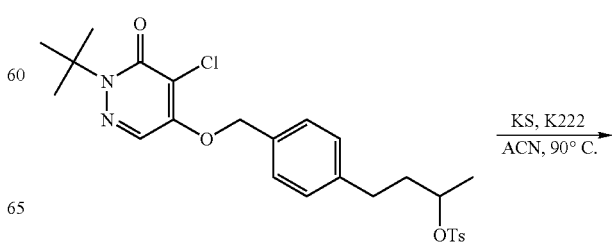

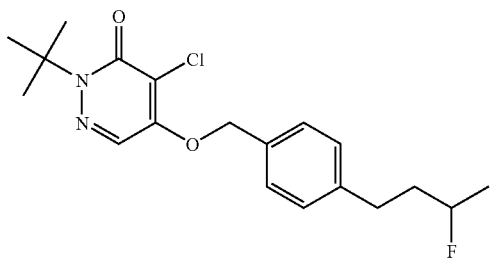

To a solution of the product of Example 7C (18.2 mg, 0.035 mmol) in acetonitrile (400 μL) was added potassium fluoride (4.1 mg, 0.070 mmol) and K222 (26.4 mg, 0.070 mmol). The reaction was stirred at 90° C. for 20 minutes under nitrogen atmosphere, monitoring by LC-MS. The reaction was then cooled to room temperature and concentrated under reduced pressure. The crude material was purified by preparative thin layer chromatography (4:1 hexane:ethyl acetate as eluant) to obtain the product as an oil (5 mg, 39% yield). $^1$H NMR (600 MHz, CDCl$_3$): δ 7.70 (s, 1H), 7.34 (d, 2H, J=7.9 Hz), 7.24 (d, 2H, J=8.0 Hz), 5.28 (s, 2H), 4.71-4.60 (m, 2H), 2.84-2.80 (m, 1H), 2.73-2.69 (m, 1H), 2.02-1.93 (m, 1H), 1.87-1.77 (m, 1H), 1.63 (s, 9H), 1.35 (dd, 3H, J=6.2 and 23.9 Hz); $^{13}$C (CDCl$_3$159.1, 153.8, 150 MHz): δ 142.4, 132.5, 129.0, 127.4, 125.2, 118.3, 90.4 (89.3), 71.9, 66.3, 38.5 (38.4), 31.1 (31.0), 27.9, 21.1 (21.0); $^{19}$F (CDCl$_3$-174.7, 564 MHz): δ (1F, m); HRMS calcd for C$_{19}$H$_{23}$ClFN$_2$O$_2$: 367.158310, found 367.1582.

EXAMPLE 8A

Synthesis of 4-[2-hydroxyethoxymethyl]benzoic acid methyl ester tetradeuterate

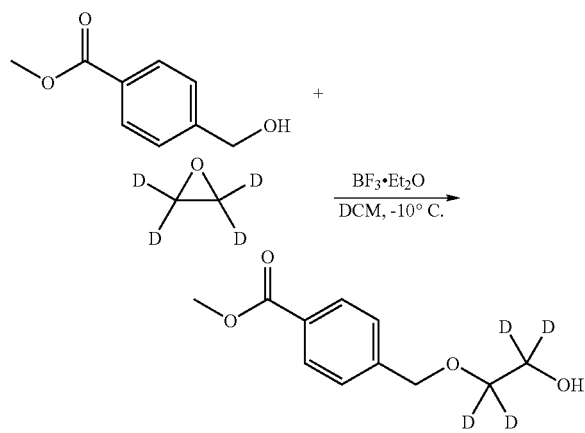

To a flame-dried 2-neck flask was added a solution of methyl-4-(hydroxymethylbenzoate (2.5 g, 15 mmol) in dichloromethane (30 mL). The reaction was purged with nitrogen and brought to −5° C. A dewar condenser (also flame-dried) containing a dry ice/acetone bath (−78° C.) was affixed to the flask and ethylene oxide-tetradeuterate was added (~55 drops). Then BF$_3$.Et$_2$O (510 μL, 0.0041 mmol) was added dropwise and the reaction stirred at −5° C. for 35 minutes under nitrogen atmosphere. Monitoring by TLC (100% ethyl acetate) showed complete consumption of the starting material. The reaction was warmed to room temperature and vented to remove any excess ethylene oxide gas. The reaction was then diluted with brine and extracted with dichloromethane (2 times). The combined organics were dried over Na$_2$SO$_4$, filtered, and concentrated under reduced pressure to obtain a crude oil. Purification by flash column chromatography (4:1 pentane:ethyl acetate) provided the product as a clear oil (520 mg, 16% yield). $^1$H NMR (600 MHz, CDCl$_3$) δ 8.02 (d, 2H, J=8.2 Hz), 7.41 (d, 2H, J=8.1 Hz), 4.62 (s, 2H), 3.92 (s, 3H); $^{13}$C NMR (150 MHz, CDCl$_3$167.1, 143.5, 130.8) δ 129.9, 127.5, 72.8, 52.4.

EXAMPLE 8B

Synthesis of 4-[2-(tert-butyldimethylsilanyloxy) ethoxymethyl]benzoic acid methyl ester tetradeuterate

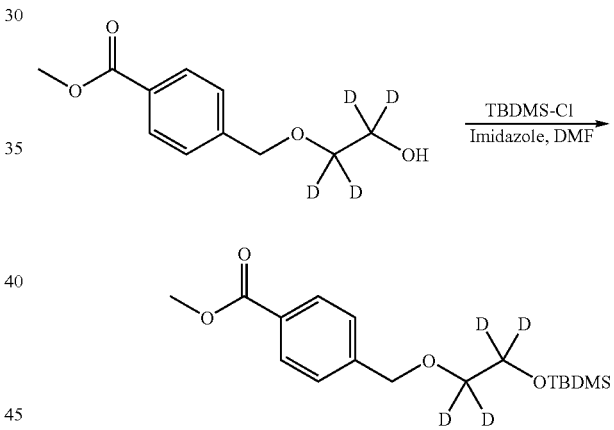

To a solution of the product of Example 8A (500 mg, 2.334 mmol) in DMF (23 mL) was added tert-butyldimethylsilyl chloride (528 mg, 3.501 mmol) and imidazole (238 mg, 3.501). The reaction was stirred at room temperature for 5 hours under nitrogen atmosphere, monitoring by TLC (3:1 pentane:ethyl acetate). Another 0.5 eq. portion of tert-butyldimethylsilyl chloride (176 mg) and imidazole (79 mg) were added and the resultant mixture stirred at room temperature overnight. The majority of the starting material was consumed in 16 hours, as indicated by thin layer chromatography. The reaction was diluted with water and extracted with ethyl acetate (2 times). The combined organic layers were dried over Na$_2$SO$_4$, filtered, and concentrated under reduced pressure to obtain a crude oil which was purified by passage through thick pad of silica gel (3:1 pentane:ethyl acetate) to obtain the product as a clear oil (602 mg). $^1$H NMR (600 MHz, CDCl$_3$): 8.00 (d, 2H, J=8.3 Hz), 7.40 (d, 2H, J=8.5 Hz), 4.62 (s, 2H), 3.90 (s, 3H), 0.90 (s, 9H), 0.06 (s, 6H).

EXAMPLE 8C

Synthesis of {4-[2-(tert-butyldimethylsilanyloxy)ethoxymethyl]phenyl}methanol hexadeuterate

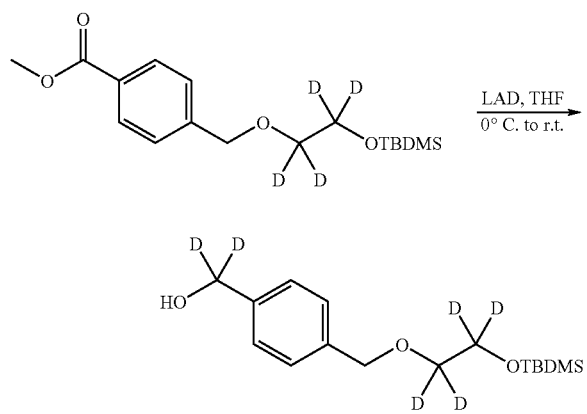

To a solution of the product of Example 8B (610 mg, 1.857 mmol) in THF (19 mL) at 0° C. was added a 1M solution (in THF) of lithium aluminum deuteride (1.9 mL, 1.857 mmol) dropwise. After completion of addition the ice bath was removed and the reaction was stirred at room temperature for 3.5 hours under nitrogen atmosphere, monitoring by TLC (3:1 pentane:ethyl acetate). The reaction was then diluted with water and extracted with ethyl acetate (2 times). The combined organics were dried over $Na_2SO_4$, filtered, and concentrated under reduced pressure to obtain a clear oil (482 mg, 86% yield). The material was taken to the next step without further purification. $^1$H NMR (600 MHz, $CDCl_3$): 7.33 (s, 4H), 4.56 (s, 2H), 0.89 (s, 9H), 0.06 (s, 6H).

EXAMPLE 8D

Synthesis of 2-tert-butyl-4-chloro-5-{4-[2-(tert-butyldimethylsilanyloxy)ethoxymethyl]benzyloxy}-2H-pyridazin-3-one hexadeuterate

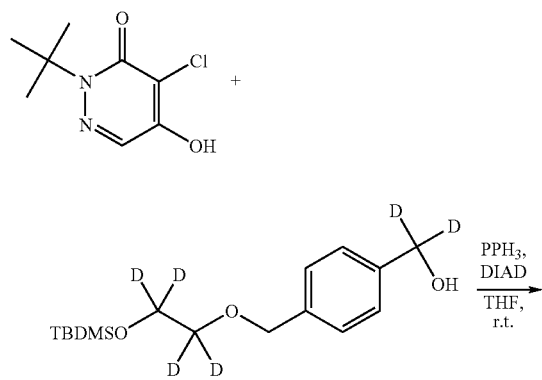

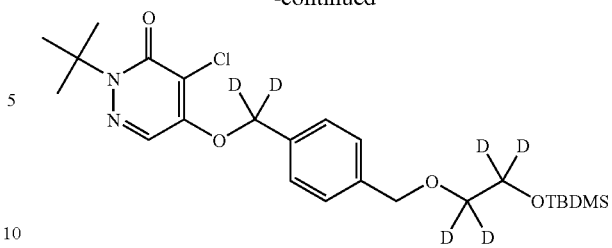

To a solution of 2-tert-butyl-4-chloro-5-hydroxy-2H-pyridazin-3-one (212 mg, 1.047 mmol) in THF (15 mL) was added the product of Example 8C (475 mg, 1.570 mmol), triphenylphosphine (412 mg, 1.570 mmol), and then diisopropyl azodicarboxylate (DIAD, 304 µL, 1.570 mmol). The reaction was stirred at room temperature for 2 hours under nitrogen atmosphere. Thin layer chromatography (1:1 hexane:ethyl acetate) indicated consumption of the pyridazinone starting material and the reaction was concentrated in vacuo. The crude material was purified by flash column chromatography (90:10 pentane:ethyl acetate) to obtain a clear oil (336 mg, 66% yield). $^1$H NMR (600 MHz, $CDCl_3$): 7.70 (s, 1H), 7.39 (m, 4H), 4.58 (s, 2H), 1.63 (s, 9H), 0.90 (s, 9H), 0.07 (s, 6H); HRMS calcd for $C_{24}H_{31}D_6ClN_2O_4Si$: 509.24738, found 509.2480.

EXAMPLE 8E

Synthesis of 2-ter-butyl-4-chloro-5-[4-(2-hydroxyethoxymethyl)benzyloxy]-2H-pyridazin-3-one hexadeuterate

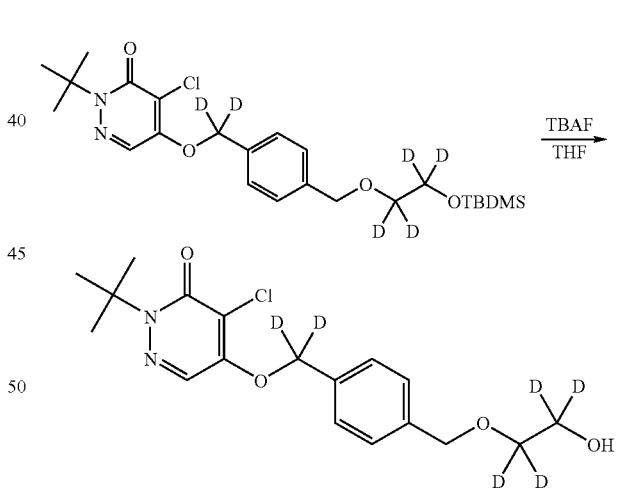

To a solution of the product of Example 8D (330 mg, 0.677 mmol) in THF (7 mL) was added a 1M solution (in THF) of tetrabutylammonium fluoride (1 mL, 1.016 mmol) dropwise. The reaction was stirred at room temperature for 2 hours under nitrogen atmosphere, monitoring by TLC (1:1 hexane:ethyl acetate). The reaction was then concentrated under reduced pressure and passed through a thick pad of silica (100% ethyl acetate) to obtain the product as an oil containing a minor percentage of the corresponding silanol. The material was taken to the next step without further purification. $^1$H NMR (600 MHz, $CDCl_3$); 7.72 (s, 1H), 7.41 (s, 4H), 4.59 (s, 2H), 1.64 (s, 9H); $^{13}$C NMR (150 MHz, rt, $CDCl_3$): 159.2, 153.9, 139.5, 134.5, 128.5, 127.5, 125.3, 118.6, 73.0, 66.6, 28.1; HRMS calcd for $C_{25}H_{23}D_6ClN_2O_6S$: 549.169754, found 549.1705.

EXAMPLE 8F

Synthesis of toluene-4-sulfonic acid 2-[4-(1-tert-butyl-5-chloro-6-oxo-1,6-dihydro-pyridazin-4-yloxymethyl)-benzyloxy]ethyl ester hexadeuterate

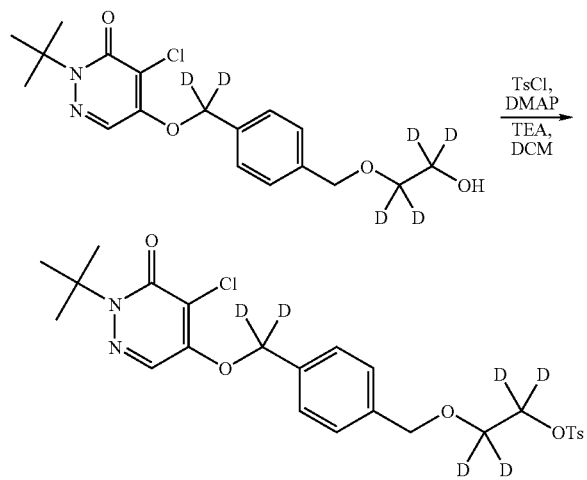

To a solution of the product of Example 8E (250 mg, 0.670 mmol) in dichloromethane (7 mL) was added p-toluenesulfonyl chloride (153 mg, 0.805 mmol), N,N-dimethylaminopyridine (DMAP, 98 mg, 0.805 mmol), and triethylamine (140 µL, 1.005 mmol). The reaction was stirred at room temperature overnight under nitrogen atmosphere. Thin layer chromatography (1:1 hexane:ethyl acetate) indicated almost complete consumption of the alcohol. The reaction was concentrated under reduced pressure and the crude material was purified by flash chromatography (2:1 hexane:ethyl acetate to 1:1 hexane:ethyl acetate to 100% ethyl acetate) to recover the starting material (9 mg) and the product (261 mg, 77% yield based on recovered starting material) as a clear oil. $^1$H NMR (600 MHz, CDCl$_3$): 7.76 (d, 2H, J=8.3 Hz), 7.73 (s, 1H), 7.36 (d, 2H, J=8.1 Hz), 7.29 (m, 4H), 4.47 (s, 2H), 2.40 (s, 3H), 1.61 (s, 9H); $^{13}$C NMR (150 MHz, rt, CDCl$_3$): 159.0, 153.8, 145.0, 138.5, 134.4, 133.1, 129.9, 128.1, 128.0, 127.3, 125.2, 118.1, 72.7, 71.0, 37.0, 63.4, 28.0, 21.7.

EXAMPLE 8G

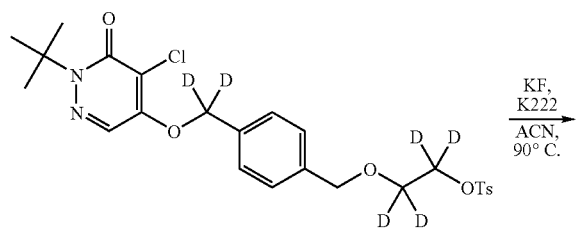

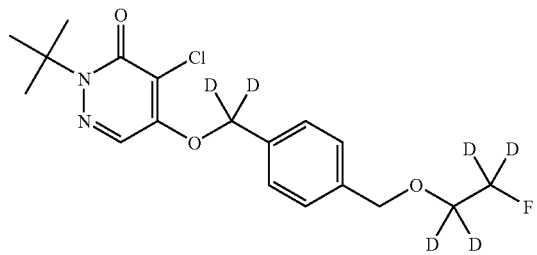

To a solution of the product of Example 8F (14 mg, 0.027 mmol) in acetonitrile (300 µL) was added potassium fluoride (3.1 mg, 0.053 mmol) and K222 (20 mg, 0.053 mmol). The reaction was stirred at 90° C. for 10 minutes under nitrogen atmosphere, monitoring by TLC (1:1 hexane:ethyl acetate). The reaction was then cooled to room temperature and concentrated under reduced pressure. The crude material was purified by preparative TLC (2:1 hexane:ethyl acetate) to obtain the product as an oil (6.2 mg, 62% yield), $^1$H NMR (600 MHz, CDCl$_3$): 7.70 (s, 1H), 7.40 (s, 4H), 4.61 (s, 2H), 1.63 (s, 9H); $^{13}$C NMR (150 MHz, rt, CDCl$_3$): 158.5, 153.1, 138.2, 133.8, 127.7, 126.8, 124.6, 117.8, 72.4, 65.9, 27.3; $^{19}$F NMR (564 MHz, CDCl$_3$): −225.2 (m, 1F).

Radiosynthetic and Purification Procedures for Preparation of Fenazaguin and Pyridaben Complexes Radiolabeled with the Fluorine-18 Radionuclide The Fluorine-18 ($^{18}$F) used in the research is produced via the proton bombardment of enriched Oxygen-18 ($^{18}$O) as $H_2^{18}O$ with using approximately 10 MeV protons by PETnet (Woburn, Mass.). The expression for this nuclear reaction is: $O^{18}(p, \gamma)^{18}F$.

For all of the radiosynthetic reactions a similar procedure was used. All glassware was silanized to preclude adhesion of the material to the vessel walls and optimize transfers. A dedicated, specific HPLC unit was used for purification for all compounds. A dedicated specific HPLC unit was used for radioanalytical analyses of final product.

The $^{18}$F typically was received from the supplier deposited on a processed column ($^{18}$F column) encased in lead shielding. The $^{18}$F column contained the sodium salt coordinated to either alumina or a quaternary ammonium salt housed in a glass column. The column ends are connected to Tygon™ tubing with male and female Luer™ lock fittings. The $^{18}$F is removed from the column using the following method.

1. A solution of 15 mg of potassium carbonate ($K_2CO_3$) in 1 mL of distilled/deionized water ($H_2O$) and a solution of 90 mg of 4,7,13,16,21,24-hexaoxa-1,10-diazabicyclo[8.8.8] hexacosane (Kryptofix™; K222) dissolved in 4 mL of anhydrous acetonitrile ($CH_3CN$) were combined and gently stirred, ensuring the layers did not separate, forming the column eluting solution (CES).
2. A one mL aliquot of the CES was extracted from the vial described in step three using a 3 mL syringe and the syringe was attached to the male Luer™ lock of the Tygon™ tubing connected to the $^{18}$F column.
3. A narrow gauge needle was attached to the female Luer™ lock of the other Tygon™ tubing connected to the $^{18}$F column, and the needle was inserted through the rubber septum fitted to a 15 mL 24/40 Pyrex™ pear-shaped glass flask, 4. The 15 mL pear shaped flask was vented with a needle and the flask was flushed with dry nitrogen. The flushing needle was connected to a vacuum line and the flow adjusted such that CES was slowly drawn through the $^{18}$F column into the mL pear-shaped flask.
5. The vacuum and $N_2$ gas flow were adjusted such that the contents of the flask were reduced to dryness. Anhydrous $CH_3CN$ (1 mL) was added via syringe to the flask, using vacuum to drive the transfer. The vacuum and $N_2$ gas flow were balanced to remove the acetonitrile. This procedure was repeated twice, after which point the vacuum was removed.
6. The contents of the flask were removed via syringe and the radioactivity was quantified. The $^{18}$F solution was used directly in radiolabeling syntheses.

The next steps describe the radiolabeling of the fenazaquin and pyridaben analogs with $^{18}$F. As previously stated these steps were the same for each of the compounds. The following reaction scheme depicts a representative scenario for all of the $^{18}$F-fenazaquin and pyridaben analogs:

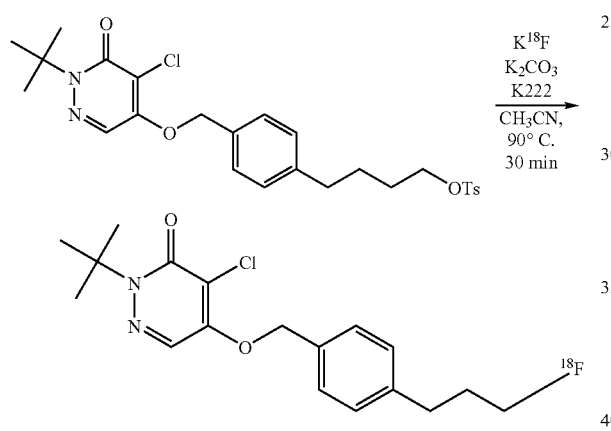

7. The toluenesulfonate ester precursor to the desired fenazaquin or pyridaben analog (2.5 mg) was dissolved in $CH_3CN$ (0.5 mL) in a conical silanized 5 mL Wheaton™ glass vial with a magnetic stirring bar. The vial was immersed in a oil bath heated at 90° C. The solution of the $^{18}$F described above was added to the reaction vial the resultant mixture was heated at 90° C. for 30 minutes.
8. The contents were transferred to a 50 mL silanized round bottom flask containing distilled/deionized water (25 mL), and the contents of the flask are removed via syringe, and deposited on a Waters™ Oasis HLB (hydrophilic-lipophilc balance) column, allowing unreacted fluoride and undesired salts to pass through with the eluate.
9. The organic components were eluted from the column into a conical 5 mL vial using dichloromethane, (3 mL, $CH_2Cl_2$). The eluant was purified via preparative HPLC (Phenomenex LUNA C-18 column 250×10 mm, 5 u particle, 100 A pore. gradient elution 90/10$H_2O$/$CH_3CN$—$CH_3CN$). The appropriate fractions were concentrated and analyzed for radiochemical yield and radiochemical purity (analytical HPLC). The solution was concentrated to dryness in vacuo, and dissolved in the appropriate volume of 10% ethanolic saline for injection and/or biological studies.

Additionally, the following compounds may be prepared following the described procedures:

EXAMPLE 1

Deguelin Analogs

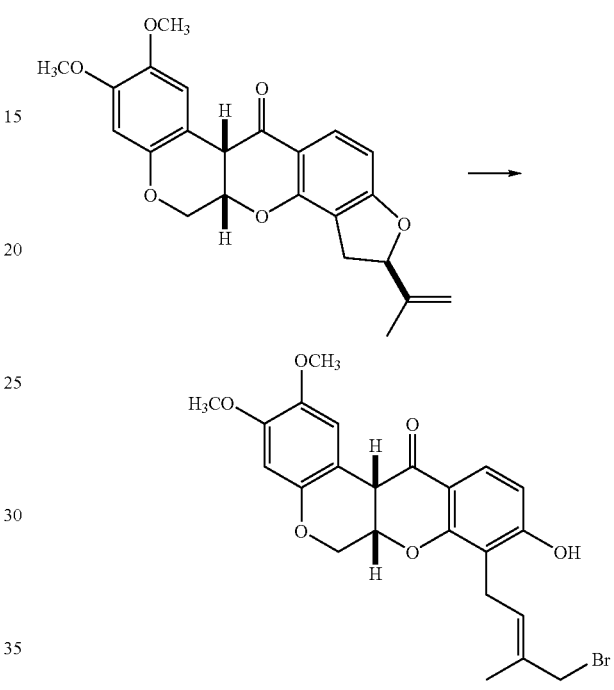

Synthesis of 4'-bromo-rot-2'-enonic acid

Rotenone (5.0 g, 12.7 mmol) dissolved in dichloromethane (30 mL) is added rapidly to a cooled (−10° C.) solution of boron tribromide (3.15 g, 12.7 mmol) in dichloromethane (32.7 mL). The reaction mixture is stirred for exactly two minutes and then evaporated to dryness. The resulting brown crude material is dissolved in the minimum amount of methanol and cooled to 0° C. to initiate crystallization. Brown crystals are collected and dried to afford 4'-bromo-rot-2'-enonic acid (3.24 g).

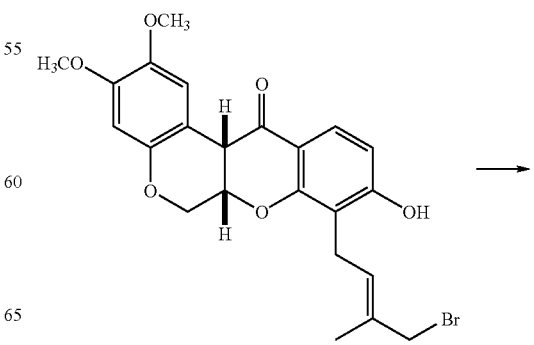

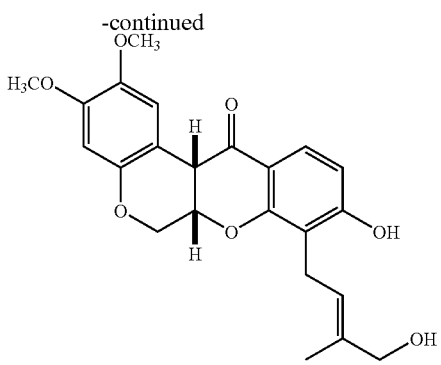

Synthesis of 4'-hydroxy-rot-2' enonic acid

Silver oxide (1.0 g, 4.24 mmol) is added to a solution of 4'-bromo-rot-2' enonic acid (2.0 g, 4.24 mmol) dissolved in acetone (80 mL). After completion of addition the reaction mixture continues to stir in the dark. After 24 h the reaction mixture is filtered through celite and the filtrate is concentrated to yield a yellow oil. The crude material is dissolved in the minimum amount of dichloromethane and cooled to 0° C. to initiate crystallization. 4'-hydroxy-rot-2' enonic acid (1.0 g) can be collected as yellow crystals.

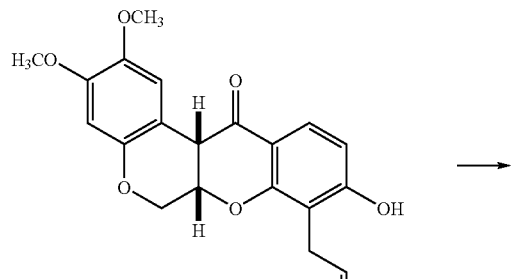

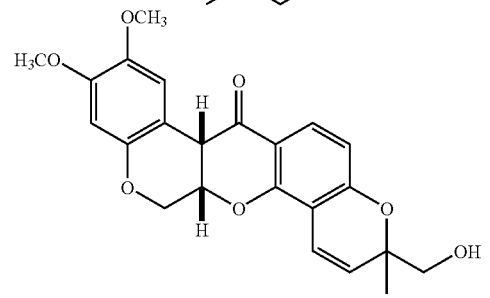

Synthesis of (6aS, 12aS)-7'-hydroxydeguelin

Solid PhSe—Cl (370.87 mg, 1.94 mmol) is added to a cooled (−30° C.) solution of 4-hydroxy-rot-2' enonic acid (725.5 mg, 1.71 mmol) in dichloromethane (20 mL). After completion of addition, the reaction mixture is allowed to warm to room temperature over 2 h and continues to stir at room temperature for an additional hour. After three hours of total reaction time the reaction mixture is concentrated to yield a yellow oil. The crude material is dissolved in THF (20 mL) and cooled to 0° C. Hydrogen peroxide (30% in water, 0.354 mL) is added. After completion of addition the reaction mixture stirs at 0° C. for one hour and then stirs at room temperature overnight. The next day, the reaction mixture is diluted with diethyl ether. The organic layer is separated and washed with 5% $NaHCO_3$ (2×), dried over $Na_2SO_4$ and concentrated to yield (6aS, 12aS)-7'-hydroxydeguelin as a yellow amorphous solid.

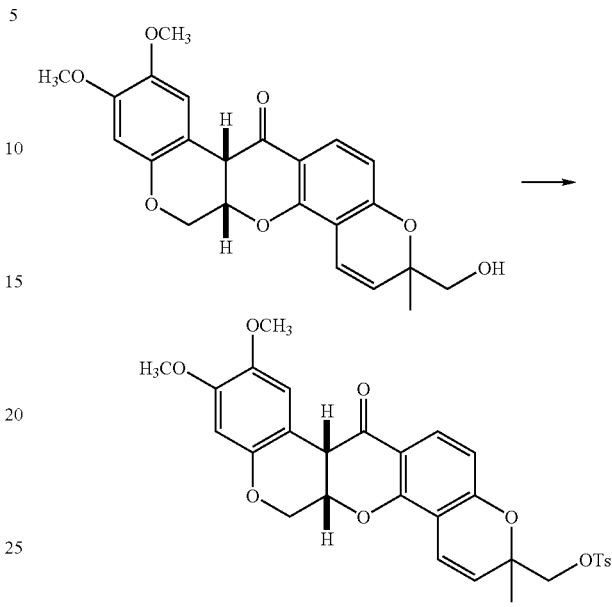

Synthesis of (6aS, 12aS)-7'-toluenesulfonyldeguelin

To a stirring solution of (6aS, 12aS)-7'hydroxy deguelin (30 mg, 0.073 mmol) in dichloromethane (1.5 mL) is added TsCl (15.3 mg, 0.080 mmol) and pyridine (6.47 μL, 0.080 mmol). After completion of addition, the reaction mixture continues to stir at room temperature. After 48 h the reaction is 50% complete according to LCMS and is concentrated. The crude material is purified using silica gel chromatography (gradient from 100% dichloromethane to 25% acetone in dichloromethane) to yield (6aS, 12aS)-7'-toluenesulfonyldeguelin as a yellow oil.

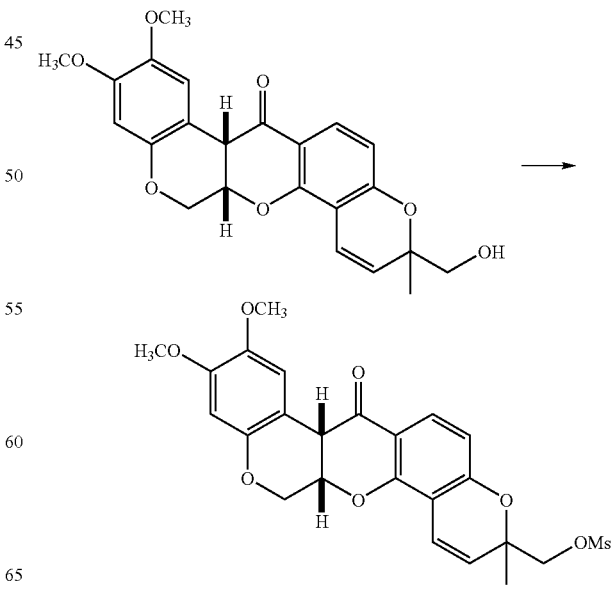

Synthesis of (6aS, 12aS)-7'-methanesulfonyldeguelin

To a stirring solution of (6aS, 12aS)-7'-hydroxydeguelin (50 mg, 0.122 mmol) in dichloromethane (0.5 mL) is added MsCl (9.48 μL, 0.122 mmol) and triethylamine (17.0 μL, 0.122 mmol). After completion of addition the reaction mixture continues to stir at room temperature. After 3 h, additional equivalents of MsCl and triethylamine are added because the reaction is only 80% complete. After 24 h the reaction is complete and diluted with water. The aqueous layer is extracted with dichloromethane. All combined organic layers are dried over $Na_2SO_4$, filtered, and concentrated to yield a yellow oil. Silica gel chromatography (gradient from 100% dichloromethane to 5% acetone in dichloromethane) affords (6aS, 12aS)-7'-methanesulfonyldeguelin (48 mg) as a yellow oil.

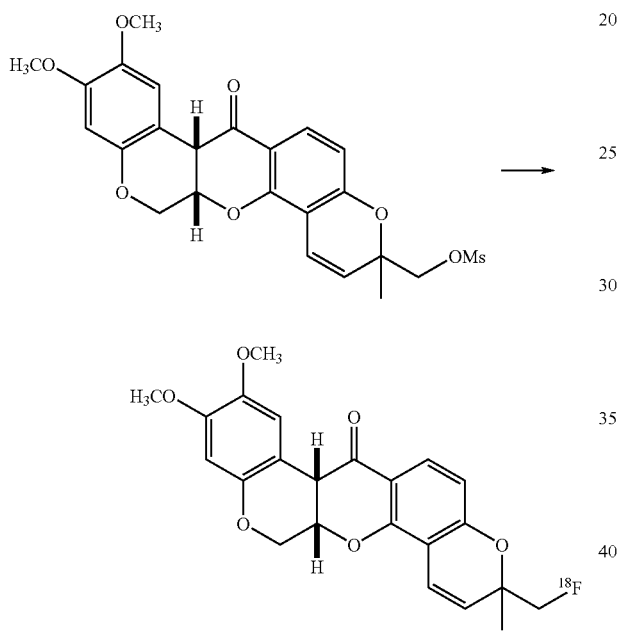

Synthesis of (6aS, 12aS)-7'-[$^{18}$F]fluorodeguelin

A thin-wall 10 mL, silanized vacutainer with a silanized stopper is charged with tetrabutyl ammonium hydroxide (5 uL, 40% w/v solution in water), and a solution of $^{18}F^-$ in water (10 mCi, 200 uL). The resultant mixture is evaporated to dryness under a flow of nitrogen at 100° C. The residue is further dried by repeated addition and evaporation of $CH_3CN$ (3×200 uL). An additional aliquot of $CH_3CN$ is added and concentrated under vacuum without heating. Prior to complete solvent removal, THF (150 uL) is added, the vial is uncrimped and (6aS, 12aS)-7'-methanesulfonyldeguelin (2 mg) is added in one portion. The vial is recapped and heated at 65° C. for 30 minutes. After cooling, the vial is diluted with water (4 mL) and passed through a silica gel cartridge (pre-loaded Waters Light C-18 Sep-Pak) to load the sample. The cartridge is rinsed with water and eluted with $CH_3CN$ (2 mL). The acetonitrile is evaporated and the residue is purified via HPLC to afford pure carrier-free (6aS, 12aS)-7'-[$^{18}$F]fluorodeguelin.

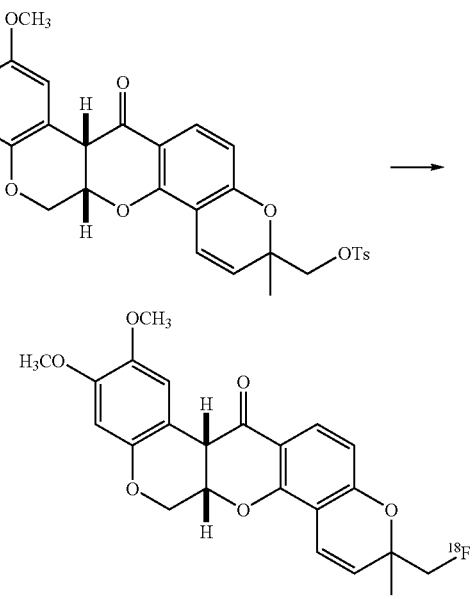

Synthesis of (6aS, 12aS)-7'-[$^{18}$F]fluorodeguelin

A thin-wall 10 mL, silanized vacutainer with a silanized stopper is charged with tetrabutyl ammonium hydroxide (5 uL, 40% w/v solution in water), and a solution of $^{18}$F in water (10 mCi, 200 uL). The resultant mixture is evaporated to dryness under a flow of nitrogen at 100° C. The residue is further dried by repeated addition and evaporation of $CH_3CN$ (3×200 uL). An additional aliquot of $CH_3CN$ is added and concentrated under vacuum without heating. Prior to complete solvent removal, THF (150 uL) is added, the vial is uncrimped and (6aS, 12aS)-7'-toluenesulfonyldeguelin (2 mg) is added in one portion. The vial is recapped and heated at 65° C. for 30 minutes. After cooling, the vial is diluted with water (4 mL) and passed through a silica gel cartridge (pre-loaded Waters Light C-18 Sep-Pak) to load the sample. The cartridge is rinsed with water and eluted with $CH_3CN$ (2 mL). The acetonitrile is evaporated and the residue is purified via HPLC to afford pure carrier (6aS, 12aS)-7'-[$^{18}$F]fluorodeguelin.

Synthesis of (−)-rot-2'enonic Acid

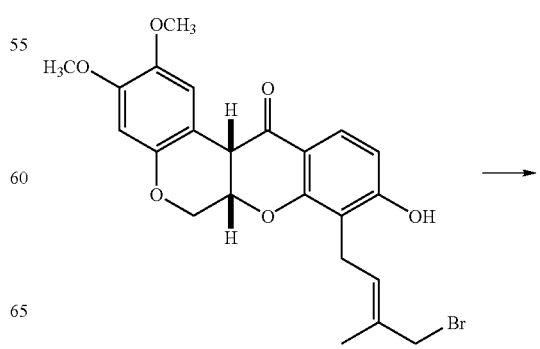

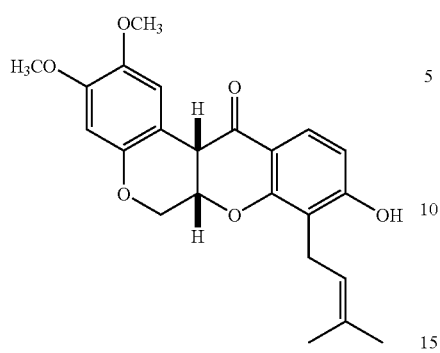

Solid sodium cyanoborohydride (264 mg, 4.20 mmol) is added to a solution of 4'-bromo-rot-2'enonic acid (500 mg, 1.05 mmol) dissolved in HMPA. After

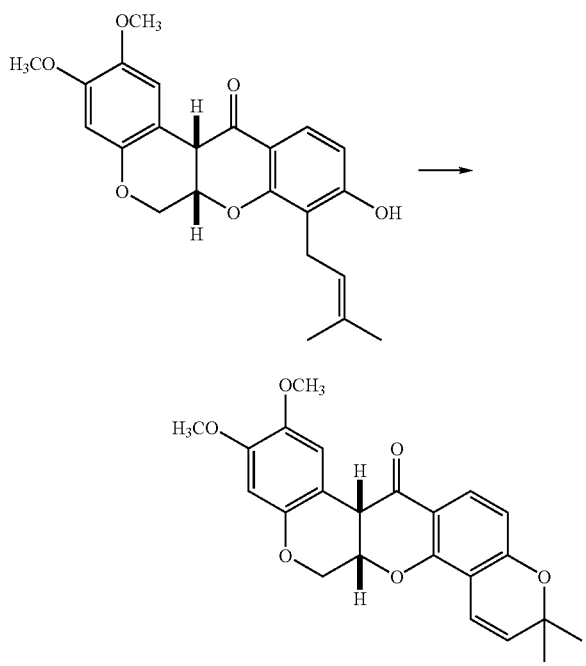

completion of addition the reaction mixture is heated to 70° C. After 2.5 h the reaction is cooled down to room temperature and diluted with water. The aqueous layer is extracted with a diethyl ether/hexane mixture (3/1). The organic layer is dried over Na₂SO₄, filtered, and concentrated to yield a clear oil. Silica gel chromatography (gradient from 20% hexane in dichloromethane to 5% acetone in dichloromethane) affords (−)-rot-2'enonic acid (162.2 mg) as a clear oil.

Synthesis of (6aS, 12aS)-deguelin

Solid PhSe—Cl (185 mg, 0.972 mmol) is added to a cooled (−30° C.) solution of (−)-rot-2'enonic acid (350 mg, 0.884 mmol) in dichloromethane (10.5 mL). After completion of addition the reaction mixture is allowed to warm to room temperature over 2 h and continues to stir at room temperature for an additional hour. After three hours of total reaction time the reaction mixture is concentrated to yield a yellow oil. The crude material is dissolved in THF (10.5 mL) and cooled to 0° C. Hydrogen peroxide (30% in water, 0.177 mL) is added. After completion of addition the reaction mixture continues to stir at 0° C. for one hour and then stirs at room temperature overnight. The next day the reaction mixture is diluted with diethyl ether. The organic layer is separated and washed with 5% NaHCO₃ (2×), dried over Na₂SO₄ and concentrated to yield (6aS, 12aS)-deguelin as a yellow amorphous solid.

Synthesis of (6aS)-deguelin enol ether

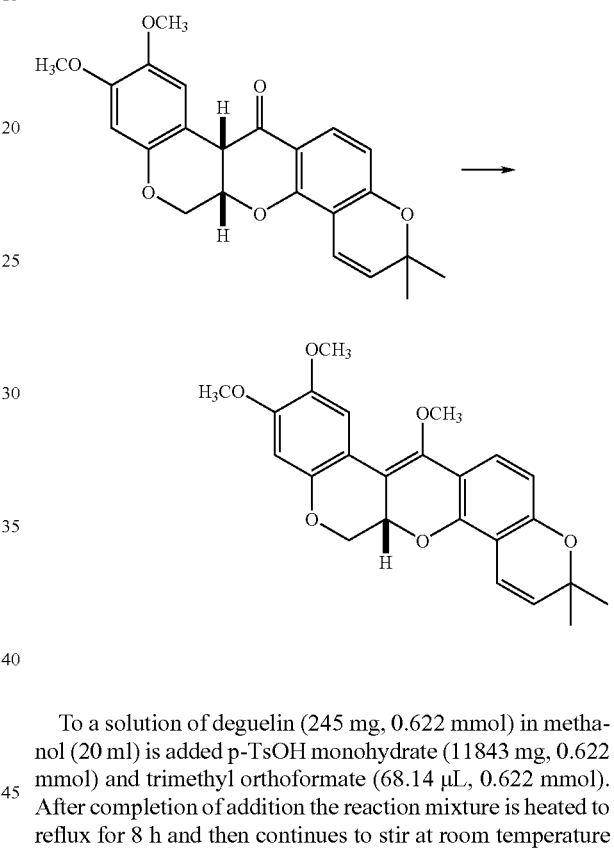

To a solution of deguelin (245 mg, 0.622 mmol) in methanol (20 ml) is added p-TsOH monohydrate (11843 mg, 0.622 mmol) and trimethyl orthoformate (68.14 µL, 0.622 mmol). After completion of addition the reaction mixture is heated to reflux for 8 h and then continues to stir at room temperature overnight. The next day the reaction mixture is diluted with water. The aqueous layer is extracted with ethyl acetate. Combined organic layers are washed with sat. NaHCO₃, dried over Na₂SO₄ and concentrated to yield (6aS)-deguelin enol ether as a yellow amorphous solid.

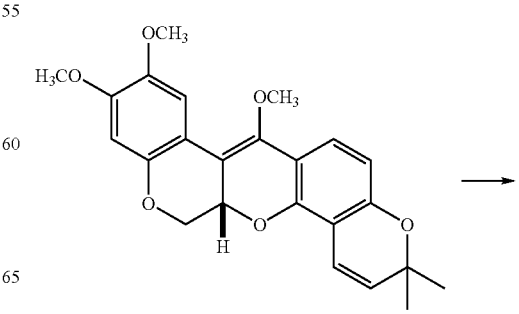

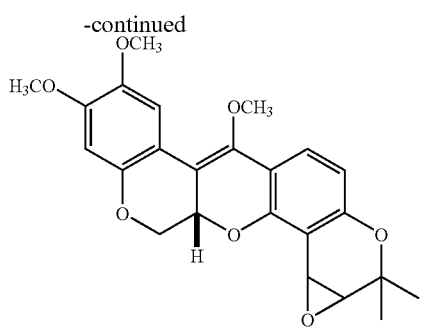

Synthesis of (6aS)-4',5'-dihydro-4',5'epoxydeguelin enol ether

To a cooled (0° C.) solution of (6aS)-deguelin enol ether (50 mg, 0.123 mmol) in dichloromethane (0.5 ml) is added m-CPBA (45 mg, 0.184 mmol). After completion of addition the reaction mixture continues to stir at room temperature. After 6.5 h the reaction is diluted with water. The aqueous layer is extracted with dichloromethane. All combined organic layers are dried over $Na_2SO_4$, concentrated and purified using silica gel chromatography (gradient 100 dichloromethane to 30%

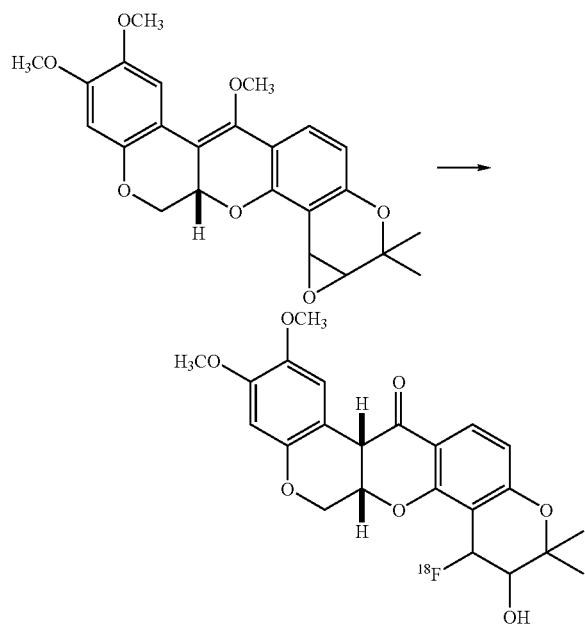

in dichloromethane) to yield (6aS)-4',5'-dihydro-4',5'-epoxydeguelin enol ether

Synthesis of (6aS, 12aS)-4',5',-dihydro-4'[$^{18}$F]fluoro, 5'hydroxydeguelin

A thin-wall 10 mL, silanized vacutainer with a silanized stopper is charged with tetrabutyl ammonium hydroxide (5 uL, 40% w/v solution in water), and a solution of $^{18}$F$^-$ in water (10 mCi, 200 uL). The resultant mixture is evaporated to dryness under a flow of nitrogen at 100° C. The residue is further dried by repeated addition and evaporation of $CH_3CN$ (3×200 uL). An additional aliquot of $CH_3CN$ is added and concentrated under vacuum without heating. Prior to complete solvent removal, THF (150 uL) is added, the vial is uncrimped and (6aS)-4'5'-dihydro-4',5' epoxydeguelin enol ether (2 mg) is added in one portion. The vial is recapped and heated at 65° C. for 30 minutes. After cooling down to room temperature, a solution of trifluoroacteic acid (500 mL) and water (300 mL) is slowly added. The reaction vessel is closed and allowed to stand at 60° C. for 2 min. After cooling to room temperature, the vial is diluted with water (4 mL) and passed through a silica gel cartridge (pre-loaded Waters Light C-18 Sep-Pak) to load the sample. The cartridge is rinsed with water and eluted with $CH_3CN$ (2 mL). The acetonitrile is evaporated and the residue is purified via HPLC to afford pure carrier-free (6aS, 12aS)-4',5'-dihydro-4'[$^{18}$F]fluoro, 5'hydroxydeguelin.

Synthesis of (6aS,12aS)-2-0-desmethyldeguelin

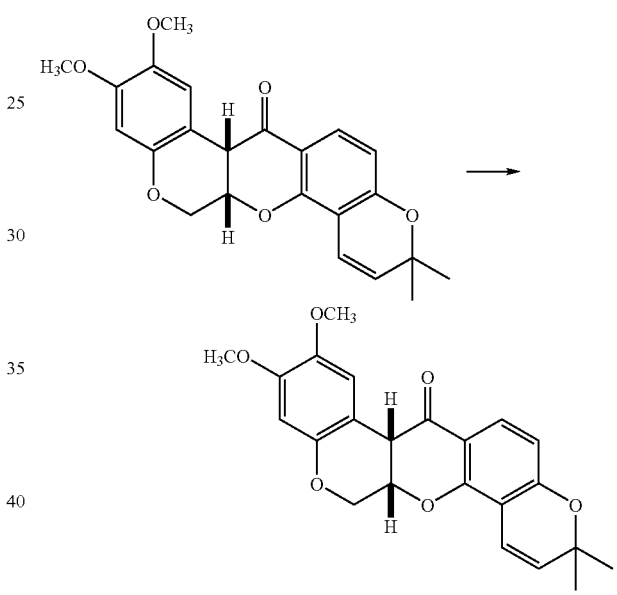

(6aS, 12aS)-Deguelin (251 mg, 0.638 mmol) and sodium methanethiolate (125 mg, 1.78 mmol) are dissolved in 4 ml of N,N-dimethylacetamide and heated at 80° C. for 26 h. The reaction mixture is diluted to 50 ml with water and extracted with dichloromethane. The aqueous layer is then acidified with 5% HCl and extracted again with dichloromethane. All of the organic layers are dried over $Na_2SO_4$, concentrated, and purified using silica gel chromatography (100% dichloromethane to 30% acetone in dichloromethane) to yield (6aS, 12aS)-2-O-desmethyldeguelin.

Synthesis of (6aS, 12aS)-2-[$^{18}$F]fluoromethoxydeguelin

[$^{18}$F]F is made by irradiating [$^{18}$O]water (>94 at %; 400 μL) in silver target chambers with 17 meV protons from a 103 cm AVF cyclotron. Typical irradiations are of 45 min. duration with a beam current of 10 mA yielding about 18 GBq [$^{18}$F] fluoride. After irradiation, the target water is transported via silicone tubing to the synthesis apparatus. This apparatus consists of a borosilicate vessel (5 ml), which

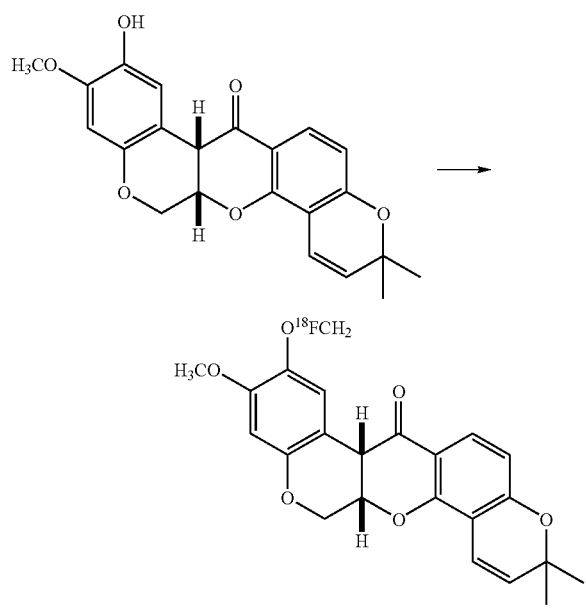

contains potassium carbonate (5 mg, 36 µmol) and K2.2.2 (18 mg, 48 µmol) in acetonitrile (1 mL). The target water is evaporated under reduced pressure and He-flow. Three portions of acetonitrile are added at 110° C. The reaction chamber is allowed to cool down to room temperature and dibromomethane (50 µL) in acetonitrile (1 ml) is added to the dry $^{18}$F/K2.2.2-mixture. The reaction mixture is heated again at 110° C. and the volatile products were transferred to a preparative GC with He as a carrier. The column is heated to 100° C. and [$^{18}$F]CH$_2$BrF is separated from solvents and other reagents.

Freshly obtained [$^{15}$F]CH$_2$BrF is added to a vial containing (6aS,12aS)-2-0-desmethyldeguelin (2 mg) in ACN (150 uL). The vial is recapped and heated at 65° C. for 30 minutes. After cooling, the vial is diluted with water (4 mL) and passed through a silica gel cartridge (pre-loaded Waters Light C-18 Sep-Pak) to load the sample. The cartridge is rinsed with water and eluted with CH$_3$CN (2 mL). The acetonitrile is evaporated and the residue is purified via HPLC to afford pure carrier (6aS, 12aS)-2-[$^{18}$F]fluoromethoxydeguelin.

Synthesis of (6aS, 12aS)-2-[$^{18}$F]fluoroethoxydeguelin

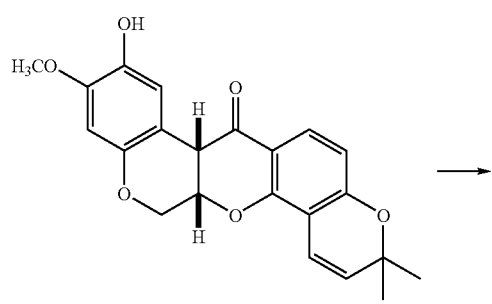

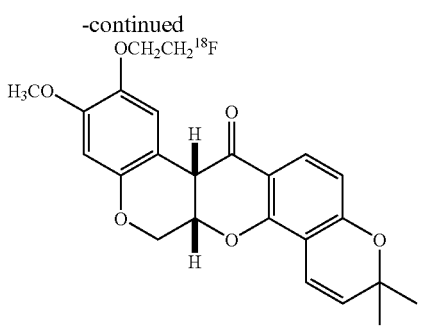

Toluenesulfonylchloride (38.3 g, 0.201 mol) and pyridine (15.9 g, 0.201 mol) are added to a solution of ethane-1,2-diol (5 g, 0.081 mol)) in dichloromethane (100 mL) at 0° C. After completion of addition the reaction stirs at room temperature overnight. In the morning the reaction mixture is diluted with water. The aqueous layer is extracted with dichloromethane, dried over Na$_2$SO$_4$, and concentrated. The crude material is purified using silica gel chromatography (4:1 hexanes ethyl acetate to 100% ethyl acetate) to obtain ditosyl ethane in good yield. A thin-wall 10 mL, silanized vacutainer with a silanized stopper is charged with tetrabutyl ammonium hydroxide (8.5 uL, 40% w/v solution in water), and a solution of $^{18}$F$^-$ in water (10 mCi, 340 uL). The resultant mixture is evaporated to dryness under a flow of nitrogen at 100° C. The residue is further dried by repeated addition and evaporation of CH$_3$CN (3×200 uL). An additional aliquot of CH$_3$CN is added and concentrated under vacuum without heating. Prior to complete solvent removal, THF (150 uL) is added, the vial is uncrimped and 1,2-ditoluenesulfonato ethane (3.4 mg) is added in one portion. The vial is recapped and heated at 85° C. for 30 minutes. After cooling down to room temperature, the solvent is removed under reduced pressure to yield the [$^{18}$F] fluoroethyl tosylate precursor (2.0 mg, 0.010 mmol). (6aS, 12aS)-2-0-desmethyldeguelin (3.8 mg, 0.010 mmol) and tetrabutylammonium hydroxide (2.6 mg, 0.010 mmol) are added in DMF (0.25 mL) and the reaction mixture is heated again to 60° C. After 15 min. the reaction mixture is cooled down to room temperature, the vial is diluted with water (4 mL) and passed through a silica gel cartridge (pre-loaded Waters Light C-18 Sep-Pak) to load the sample. The cartridge is rinsed with water and eluted with CH$_3$CN (2 mL). The acetonitrile is evaporated and the residue is purified via HPLC to afford pure carrier (6aS, 12aS)-2-[$^{18}$F]fluoroethoxydeguelin.

Synthesis of (6aS)-4',5'-dihydro-5'-hydroxydeguelin enol ether

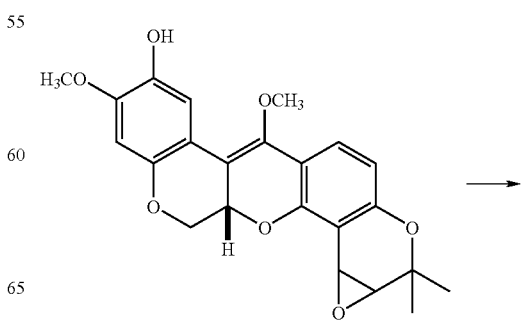

-continued

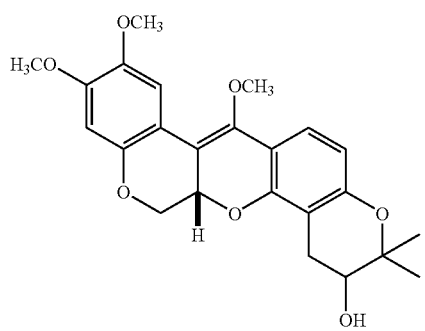

(6aS)-4',5'-dihydro-4',5'-epoxydeguelin enol ether (1.0 g, 2.35 mmol) is dissolved in THF (20 mL) and cooled to 0° C. Lithium aluminum hydride (2.35 mL of 1 M THF solution) is added dropwise to the stirring solution. After completion of addition the reaction mixture stirs at room temperature overnight. In the morning the reaction is quenched with water. The aqueous layer is extracted with ethyl acetate. All organic layers are dried over $Na_2SO_4$, concentrated and purified using silica gel chromatography (100% dichloromethane to 30% acetone in dichloromethane) to yield (6aS)-4',5'-dihydro-5'-hydroxydeguelin enol ether.

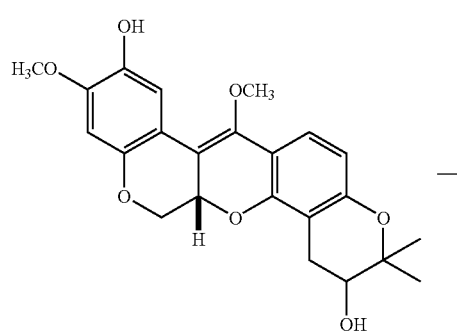

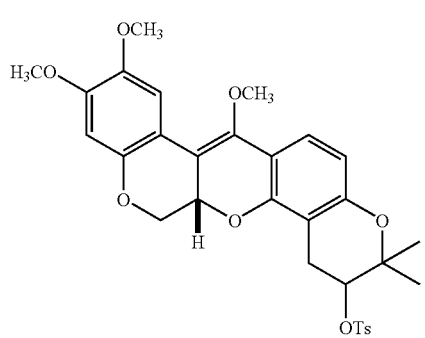

Synthesis of (6aS)-4',5'-dihydro-5'toluenesulfonyldeguelin enol ether

To a stirring solution of (6aS)-4',5'-dihydro-5'-hydroxydeguelin enol ether (31 mg, 0.073 mmol) in dichloromethane (15 mL) is added TsCl (15.3 mg, 0.080 mmol) and pyridine (6.47 μL, 0.080 mmol). After completion of addition the reaction mixture continues to stir at room temperature. After 28 h the reaction is complete according to LCMS and is concentrated. The crude material is purified using silica gel chromatography (gradient from 100% dichloromethane to 25% acetone in dichloromethane) to yield (6aS)-4',5'-dihydro-5'toluenesulfonyldeguelin enol ether.

Synthesis of (6aS, 12aS)-4',5'-dihydro-5'[$^{18}$F]fluorodeguelin

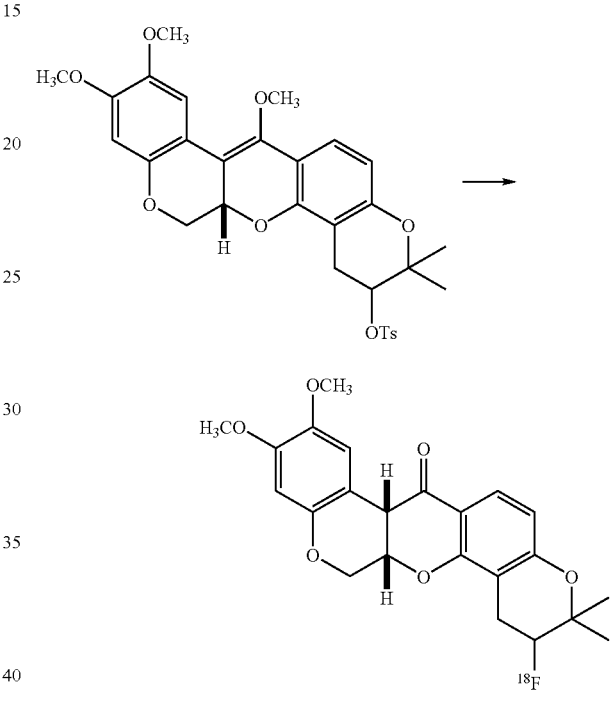

A thin-wall 10 mL, silanized vacutainer with a silanized stopper is charged with tetrabutyl ammonium hydroxide (5 uL, 40% w/v solution in water), and a solution of $^{18}$F$^-$ in water (10 mCi, 200 uL). The resultant mixture is evaporated to dryness under a flow of nitrogen at 100 degrees C. The residue is further dried by repeated addition and evaporation of $CH_3CN$ (3×200 uL). An additional aliquot of $CH_3CN$ is added and concentrated under vacuum without heating. Prior to complete solvent removal, THF (150 uL) is added, the vial is uncrimped and (6aS)-4',5'-dihydro-5'toluenesulfonyldeguelin enol ether (2 mg) is added in one portion. The vial is recapped and heated at 65 degrees C. for 30 minutes. After cooling down to room temperature, a solution of trifluoroacteic acid (500 μL) and water (300 μL) is slowly added. The reaction vessel is closed and allowed to stand at 60° C. for 2 min. After cooling to room temperature, the vial is diluted with water (4 mL) and passed through a silica gel cartridge (pre-loaded Waters Light C-18 Sep-Pak) to load the sample. The cartridge is rinsed with water and eluted with $CH_3CN$ (2 mL). The acetonitrile is evaporated and the residue is purified via HPLC to afford pure carrier-free (6aS, 12aS)-4',5'-dihydro-5'[$^{18}$F]fluorodeguelin.

Synthesis of (6aS)-4',5'-dihydro-5'-carbonyldeguelin enol ether

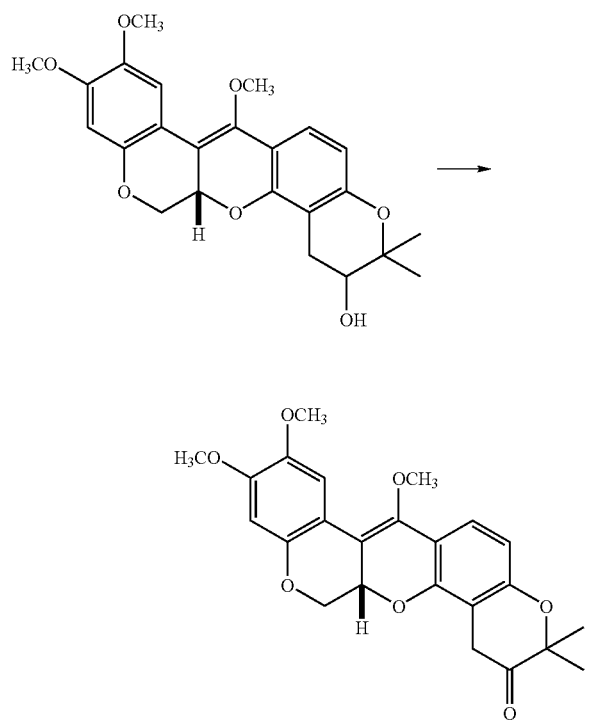

(6aS)-4',5'-dihydro-5'-hydroxydeguelin enol ether (1.0 g, 2.3 mmol) dissolved in dichloromethane (20 mL) is added to a solution of PCC (0.51 g, 2.3 mmol) in dichloromethane (20 mL). After stirring at room temperature for 2 h, the reaction is filtered through a pad of celite and concentrated. The crude material is purified by silica gel chromatography (100% dichloromethane to 30% acetone in dichloromethane) to yield of (6aS)-4',5'-dihydro-5'-carbonyldeguelin enol ether.

Synthesis of (6aS)-5'-trimethylstannyldeguelin enol ether

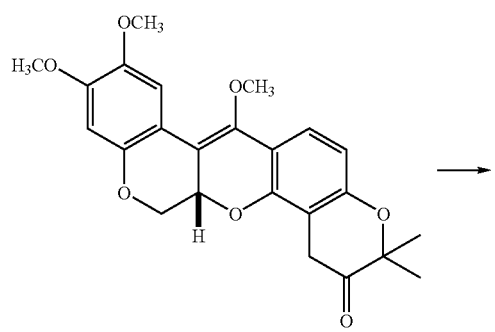

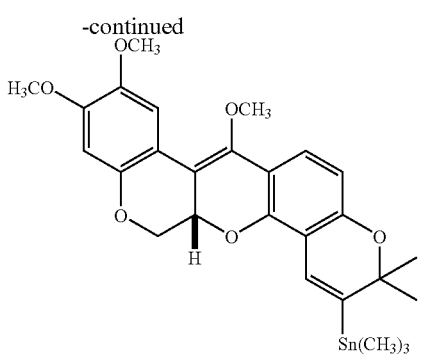

To a solution of 2,4,6-triisopropylbenzenesulfonyl-hydrazide (33.0 g, 0.10 mol) in ACN (100 mL) is added (6aS)-4',5'-dihydro-5'-carbonyldeguelin enol ether (42.4 g, 0.10 mol) of 5'-carbonyl deguelin enol ether and 10 mL of concentrated hydrochloric acid. The solution is stirred at room temperature and then cooled to 0° C. for 4 h. The trisyl hydrazone derivative is collected as a solid.

A solution of the trisyl hydrazone derivative (38.3 mmol, 22.67 g) in 200 mL of TMEDA-hexanes (1:1) is metalated with exactly 2.0 equivalents of sec-buytllithium/cyclohexane (76.6 mmole s-BuLi, −80° C.) and allowed to warm to −10° C. until $N_2$ evolution ceased (40 min.) A solution of freshly sublimed trimethyltin chloride (50 mmole, 9.97 g, 1.3 equiv.) in 30 mL hexane is added all at once. Aqueous work-up is followed by distillation through a short path apparatus at reduced pressure to give (6aS)-5'-trimethylstannyldeguelin enol ether.

Synthesis of (6aS, 12aS)-5'[$^{18}$F]fluorodeguelin

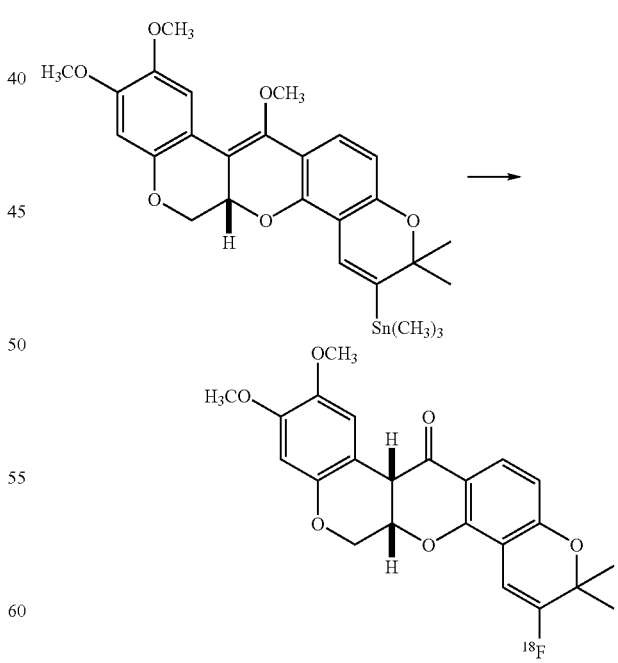

A thin-wall 10 mL, silanized vacutainer with a silanized stopper is charged with tetrabutyl ammonium hydroxide (5 uL, 40% w/v solution in water), and a solution of $^{18}F^-$ in water (10 mCi, 200 uL). The resultant mixture is evaporated to dryness under a flow of nitrogen at 100 degrees C. The residue is further dried by repeated addition and evaporation of CH₃CN (3×200 uL). An additional aliquot of CH₃CN is added and concentrated under vacuum without heating. Prior to complete solvent removal, THF (150 uL) is added, the vial is uncrimped and (6aS)-5'-trimethylstannyldeguelin enol ether (2 mg) is added in one portion. The vial is recapped and heated at 65 degrees C. for 30 minutes. After cooling down to room temperature, a solution of trifluoroacteic acid (500 µL) and water (300 µL) is slowly added. The reaction vessel is closed and allowed to stand at 60° C. for 2 min. After cooling to room temperature, the vial is diluted with water (4 mL) and passed through a silica gel cartridge (pre-loaded Waters Light C-18 Sep-Pak) to load the sample. The cartridge is rinsed with water and eluted with CH₃CN (2 mL). The acetonitrile is evaporated and the residue is purified via HPLC to afford pure carrier-free (6aS, 12aS)-5'[¹⁸F]fluorodeguelin.

Synthesis of (6aS)-4',5'-dihydro-4' hydroxydeguelin enol ether

30% acetone in dichloromethane to yield (6aS)-4',5'-dihydro-4' hydroxydeguelin enol ether.

Synthesis of (6aS)-4',5'-dihydro-4'-carbonyldeguelin enol ether

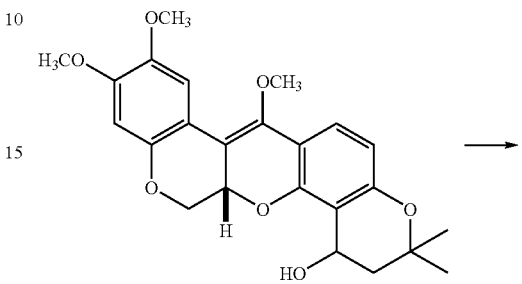

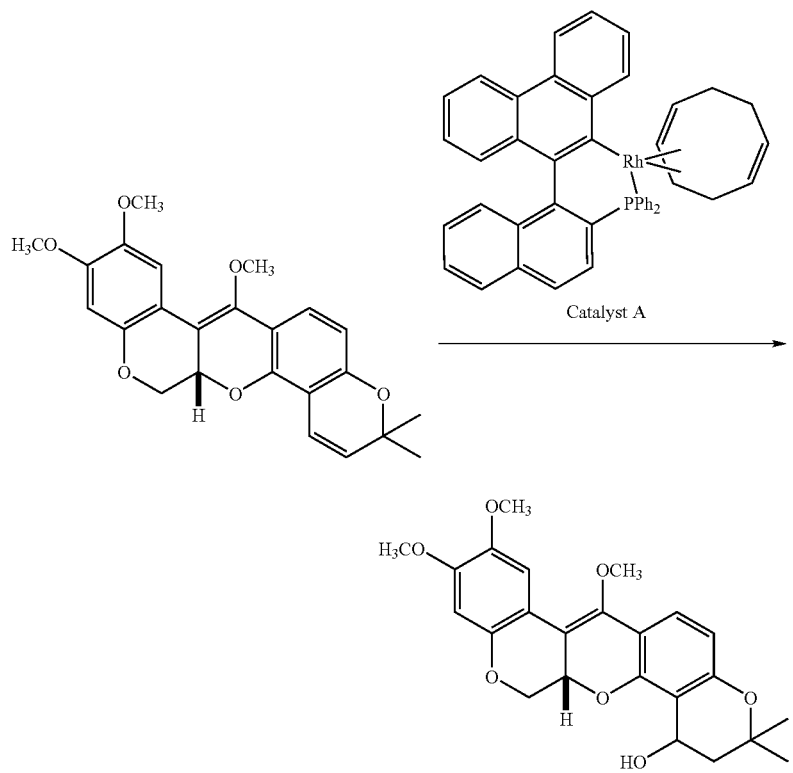

(6aS)-Deguelin enol ether (155.0 mg, 0.38 mmol) and catecholborane (0.40 mL of 1.0M THF solution, 0.40 mmol) are added to a solution of catalyst A (0.003 g, 1 mol %) in THF (0.5 mL). Catalyst A is prepared according to the procedures found in WO 95/13284. The mixture is stirred under nitrogen for 2 h, then quenched with EtOH (0.5 mL), NaOH (2.0 M in water, 0.5 mL) and hydrogen peroxide (30% in water, 0.5 mL), with stirring for an additional two hours. The reaction mixture is extracted with diethyl ether. The organic layer is washed with 1.0 M NaOH, dried over Na₂SO₄, and purified using silica gel chromatography (100% dichloromethane to -continued

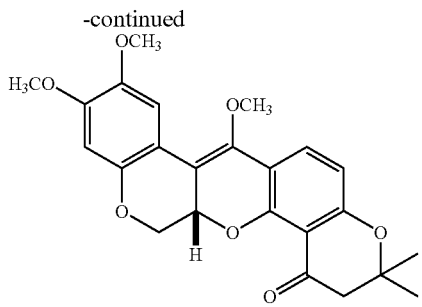

(6aS)-4',5'-dihydro-5'-hydroxydeguelin enol ether (1.0 g, 2.3 mmol) dissolved in dichloromethane (20 mL) is added to a solution of PCC (0.51 g, 2.3 mmol) in dichloromethane (20 mL). After stirring at room temperature for 2 h, the reaction is filtered through a pad of celite and concentrated. The crude material is purified by silica gel chromatography (100% dichloromethane to 30% acetone in dichloromethane) to yield (6aS)-4',5'-dihydro-4'-carbonyldeguelin enol ether.

Synthesis of (6aS)-4'-trimethylstannyldeguelin enol ether

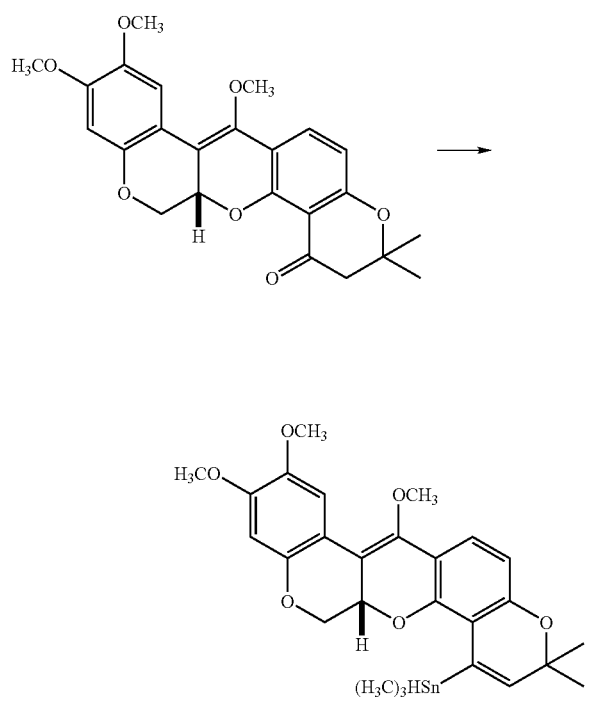

To a solution of 2,4,6-triisopropylbenzenesulfonyl-hydrazide (33.0 g, 0.10 mol) in ACN (100 mL) is added (6aS)-4',5'-dihydro-4'-carbonyldeguelin enol ether (42.4 g, 0.10 mol) and 10 mL of concentrated hydrochloric acid. The solution is stirred at room temperature and then cooled to 0° C. for 4 h. The trisyl hydrazone derivative is collected as a solid.

A solution of the trisyl hydrazone derivative (38.3 mmol, 22.67 g) in 200 mL of TMEDA-hexanes (1:1) is metalated with exactly 2.0 equivalents of sec-buytllithium/cyclohexane (76.6 mmole s-BuLi, −80° C.) and allowed to warm to −10° C. until $N_2$ evolution ceased (40 min.) A solution of freshly sublimed trimethyltin chloride (50 mmole, 9.97 g, 1.3 equiv.) in 30 mL hexane is added all at once. Aqueous work-up is followed by distillation through a short path apparatus at reduced pressure to give (6aS)-4'-trimethylstannyldeguelin enol ether.

Synthesis of (6aS,12aS)-4'[$^{18}$F]fluorodeguelin

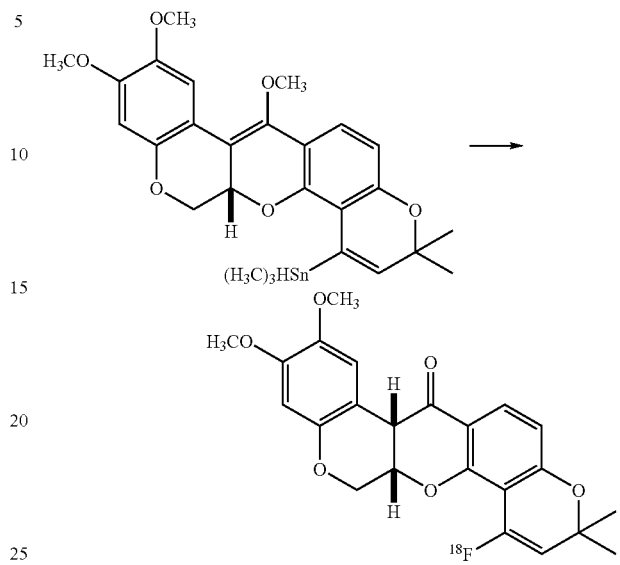

A thin-wall 10 mL, silanized vacutainer with a silanized stopper is charged with tetrabutyl ammonium hydroxide (5 uL, 40% w/v solution in water), and a solution of 18F⁻ in water (10 mCi, 200 uL). The resultant mixture is evaporated to dryness under a flow of nitrogen at 100 degrees C. The residue is further dried by repeated addition and evaporation of $CH_3CN$ (3×200 uL). An additional aliquot of $CH_3CN$ is added and concentrated under vacuum without heating. Prior to complete solvent removal, THF (150 uL) is added, the vial is uncrimped and (6aS)-5'-trimethylstannyldeguelin enol ether (2 mg) is added in one portion. The vial is recapped and heated at 65 degrees C. for 30 minutes. After cooling down to room temperature, a solution of trifluoroacteic acid (500 μL) and water (300 μL) is slowly added. The reaction vessel is closed and allowed to stand at 60° C. for 2 min. After cooling to room temperature, the vial is diluted with water (4 mL) and passed through a silica gel cartridge (pre-loaded Waters Light C-18 Sep-Pak) to load the sample. The cartridge is rinsed with water and eluted with $CH_3CN$ (2 mL). The acetonitrile is evaporated and the residue is purified via HPLC to afford pure carrier-free (6aS, 12aS)-4'[18F]flourodeguelin.

Synthesis of 2,4-dihydroxy-6-nitro-benzaldehyde

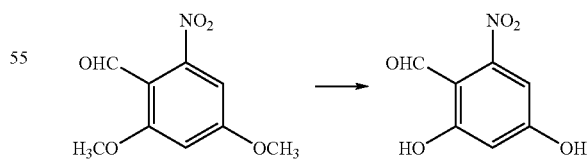

2,4-dimethoxy-6-nitro-benzaldehyde (135 mg, 0.638 mmol) and sodium methanethiolate (125 mg, 1.78 mmol) are dissolved in 4 ml of N,N-dimethylacetamide and heated at 80° C. for 26 h. The reaction mixture is diluted to 50 ml with water and extracted with dichloromethane. The aqueous layer is then acidified with 5% HCl and extracted again with dichloromethane. All of the organic layers are dried over $Na_2SO_4$, concentrated, and purified using silica gel chromatography (100% dichloromethane to 30% acetone in dichloromethane) to yield 2,4-dihydroxy-6-nitro-benzaldehyde.

Synthesis of 2,4-dihydroxy-5-nitro-benzaldehyde

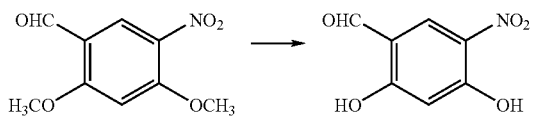

2,4-dimethoxy-5-nitro-benzaldehyde (135 mg, 0.638 mmol) and sodium methanethiolate (125 mg, 1.78 mmol) are dissolved in 4 ml of N,N-dimethylacetamide and heated at 80° C. for 26 h. The reaction mixture is diluted to 50 ml with water and extracted with dichloromethane. The aqueous layer is then acidified with 5% HCl and extracted again with dichloromethane. All of the organic layers are dried over $Na_2SO_{41}$ concentrated, and purified using silica gel chromatography (100% dichloromethane to 30% acetone in dichloromethane) to yield 2,4-dihydroxy-5-nitro-benzaldehyde.

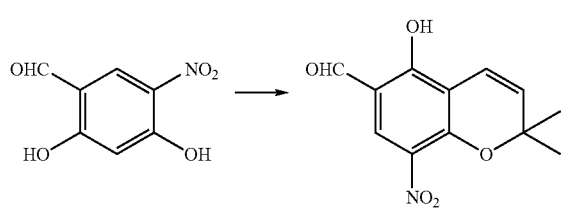

Synthesis of 5-hydroxy-2,2-dimethyl-8-nitro-2H-chromene-6-carbaldehyde

A solution of 2,4-dihydroxy-5-nitro-benzaldehyde (10.61 g, 58 mmol) in $Me_2CO$ (6 mL) is added during a 5.5 h period to a stirring solution of 3-methyl-but-2-enal (4.00 g, 29 mmol) in pyridine (2.29 g, 2.34 mL, 29 mmol) at 120° C. After completion of addition heating is continued for an additional 18 h. The $Me_2CO$ is evaporated and the pyridine is removed by azeotrope distillation with toluene to afford a crude product. The crude product is purified using silica gel chromatography with 1% ethyl acetate in hexanes to afford 5-hydroxy-2,2-dimethyl-8-nitro-2H-chromene-6-carbaldehyde.

Synthesis of 5-hydroxy-2,2-dimethyl-7-nitro-2H-chromene-6-carbaldehyde

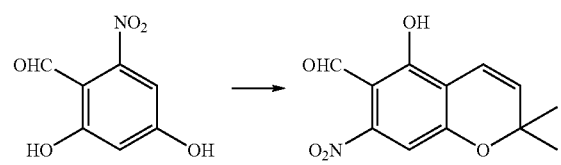

A solution of 2,4-dihydroxy-6-nitro-benzaldehyde (10.61 g, 58 mmol) in $Me_2CO$ (6 mL) is added during a 5.5 h period to a stirring solution of 3-methyl-but-2-enal (4.00 g, 29 mmol) in pyridine (2.29 g, 2.34 mL, 29 mmol) at 120° C. After completion of addition heating is continued for an additional 18 h. The $Me_2CO$ is evaporated and the pyridine is removed by azeotrope distillation with toluene to afford a crude product. The crude product is purified using silica gel chromatography with 1% ethyl acetate in hexanes to afford 5-hydroxy-2,2-dimethyl-7-nitro-2H-chromene-6-carbaldehyde.

Synthesis of 5-methoxy-2,2-dimethyl-7-nitro-2H-chromene-6-carbaldehyde

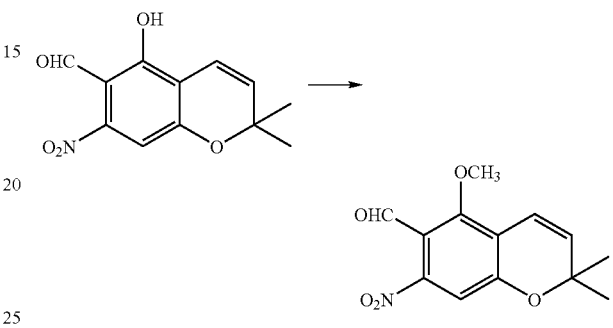

A mixture of 5-hydroxy-2,2-dimethyl-7-nitro-2H-chromene-6-carbaldehyde (2.34 g, 10 mmol), $K_2CO_3$ (4.12 g, 29.8 mmol) and MeI (2.13 g, 0.94 mL, 15 mmol in $Me_2CO$ (40 mL) is refluxed for 4 h and stirred at room temperature overnight. The mixture is concentrated, treated with water (15 mL) and extracted with dichloromethane. The combined organic layers are washed with waters dried over $Na_2SO_4$, and the solvent is removed in vacuo to afford an oil, which is chromatographed with 3% $Me_2CO$ in hexane to afford 5-methoxy-2,2-dimethyl-7-nitro-2H-chromene-6-carbaldehyde.

Synthesis of 5-methoxy-2,2-dimethyl-8-nitro-2H-chromene-6-carbaldehyde

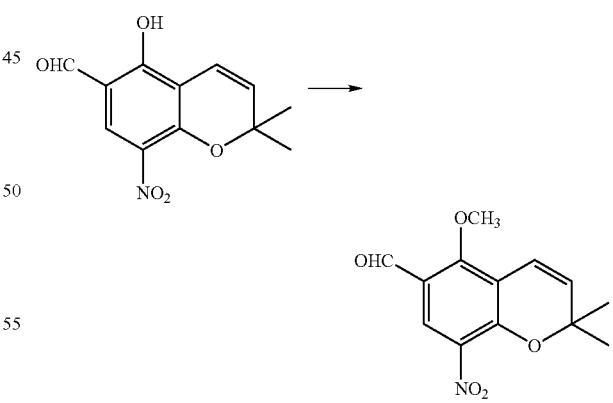

A mixture of 5-hydroxy-2,2-dimethyl-8-nitro-2H-chromene-6-carbaldehyde (2.34 g, 10 mmol), $K_2CO_3$ (4.12 g, 29.8 mmol) and MeI (2.13 g, 0.94 mL, 15 mmol in $Me_2CO$ (40 mL) is refluxed for 4 h and stirred at room temperature overnight. The mixture is concentrated, treated with water (15 mL) and extracted with dichloromethane. The combined organic layers are washed with water, dried over $Na_2SO_4$, and the solvent is removed in vacuo to afford an oil, which is chromatographed with 3% Me₂CO in hexane to afford 5-methoxy-2,2-dimethyl-8-nitro-2H-chromene-6-carbaldehyde.

Synthesis of 4-but-2-ynyloxy-1,2-dimethoxybenzene

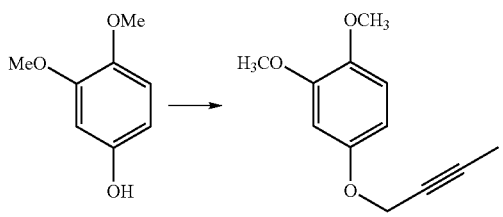

To 3,4-dimethoxy phenol (15.4 g, 0.1 mol) in DMF (100 mL) is added propargyl bromide (14.15 g, 0.12 mol) and potassium carbonate (11.88 g, 0.12 mol). The reaction is stirred at room temperature for 12 h, sat. NH₄Cl and diethyl ether are added. The organic layers are washed with water, brine and dried over Na₂SO₄. The crude material is filtered trough a pad of silica (1:1 hexanes:dichloromethane) to afford 4-but-2-ynyloxy-1,2-dimethoxybenzene as a yellow oil.

Synthesis of 4-(3,4-dimethoxy-phenyoxy)-1-(5-methoxy-2,2-dimethyl-8-nitro-2H-chromen-6-yl)-but-2-yn-1-one

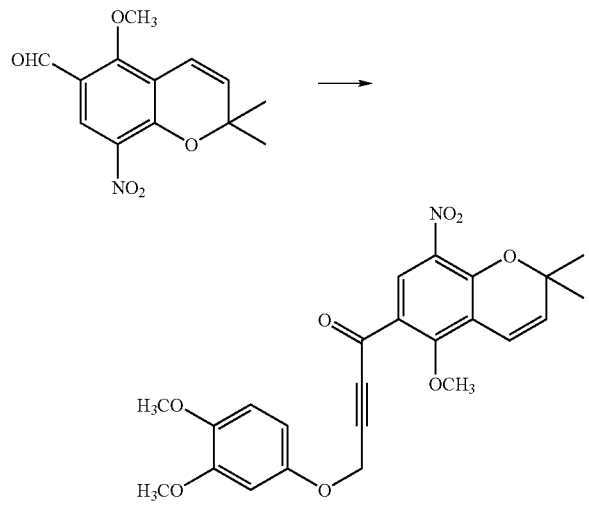

To a solution of 4-but-2-ynyloxy-1,2-dimethoxybenzene (1.66 g, 8.66 mmol) in THF (75 mL) is added n-butyl lithium (5.54 ml of 1.6 M solution in THF, 8.86 mmol) at −78° C. After 30 min., 5-methoxy-2,2-dimethyl-8-nitro-2H-chromene-6-carbaldehyde (2.17 g, 8.25 mmol) in THF (50 mL) is added. The reaction is stirred for 1 h and then quenched with sat. NH₄Cl and extracted with ethyl acetate. The combined organic layers are washed with brine and dried over Na₂SO₄. The resulting crude material is dissolved in dichloromethane (20 mL) and MnO₂ (5.3 g, 61 mmol) is added. After the reaction is stirred overnight at room temperature, ether is added and the suspension is filtered through a pad of celite and silica gel to afford 4-(3,4-dimethoxy-phenyoxy)-1-(5-methoxy-2,2-dimethyl-8-nitro-2H-chromen-6-yl)-but-2-yn-1-one.

Synthesis of 4-(3,4-dimethoxy-phenyoxy)-1-(5-methoxy-2,2-dimethyl-7-nitro-2H-chromen-6-yl)-but-2-yn-1-one

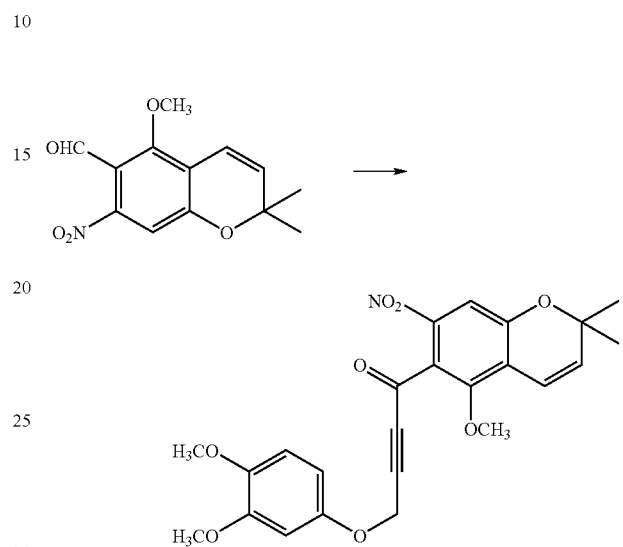

To a solution of 4-but-2-ynyloxy-1,2-dimethoxy-benzene (1.66 g, 8.66 mmol) in THF (75 mL) is added n-butyl lithium (5.54 ml of 1.6 M solution in THF, 8.86 mmol) at −78° C. After 30 min., 5-methoxy-2,2-dimethyl-7-nitro-2H-chromene-6-carbaldehyde (2.17 g, 8.25 mmol) in THF (50 mL) is added. The reaction is stirred for 1 h and then quenched with sat. NH₄Cl and extracted with ethyl acetate. The combined organic layers are washed with brine and dried over Na₂SO₄. The resulting crude material is dissolved in dichloromethane (20 mL) and MnO₂ (5.3 g, 61 mmol) is added. After the reaction is stirred overnight at room temperature, ether is added and the suspension is filtered through a pad of celite and silica gel to afford 4-(3,4-dimethoxy-phenyoxy)-1-(5-methoxy-2,2-dimethyl-7-nitro-2H-chromen-6-yl)-but-2-yn-1-one.

Synthesis of (6,7-dimethoxy-2H-chroman-3-yl)-(5-methoxy-2,2-dimethyl-7-nitro-2H-chromen-6-yl)-methanone

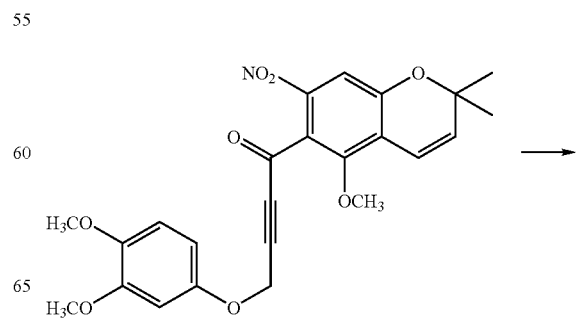

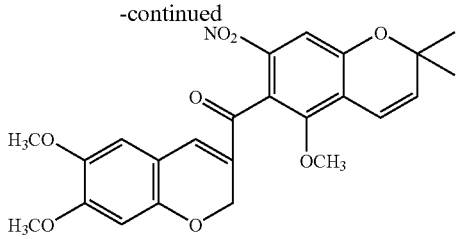

In a flame dried 10 ml round bottom flask is added 4-(3,4-dimethoxy-phenyoxy)-1-(5-methoxy-2,2-dimethyl-7-nitro-2H-chromen-6-yl)-but-2-yn-1-one (61.6 mg, 0.135 mmol) and PtCl$_2$ (1.8 mg, 5 mol %). The flask is evacuated and flushed with argon three times, followed by the addition of toluene (1.8 mL, 0.1 m). The reaction is allowed to stir at 55° C. for 10 h and then concentrated. The crude material is purified using silica gel chromatography (7:3 hexanes:ethyl acetate) to

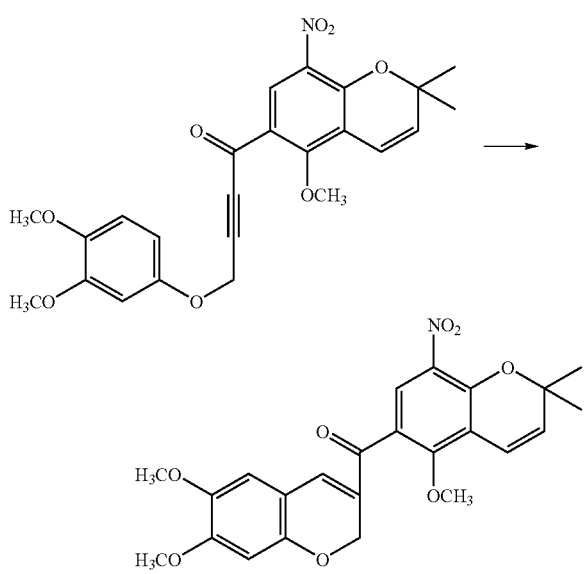

afford (6,7-dimethoxy-2H-chroman-3-yl)-(5-methoxy-2,2-dimethyl-7-nitro-2H-chromen-6-yl)-methanone.

Synthesis of (6,7-dimethoxy-2H-chroman-3-yl)-(5-methoxy-2,2-dimethyl-8-nitro-2H-chromen-6-yl)-methanone In a flame dried 10 ml round bottom flask is added 4-(3,4-dimethoxy-phenyoxy)-1-(5-methoxy-2,2-dimethyl-8-nitro-2H-chromen-6-yl)-but-2-yn-1-one (61.6 mg, 0.135 mmol) and PtCl$_2$ (1.8 mg, 5 mol %). The flask is evacuated and flushed with argon three times, followed by the addition of toluene (1.8 mL, 0.1 m). The reaction is allowed to stir at 55° C. for 10 h and then concentrated. The crude material is purified using silica gel chromatography (7:3 hexanes:ethyl acetate) to afford (6,7-dimethoxy-2H-chroman-3-yl)-(5-methoxy-2,2-dimethyl-8-nitro-2H-chromen-6-yl)-methanone.

Synthesis of (+/−)-10-nitrodeguelin

To a flame dried 10 mL round bottom flask is added (6,7-dimethoxy-2H-croman-3-yl)-(5-methoxy-2,2-dimethyl-8-nitro-2H-chromen-6-yl)-methanone (50.2 mg, 0.111 mmol) and dichloromethane (2.0 mL). The solution is cooled to −78° C. and boron trichloride (0.133 mL, 1 M solution in dichloromethane, 0.133 mmol) is added. After stirring for 1 h the reaction is quenched with sat. NH$_4$Cl, extracted with

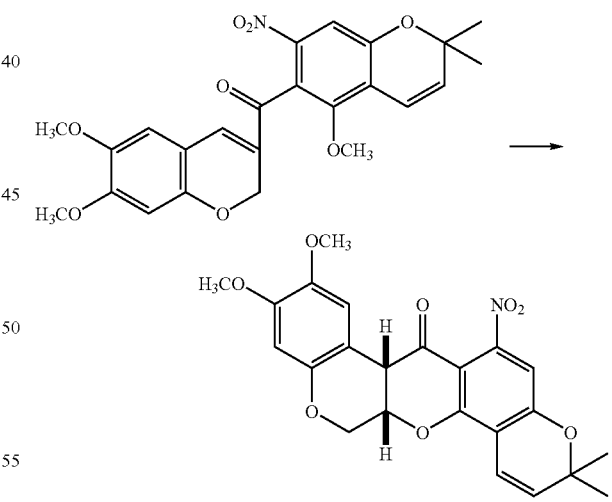

ethyl acetate, dried over Na$_2$SO$_4$, and concentrated. The crude material is dissolved in EtOH, saturated with potassium acetate and refluxed for 1 h. After cooling down to room temperature, ethyl acetate and water are added to the reaction mixture. The aqueous layer is extracted with ethyl acetate. Combined organic layers are washed with brine, dried over Na$_2$SO$_4$, and concentrated. The crude material is filtered through a pad of silica (3:1 hexanes, ethyl acetate) to yield (+/−)-10-nitrodeguelin.

Synthesis of (+/−)11-nitrodeguelin

To a flame dried 10 mL round bottom flask is added (6,7-dimethoxy-2H-chroman-3-yl)-(5-methoxy-2,2-dimethyl-7- nitro-2H-chromen-6-yl)-methanone (0.2 mg, 0.111 mmol) and dichloromethane (2.0 mL). The solution is cooled to −78° C. and boron trichloride (0.133 mL, 1 M solution in dichloromethane, 0.133 mmol) is added. After stirring for 1 h the reaction is quenched with sat. NH$_4$Cl, extracted with ethyl acetate, dried over Na$_2$SO$_4$, and concentrated. The crude material is dissolved in EtOH, saturated with potassium acetate and refluxed for 1 h. After cooling down to room temperature, ethyl acetate and water are added to the reaction mixture. The aqueous layer is extracted with ethyl acetate. Combined organic layers are washed with brine, dried over Na$_2$SO$_4$, and concentrated. The crude material is filtered through a pad of silica (3:1 hexanes, ethyl acetate) to yield (+/−)-11-nitrodeguelin.

Synthesis of (+/−)-11-[$^{18}$F]fluorodeguelin

A thin-wall 10 mL, silanized vacutainer with a silanized stopper is charged with tetrabutyl ammonium hydroxide (5 uL, 40% w/v solution in water), and a solution of $^{18}$F$^−$ in water (10 mCi, 200 uL). The resultant mixture is evaporated to

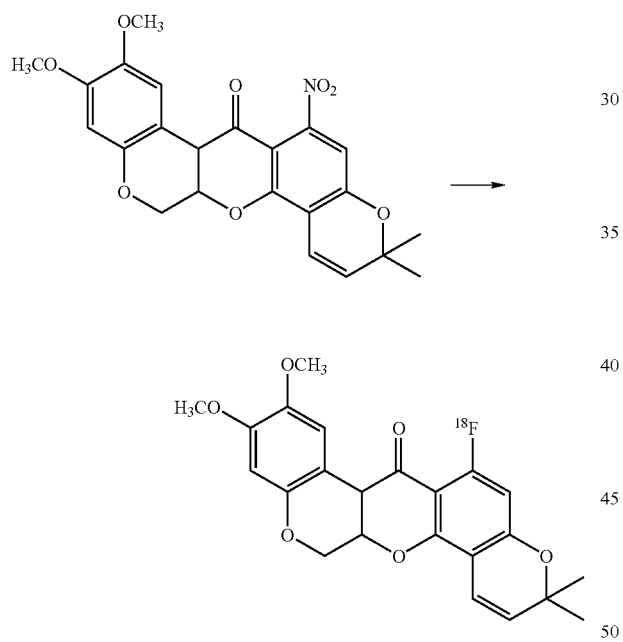

dryness under a flow of nitrogen at 100° C. The residue is further dried by repeated addition and evaporation of CH$_3$CN (3×200 uL). An additional aliquot of CH$_3$CN is added and concentrated under vacuum without heating. Prior to complete solvent removal, THF (150 uL) is added, the vial is uncrimped and (+/−)-11-nitrodeguelin (2 mg) is added in one portion. The vial is recapped and heated at 65° C. for 30 minutes. After cooling to room temperature, the vial is diluted with water (4 mL) and passed through a silica gel cartridge (pre-loaded Waters Light C-18 Sep-Pak) to load the sample. The cartridge is rinsed with water and eluted with CH$_3$CN (2 mL). The acetonitrile is evaporated and the residue is purified via HPLC to afford pure carrier-free (+/−)-11-[$^{18}$F]fluorodeguelin Synthesis of (+/−)-10-[$^{18}$F]fluorodeguelin

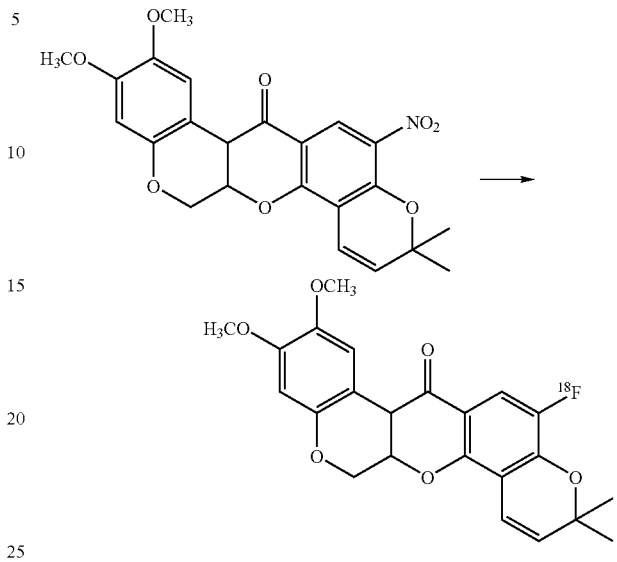

A thin-wall 10 mL, silanized vacutainer with a silanized stopper is charged with tetrabutyl ammonium hydroxide (5 uL, 40% w/v solution in water), and a solution of $^{18}$F$^−$ in water (10 mCi, 200 uL). The resultant mixture is evaporated to dryness under a flow of nitrogen at 100° C. The residue is further dried by repeated addition and evaporation of CH$_3$CN (3×200 uL). An additional aliquot of CH$_3$CN is added and concentrated under vacuum without heating. Prior to complete solvent removal, THF (150 uL) is added, the vial is uncrimped and (+/−)-10-nitrodeguelin (2 mg) is added in one portion. The vial is recapped and heated at 65° C. for 30 minutes. After cooling to room temperature, the vial is diluted with water (4 mL) and passed through a silica gel cartridge (pre-loaded Waters Light C-18 Sep-Pak) to load the sample. The cartridge is rinsed with water and eluted with CH$_3$CN (2 mL). The acetonitrile is evaporated and the residue is purified via HPLC to afford pure carrier-free (+/−)-10-[$^{18}$F]fluorodeguelin.

EXAMPLE 2

Tebufenpyrad Analogs

Synthesis 5-N-(4-tert-butylbenzyl)carboxamido-3-(methoxycarbonyl)-1-methylpyrazole

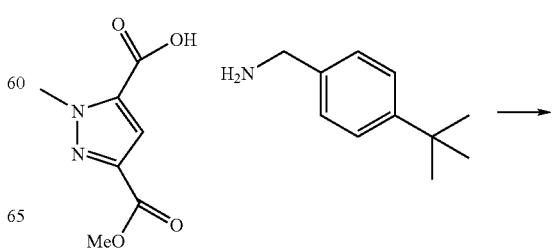

-continued

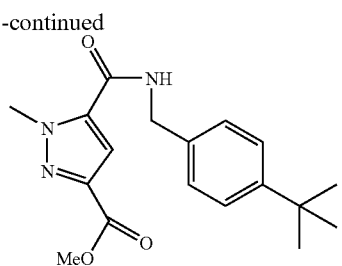

A mixture of 3-(methoxycarbonyl)-1-methyl-5-carboxylic acid (20 mmole) and thionyl chloride (30 mmole) is heated at reflux for 30 minutes. The excess thionyl chloride is removed under vacuum, and the residue dried via azeotrope with dry benzene. The resultant crude acyl chloride is dissolved in THF (10 mL) and stirred while cooling at 0 degrees C. while a solution of 4-tert-butylbenzylamine (22 mmole) and diisopropylethylamine (25 mmole) in THF (5 mL) is added dropwise. The reaction mixture is stirred at room temperature for 1 hour, and heated to reflux briefly to complete the reaction. The mixture is cooled and poured into ice-cold water (100 mL) and is extracted with ether (3×100 mL). The combined organics are dried (sat'd aq. NaCl, Na$_2$SO$_4$), filtered and concentrated. Purification of the residue via flash column chromatography (silica gel, gradient elution with 0-20% ethyl acetate/hexanes) affords 5-N-(4-tert-butylbenzyl)carboxamido-3-(methoxycarbonyl)-1-methylpyrazole.

Synthesis of Methyl 5-N-(4-tert-butyl)benzylcarboxamido-4-chloro-1 methyl-3-pyrazolylcarboxylate

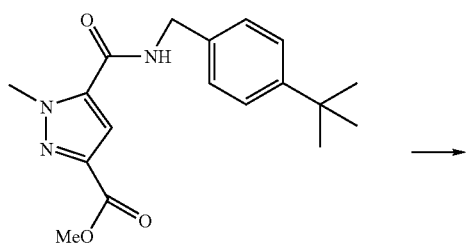

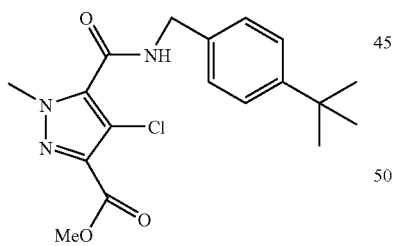

A solution of 5-N-(4-tert-butylbenzyl)carboxamido-3-(methoxycarbonyl)-1-methylpyrazole (0.1 mole) and thionyl chloride (0.13 mole) in 1,2-dichloroethane (15 mL) is heated at reflux for two hours. The reaction mixture is cooled and concentrated in vacuo. The residue is partitioned between dichloromethane (100 mL) and sat'd aq. NaHCO$_3$ (100 mL), ensuring the pH of the aqueous phase is >7. The aqueous layer is separated and extracted with dichloromethane (2×100 mL), and the combined organics are dried (sat'd aq. NaCl, Na$_2$SO$_4$), filtered and concentrated. Recrystallization of the residue (EtOH-water) affords pure methyl 5-N-(4-tert-butyl)benzylcarboxamido-4-chloro-1-methyl-3-pyrazolylcarboxylate.

Synthesis of 5-N-(4-tert-butyl)benzylcarboxamido-4-chloro-1-methyl-3-pyrazolyl carboxylic acid

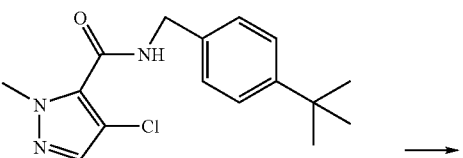

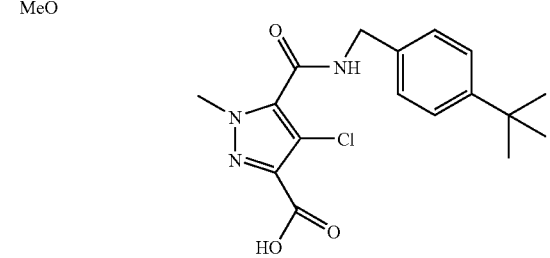

A solution of methyl 5-N-(4-tert-butyl)benzylcarboxamido-4-chloro-1-methyl-3-pyrazolylcarboxylate (50 mmole) in dioxane (33 mL) and water (75 mL) is treated with a solution of H$_2$SO$_4$ (conc., 1 mL) in water (1.5 mL). The resultant mixture is heated at reflux to exhaustion of the starting material. The resultant mixture is concentrated in vacuo to the saturation point (removal of the dioxane), and cooled at 0° C. overnight. The resultant precipitate is collected by filtration and dried. The filtrate is extracted with dichloromethane (3×100 mL) and the combined organics are dried (sat'd aq. NaCl, Na$_2$SO$_4$), filtered and concentrated. Recrystallization of the residue (ethyl acetate-methanol) affords pure 5-N-(4-tert-butyl)benzylcarboxamido-4-chloro-1-methyl-3-pyrazolyl carboxylic acid.

Synthesis of 1-(5-N-(4-tert-butyl)benzylcarboxamido-4-chloro-1-methyl-3-pyrazolyl)-1-ethanone

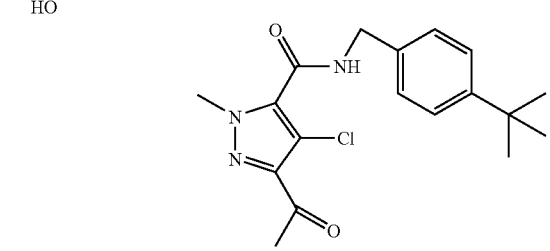

A solution of 5-N-(4-tert-butyl)benzylcarboxamido-4-chloro-1-methyl-3-pyrazolyl carboxylic acid (20 mmole) in thionyl chloride (30 mmole) is heated at reflux fo 15 minutes.

The mixture is cooled and concentrated in vacuo. Benzene (10 mL) is added, and removed first at atmospheric pressure, then under vacuum. The resultant acid chloride is used directly in the next step.

A flask is charged with solid anhydrous cuprous bromide (25 mmole), and flushed with argon. Tetrahydrofuran (125 mL) is added. The resultant suspension is cooled at −78° C. while a solution of methylmagnesium bromide (17.8 mL, 2.9M in diethyl ether) is added dropwise. The mixture is stirred while cooling at −78° C. for 20 minutes. The above prepared acid chloride is dissolved in THF (10 mL) and cooled to −78° C. The acid chloride is slowly added to the cuprate via cannula, allowing the addition solution to run down the side of the reaction flask for re-cooling. The acid chloride flask is rinsed with THF (5 mL), which is again cooled and added via cannula. The bath is removed and the mixture is stirred at room temperature for 30 minutes. Methanol (4 mL) is added to quench the reaction, and the mixture is poured into saturated aqueous NH$_4$Cl (200 mL). The mixture is stirred for one hour to dissolve the copper salts and the organic layer is separated. The aqueous phase is washed with dichloromethane (2×200 mL) and the combined organics are dried (sat'd aq. NaCl, Na$_2$SO$_4$), filtered and concentrated. The residue is purified via chromatography (silica gel, gradient elution 10-30% ethyl acetate-hexanes) to afford pure 1-(5-N-(4-tert-butyl)benzylcarboxamido-4-chloro-1-methyl-3-pyrazolyl)-1-ethanone.

Synthesis of 5-N-(4-tert-butyl)benzylcarboxamido-4-chloro-3-(1-hydroxyethyl)-1-methylpyrazoline

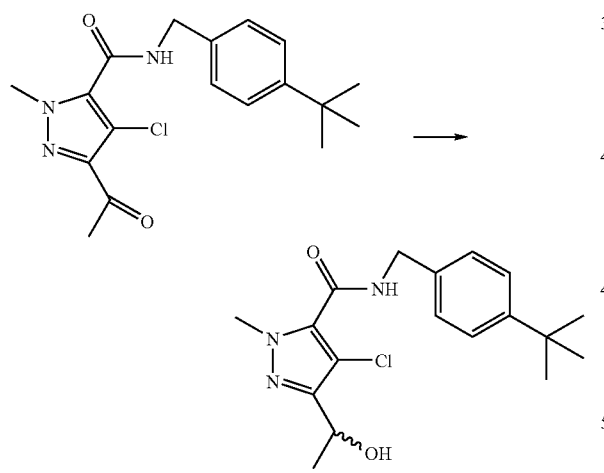

Sodium borohydride (20 mmole) is added as a solid in one portion to a stirred solution of 1-(5-N-(4-tert-butyl)benzyl-carboxamido-4-chloro-1-methyl-3-pyrazolyl)-1-ethanone (10 mmole) in ethanol (15 mL) at room temperature. The mixture is stirred to exhaustion of the starting ketone. More sodium borohydride is added if necessary. Water (2 mL) is added, the mixture concentrated and the mixture is partitioned between water (100 mL) and dichloromethane (2×100 mL). The combined organics are dried (sat'd aq. NaCl, Na$_2$SO$_4$), filtered and concentrated. The residue is purified via chromatography (silica gel, gradient elution 10-30% ethyl acetate-hexanes) to afford pure 5-N-(4-tert-butyl)benzyl carboxamido-4-chloro-3-(1-hydroxyethyl)-1-methylpyrazoline.

Synthesis of 5-N-(4-tert-butyl)benzylcarboxamido-4-chloro-1-methyl-3-(1-p-toluenesulfonatoethyl)pyrazoline

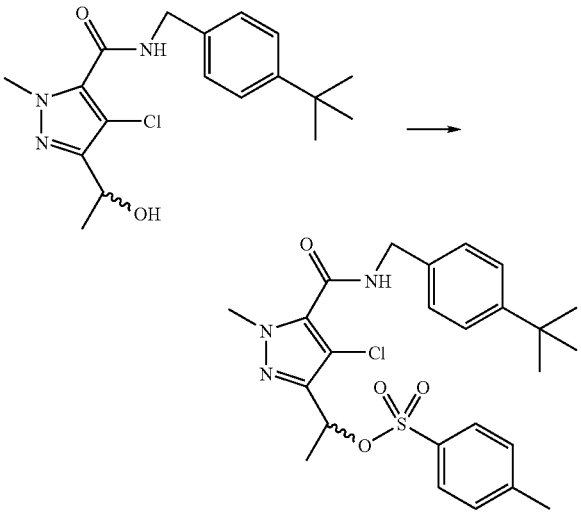

A solution of 5-N-(4-tert-butyl)benzyl carboxamido-4-chloro-3-(1-hydroxyethyl)-1-methylpyrazoline (5 mmole) and p-toluenesulfonyl chloride (5.5 mmole) in pyridine (12 mL) is stirred at room temperature for four hours. The solution is concentrated and is partitioned between water (100 mL) and dichloromethane (2×100 mL). The combined organics are dried (sat'd aq. NaCl, Na$_2$SO$_4$), filtered and concentrated. The residue is purified via chromatography (silica gel, gradient elution 2-20% ethyl acetate-hexanes) to afford pure 5-N-(4-tert-butyl)benzylcarboxamido-4-chloro-1-methyl-3-(1-p-toluenesulfonatoethyl)pyrazoline.

Synthesis of 5-N-(4-tert-butyl)benzylcarboxamido-4-chloro-1-methyl-3-(1-[$^{18}$F]fluoroethyl)pyrazoline (via tosylate)

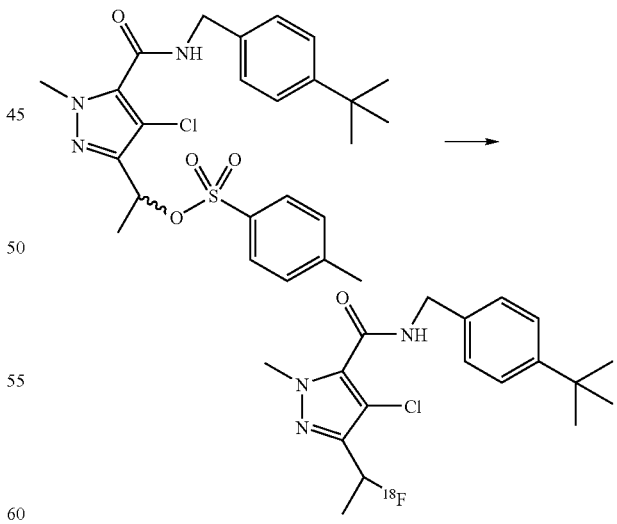

A thin-wall 10 mL, silanized vacutainer with a silanized stopper is charged with tetrabutyl ammonium hydroxide (5 uL, 40% w/v solution in water), and a solution of $^{18}$F in water (10 mCi, 200 uL). The resultant mixture is evaporated to dryness under a flow of nitrogen at 100° C. The residue is further dried by repeated addition and evaporation of CH$_3$CN (3×200 uL). An additional aliquot of CH₃CN is added and concentrated under vacuum without heating. Prior to complete solvent removal, THF (150 uL) is added, the vial is uncrimped and pure 5-N-(4-tert-butyl)benzylcarboxamido-4-chloro-1-methyl-3-(1-p-toluenesulfonatoethyl)pyrazoline (2 mg) is added in one portion as a solid. The vial is recapped and heated at 65° C. for 30 minutes. After cooling, the vial is diluted with water (4 mL) and passed through a silica gel cartridge (pre-loaded Waters Light C-18 Sep-Pak) to load the sample. The cartridge is rinsed with water and eluted with CH₃CN (2 mL). The acetonitrile is evaporated and the residue is purified via HPLC to afford pure carrier-free 5-N-(4-tert-butyl)benzylcarboxamido-4-chloro-1-methyl-3-(1-[¹⁸F]fluoroethyl)pyrazoline Synthesis of 5-N-(4-tert-butyl)benzylcarboxamido-4-chloro-1-methyl-3-(1-methanesulfonatoethyl)pyrazoline

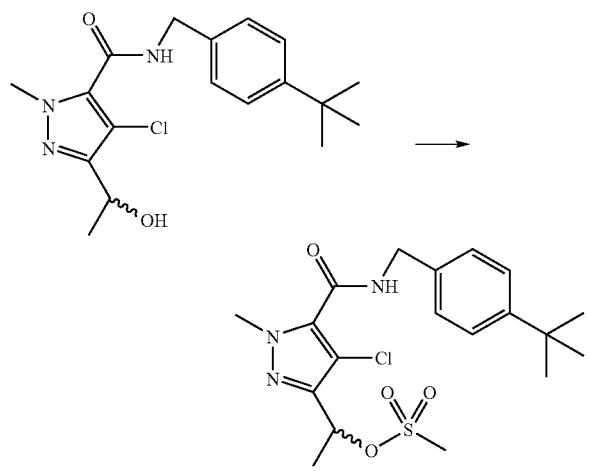

A solution of 5-N-(4-tert-butyl)benzyl carboxamido-4-chloro-3-(1-hydroxyethyl)-1-methylpyrazoline (5 mmole) and methanesulfonyl chloride (5.5 mmole) in pyridine (12 mL) is stirred at room temperature for four hours. The solution is concentrated and is partitioned between water (100 mL) and dichloromethane (2×100 mL). The combined organics are dried (sat'd aq. NaCl, Na₂SO₄), filtered and concentrated. The residue is purified via chromatography (silica gel, gradient elution 2-20% ethyl acetate-hexanes) to afford pure 5-N-(4-tert-butyl)benzylcarboxamido-4-chloro-1-methyl-3-(1-methanesulfonatoethyl)pyrazoline.

Synthesis of 5-N-(4-tert-butyl)benzylcarboxamido-4-chloro-1-methyl-3-(1-[¹⁸F]fluoroethyl)pyrazoline (via mesylate)

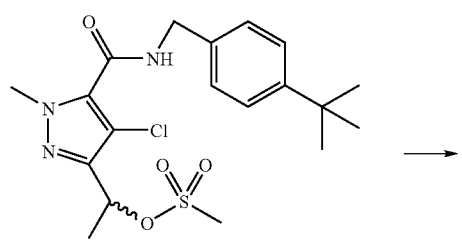

-continued

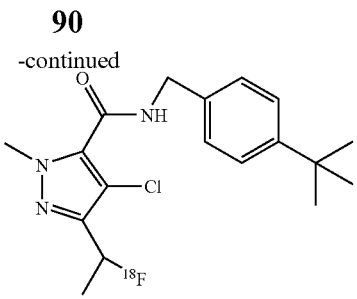

A thin-wall 10 mL, silanized vacutainer with a silanized stopper is charged with tetrabutyl ammonium hydroxide (5 uL, 40% w/v solution in water), and a solution of ¹⁸F⁻ in water (10 mCi, 200 uL). The resultant mixture is evaporated to dryness under a flow of nitrogen at 100° C. The residue is further dried by repeated addition and evaporation of CH₃CN (3×200 uL). An additional aliquot of CH₃CN is added and concentrated under vacuum without heating. Prior to complete solvent removal, THF (150 uL) is added, the vial is uncrimped and pure 5-N-(4-tert-butyl)benzylcarboxamido-4-chloro-1-methyl-3-(1-methanesulfonatoethyl)pyrazoline (2 mg) is added in one portion as a solid. The vial is recapped and heated at 65 degrees C. for 30 minutes. After cooling, the vial is diluted with water (4 mL) and passed through a silica gel cartridge (pre-loaded Waters Light C-18 Sep-Pak) to load the sample. The cartridge is rinsed with water and eluted with CH₃CN (2 mL). The acetonitrile is evaporated and the residue is purified via HPLC to afford pure carrier-free 5-N-(4-tert-butyl)benzylcarboxamido-4-chloro-1-methyl-3-(1-[¹⁸F]fluoroethyl)pyrazoline

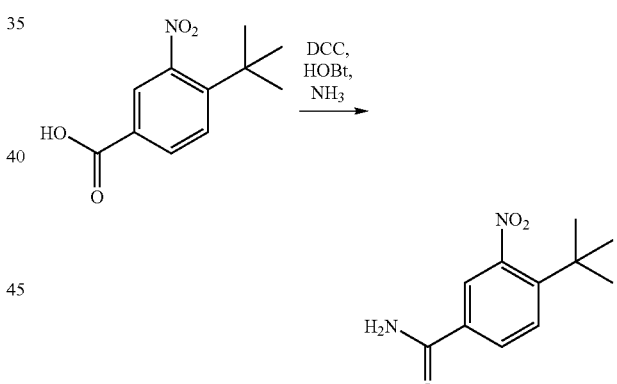

Synthesis of 4-tert-butyl-3-nitrobenzamide

A mixture of 4-tert-butyl-3-nitrobenzoic acid (0.1 mole), hydroxybenzotriazole (HOBt, 0.12 mole) and dicyclohexylcarbodiimide (DCC, 0.11 mole) in dichloromethane (100 mL) is stirred at room temperature while a solution of ammonia in 2-propanol (2.0M, 75 mL, 0.12 mole) is added rapidly. The mixture is stirred for two hours at room temperature, and poured into aqueous NaHCO₃ (5%, 200 mL). The layers are separated, and the aqueous phase is extracted with dichloromethane (2×200 mL). The combined organics are washed (2×200 mL 5% aq. NaHCO₃), dried (sat'd aq. NaCl, Na₂SO₄), filtered and concentrated. The product is recrystallized from EtOH-water to afford pure 4-tert-butyl-3-nitrobenzamide.

Synthesis of 4-tert-butyl-3-[$^{18}$F]fluorobenzylamine

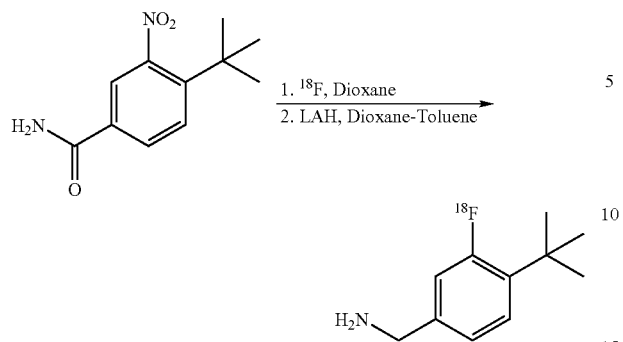

A thin-wall 10 mL, silanized vacutainer with a silanized stopper is charged with tetrabutyl ammonium hydroxide (5 uL, 40% w/v solution in water), and a solution of $^{18}$F$^-$ in water (10 mCi, 200 uL). The resultant mixture is evaporated to dryness under a flow of nitrogen at 100° C. The residue is further dried by repeated addition and evaporation of CH$_3$CN (3×200 uL). An additional aliquot of CH$_3$CN is added and concentrated under vacuum without heating. Prior to complete solvent removal, dioxane (150 uL) is added, the vial is uncrimped and 4-tert-butyl-3-nitrobenzamide (1 mg, ca. 4.5 umoles) is added in one portion as a solid. The vial is recapped and heated at 100° C. for 25 minutes. After cooling, a solution of lithium aluminum hydride bis(tetrahydrofuran) in toluene (1.0M, 50 uL, 50 umoles) is added, and the mixture is heated at 50 degrees C. for five minutes. The vial is cooled and the contents are diluted with water (4 mL) and passed through a silica gel cartridge (pre-loaded Waters Light C-18 Sep-Pak) to load the sample. The cartridge is rinsed with water and eluted with CH$_3$CN (2 mL). The acetonitrile is evaporated and the residue is purified via HPLC to afford pure carrier-free 4-tert-butyl-3-[$^{18}$F]fluorobenzylamine. The solvent is evaporated and the material is used directly in the following procedure.

Synthesis of 5-N-(4-tert-butyl-3-[$^{18}$F]fluoro)benzyl-carboxamido-4-chloro-3-ethyl-1-methylpyrazoline

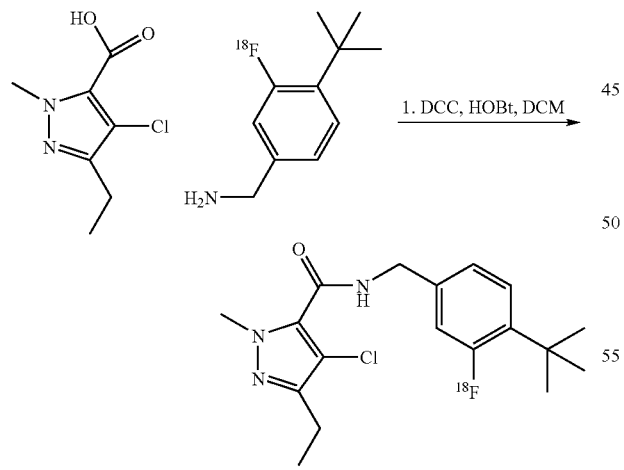

To a stirred mixture of 3-ethyl-1-methylpyrazole-5-carboxylic acid (50 umole), dicyclohexylcarbodiimide (DCC, 50 umole, delivered as an aliquot from a stock solution in dichloromethane), hydroxybenzotriazole (HOBt, 60 umole) in methylene chloride (200 uL), is added a solution of 4-tert-butyl-3-[$^{18}$F]fluorobenzylamine (prepared above) in dichloromethane (100 uL). The mixture is stirred at room temperature for ten minutes at room temperature, concentrated and dissolved in acetonitrile-water (1:4, 3 mL). The mixture is passed through a silica gel cartridge (pre-loaded Waters Light C-18 Sep-Pak) to load the sample. The cartridge is rinsed with water and eluted with CH$_3$CN (2 mL). The acetonitrile is evaporated and the residue is purified via HPLC to afford pure carrier-free 5-N-(4-tert-butyl-3-[$^{18}$F] fluoro)benzylcarboxamido-4-chloro-3-ethyl-1-methylpyrazoline.

EXAMPLE 3

Pyridaben Analogs

Synthesis of 2-tert-butyl-4,5-dichloro-3(2H)-pyridazinone

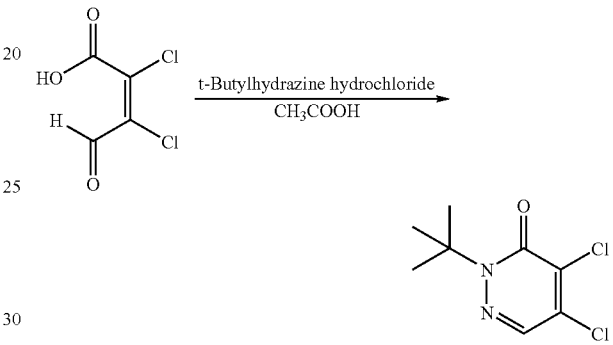

To mucochloric acid (4.0 g, 23.6 mmol) in water (35 ml) at 0° C. was added anhydrous Na$_2$CO$_3$ (1.21 g, 11.5 mmol). This was stirred till a clear solution was obtained and to this was added tert-butylhydrazine hydrochloride (2.94 g, 23.6 mmol). A precipitate started to form after a few minutes. The reaction was stirred for a further 2.5 hrs after which it was filtered. The yellow precipitate was washed with cold water and dried to give 4.81 g of the crude hydrazone.

To 4.32 g of the crude hydrazone was added 40 ml of acetic acid and the solution was refluxed for 25 minutes. The solution was then cooled and concentrated. This was then taken up in dichloromethane and washed with 1M sodium carbonate and water. The organic layer was then dried and concentrated to give a yellow solid which was purified by column chromatography using hexanes:chloroform (1:1 to 0:100)as the eluting solvent. This afforded 2.4 g of the above as a white solid.

Synthesis of 2-tert-Butyl-4-chloro-5-thio-3(2H)-pyridazinone

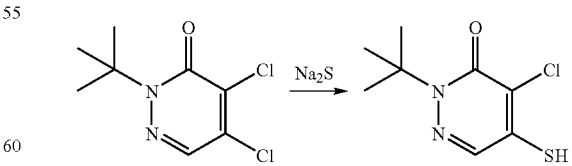

To 0.5 g of 2-tert-Butyl-4,5-dichloro-3(2H)-pyridazinone was added 7 ml water and sodium sulfide (0.53 g, 6.81 mmol) and the mixture was heated to 80° C. until all the solid dissolved. The solution was then cooled to room temperature and concentrated HCl was carefully added to give a yellow precipitate, which was filtered and washed with cold water. Crystallization from hexanes afforded the product as a white solid (270 mg).

Synthesis of 2-tert-butyl-4-chloro-5-(4-tert-butylbenzyl) thio 3(2H)-pyridazinone

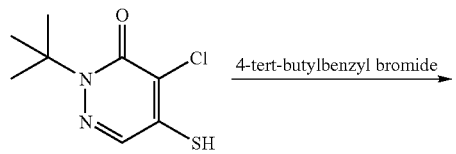

To 220 mg of 2-tert-butyl-4-chloro-5-thio-3(2H)-pyridazinone in 4 ml DMF was added 4-tert-butylbenzyl bromide (226 mg, 1 mmol) and Na$_2$CO$_3$. The reaction mixture was stirred for 16 hrs at room temperature after which it was extracted in ethyl acetate, washed with water and purified by column chromatography (silica gel; ethyl acetate/hexanes) as the eluent. This afforded the above mentioned compound.

Synthesis of 2-tert-butyl-4-fluoro-5-(4-tert-butylbenzyl)thio 3(2H)-pyridazinone

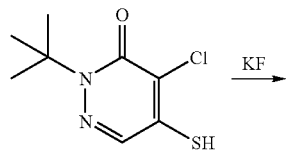

A round bottom flask is charged with 2-tert-butyl-4-chloro-5-(4-tert-butylbenzyl)thio 3(2H)-pyridazinone (100 mg, 0.27 mmol) and to it is added potassium fluoride (23.4 mg, 0.40 mmol) and 2 ml dimethyl sulfoxide. This is heated to 120° C. for 6 hours. The reaction mixture is then poured into water and extracted with ethyl acetate. This is washed with water and dried. Purification by flash chromatography (silica gel; ethyl acetate/hexanes) gave the above mentioned compound.

Synthesis of 2-tert-butyl-4-[$^{18}$F]-fluoro-5-(4-tert-butylbenzyl)thio 3(2H)-pyridazinone To a 5 ml reaction vial containing 500 mCi of $^{18}$F in 350 mg of $^{18}$ water is added a 1 ml solution consisting of 10 mg of Kryptofix, 1 mg potassium carbonate, 0.005 ml water and 0.95 ml acetonitrile. The vial is heated to remove all the solvents and dry acetonitrile (1 ml) is added to the vial. This is also removed by evaporation. 2-tert-butyl-4-chloro-5-(4-tert-butylbenzyl)thio 3(2H)-pyridazinone (5 mg) in acetonitrile is then added to it. The vial is sealed and heated for 30 minutes at 100° C. The mixture is diluted with dichloromethane and passed through a Sep-Pak and eluted with tetrahydrofuran. The solvent is evaporated to get the above mentioned compound.

Synthesis of 4-(4-Methylphenyl)butanol

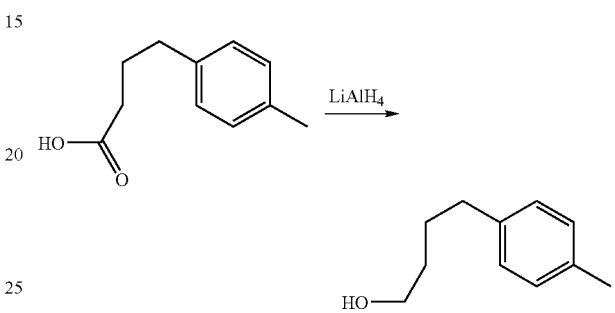

To lithium aluminum hydride (427 mg, 11.2 mmol) suspended in dry ether (5 ml) at 0° C. is added 1 g of 4-(4-methylphenyl)butanoic acid (5.614 mmol) dissolved in dry ether (10 ml) over a period of 30 minutes. The reaction mixture is then warmed to room temperature and stirred for 4 hours. Water (0.43 ml), NaOH (15% solution, 0.43 g) and water (1.29 ml) are then added successively and the resulting solution is stirred for 30 minutes. The precipitate is filtered and washed with ether and dried. This is then concentrated and purified by flash chromatography (silica gel; ethyl acetate/hexanes) as the eluting medium.

Synthesis of 4-(4-methylphenyl)-butyl tert-butyldimethylsilyl ether

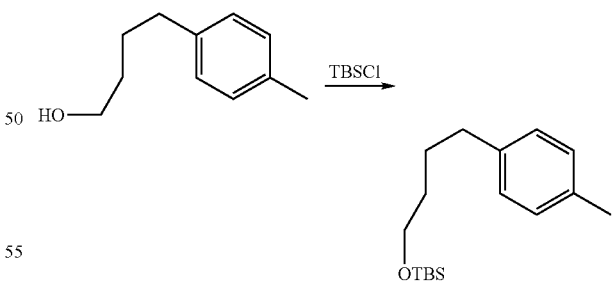

4-(4-Methylphenyl)butanol (0.5 g, 3.04 mmol) is dissolved in 5 ml DMF and to it is added imidazole (310 mg, 4.56 mmol) and tert-butyldimethylsilyl chloride (685 mg, 4.56 mmol). The reaction is stirred for 4 hrs after which it is extracted in ethyl acetate and washed with water to remove all DMF. The organic layer is then dried and concentrated. The crude mixture is then purified by flash chromatography using a mixture of ethyl acetate-hexanes as the eluting medium to afford the above mentioned product.

Synthesis of 4-(4-bromomethylphenyl)butyl tert-butyldimethylsilyl ether

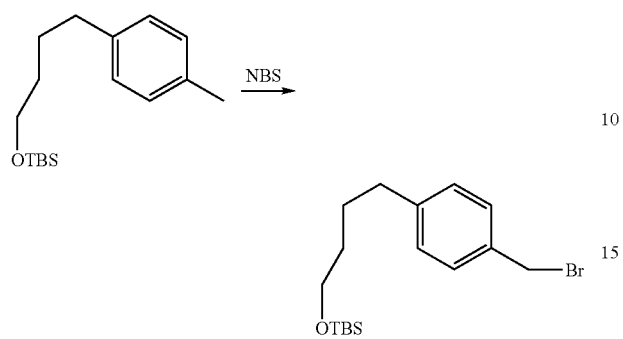

To a 50 ml round bottom flask is added 4-(4-methylphenyl) butyl tert-butyldimethylsilyl ether (0.25 g, 0.89 mmol), N-bromosuccinimide (0.158 g, 0.89 mmol), benzoyl peroxide (2.17 mg, 0.0089 mmol) and 10 ml carbon tetrachloride. This mixture is refluxed overnight after which it is cooled and filtered. The filtrate is concentrated and the resulting crude residue is purified by flash chromatography in ethyl acetate-hexanes to afford the product.

Synthesis of 2-tert-butyl-4-chloro-5-(4-(4-tert-butyldimethylsilyloxy butyl)benzyl)thio-3(2H)-pyridazinone

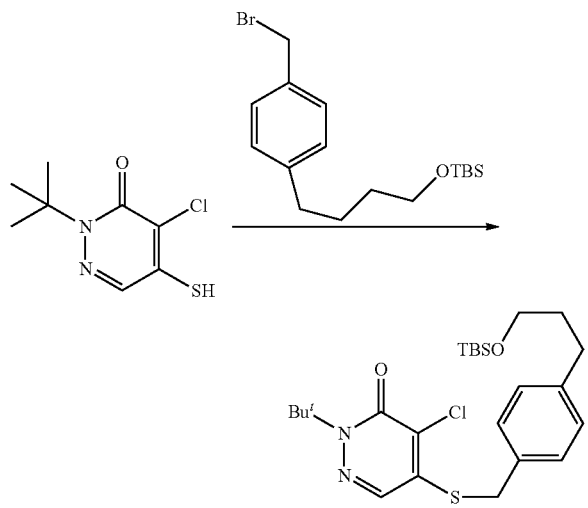

To a flask containing 2-tert-butyl-4-chloro-5-thio-3(2H)-pyridazinone (0.2 g, 0.917 mmol) is added 5 ml DMF followed by cesium carbonate (0.358 g, 1.1 mmol) and 4-(4-bromomethylphenyl)-butyl tert-butyldimethylsilyl ether (0.391 g, 1.1 mmol). The mixture is heated to 60° C. for 2 hrs after which it is cooled, extracted in ethyl acetate, washed, dried and concentrated. The crude mixture is then purified by chromatography using silica gel and a mixture of ethyl acetate—hexanes as the eluent. This affords the above mentioned product.

Synthesis of 2-tert-butyl-4-chloro-5-(4-(4-hydroxybutyl)benzyl)thio-3(2H) pyridazinone

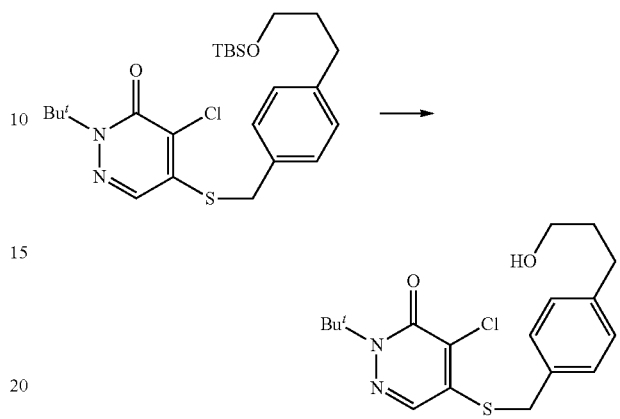

To 0.2 g 2-tert-butyl-4-chloro-5-(4-(4-tert-butyldimethylsilyloxy butyl)benzyl)thio-3(2H)-pyridazinone (0.404 mmol) is added 5 ml of 1% concd. HCl

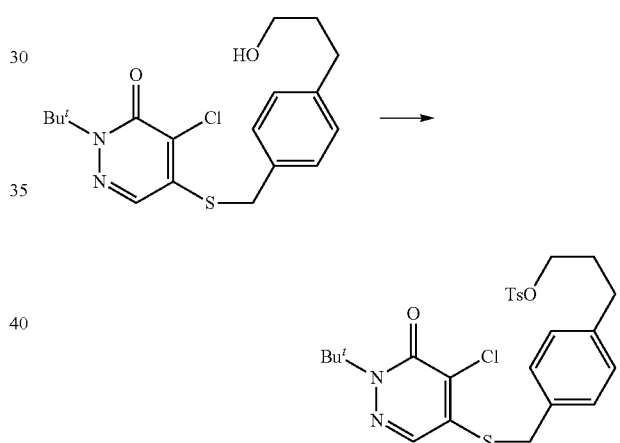

in ethanol. The reaction mixture is stirred for 30 minutes after which it is extracted in ethyl acetate, washed with water and dried. Purification (silica gel; EtOAC/hexanes) of the crude mixture obtained after concentration yields the desired product

Synthesis of 2-tert-butyl-4-chloro-5-(4-(4-toluenesulfonyloxybutyl)benzyl)thio-3(2H)-pyridazinone To a 15 ml round bottom flask charged with 2-tert-butyl-4-chloro-5-(4-(4-hydroxybutyl)benzylithio-3(2H)-pyridazinone (0.15 g, 0.39 mmol) is added pyridine. Toluenesulfonyl chloride (88.9 mg, 0.42 mmol) is then added to it and the mixture stirred for 2 hours. The reaction mixture is diluted with ethyl acetate, washed with 5% copper sulfate solution and then with water and dried. After removing the solvent on the rotary evaporator the crude is purified by flash chromatography using ethyl acetate—hexanes as the eluting mixture.

Synthesis of 2-tert-butyl-4-chloro-5-(4-(4-fluorobutyl)benzyl)thio-3(2H)-pyridazinone

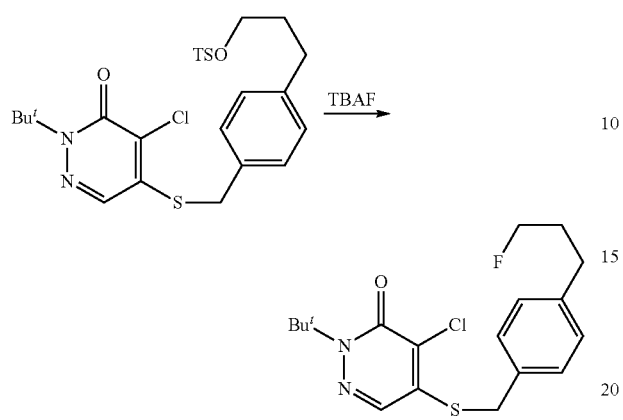

To a round bottom flask is added 2-tert-butyl-4-chloro-5-(4-(4-toluenesulfonyloxybutyl)benzyl)thio-3(2H)-pyridazinone (0.05 g, 0.093 mmol) and to it is added tetrabutylammonium fluoride (1.0 M solution in THF, 0.93 μl, 0.93 mmol) followed by 0.2 ml of THF. The reaction is heated to 60 C and stirred at that temperature for 30 minutes. The mixture is then cooled and concentrated and the crude subjected to flash chromatography to obtain the above mention compounds

Synthesis of 2-tert-butyl-4-chloro-5-(4-(4-[$^{18}$F]-fluorobutyl)benzyl)thio-3(2H)-pyridazinone

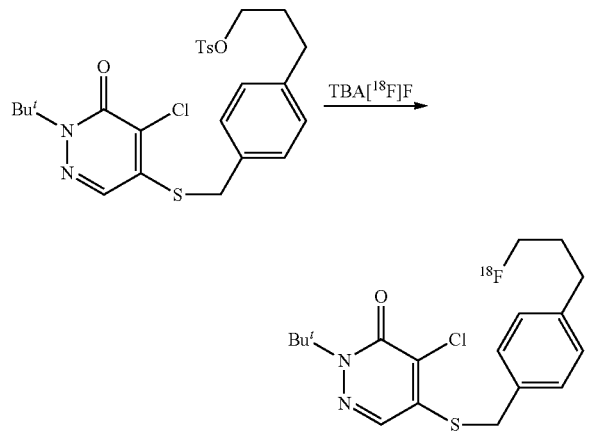

Aqueous $^{18}$F (16 mCi, 0.1 ml) is added to a vacutainer containing 5 μl of tetrabutylammonium hydroxide (40% wt sol. in water). The mixture is concentrated under nitrogen in an oil bath and 250 μl of acetonitrile is added and this too is concentrated under nitrogen. 100 μl of THF is then added to it followed by 5 mg of 2-tert-butyl-4-chloro-5-(4-(4-toluenesulfonyloxybutylabenzyl)thio-3(2H)-pyridazinone. The mixture is then heated in an oil bath at 70° C. for 30 minutes. This is then diluted with water, applied to a C18Sep-Pak and eluted with acetonitrile to get the above mentioned compound.

Synthesis of (4-tert-butylphenyl)ethane 1,2 diol

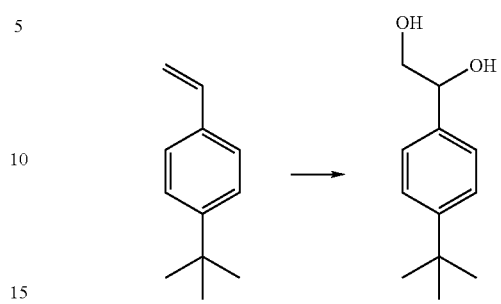

To a 100 ml round bottom flask is added 20 ml tert butanol, 20 ml of water and 5.6 g of AD-mix-β. The solution is stirred and cooled to 0 C. tert-butyl styrene (0.64 g, 4 mmol) is added to the mixture and the resulting solution is stirred overnight at 0° C. Solid sodium sulfite (6 g) is added and the mixture stirred for an additional 30 minutes. The solution is then extracted in ethyl acetate, washed with water and dried. The crude is then purified by flash chromatography (silica gel; ethyl acetate/hexanes) to afford the product.

Synthesis of 1-tert-butyldimethylsilyloxy-2-hydroxy-2-(4-tertbutylphenyl)ethane

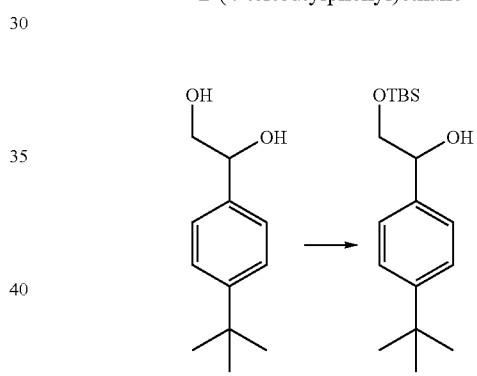

(4-tert-butylphenyl)ethane 1,2 diol (0.5 g, 2.57 mmol) is dissolved in DMF in a 25 ml round bottom flask and to this were added imidazole (0.210 g, 3.09 mmol) and tert-butyldimethylsilyl chloride (0.46 g, 3.09 mmol). The mixture is stirred for 6 hours after which it is extracted in dichloromethane and the organic layer washed with water and dried. Purification by flash chromatography (silica gel; ethyl acetate/hexanes) affords the above mentioned product.

Synthesis of 2-tert-butyl-4-chloro-5-(2-tert-butyldimethylsilyloxy-1-(4-tert-butylphenyl)-1-ethyl)oxy-3(2H)-pyridazinone

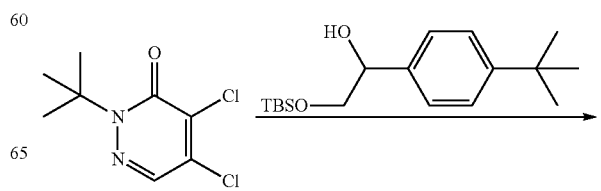

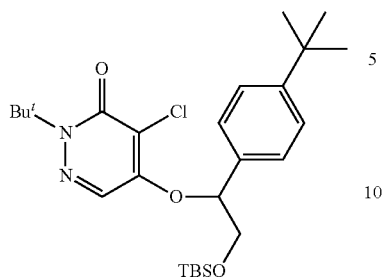

To a solution of 2-tert-butyl-4,5-dichloro-3(2H)-pyridazinone (0.5 g, 2.27 mmol) in DMP (10 ml) were added anhydrous cesium carbonate (0.74 g, 2.27 mmol) and 1-tert-butyldimethylsilyloxy 2-hydroxy 2-(4-tertbutylphenyl)ethane (0.7 g, 2.27 mmol). The mixture is stirred for 2 hours at 70° C. and then cooled to room temperature and ethyl acetate is added to it. The solution is then washed with water, dried and concentrated and the residue subjected to purification by flash chromatography (silica gel; ethyl acetate/hexanes) to give the above compound.

Synthesis of 2-tert-butyl-4-chloro-5-(2-hydroxy-1-(4-tert-butylphenyl)-1-ethyl)oxy-3(2H)-pyridazinone

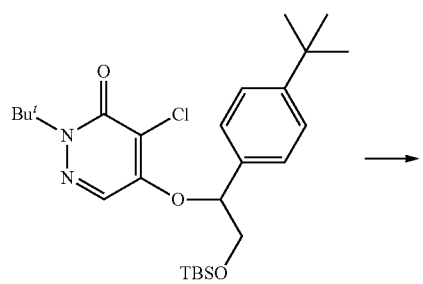

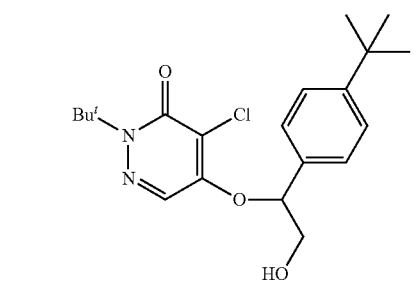

A 25 ml round bottom flask is charged 2-tert-butyl-4-chloro-5-(2-tert-butyldimethylsilyloxy-1-(4-tert-butylphenyl)-1-ethyl)oxy-3(2H)-pyridazinone (0.5 g, 1.01 mmol) and to it is added 5 ml of 1% concd. HCl in ethanol. The solution is stirred for one hour after which it is poured in water and extracted with ethyl acetate. The ethyl acetate is removed using the rotary evaporator and subjected to flash chromatography using silica gel and ethyl acetate/hexanes mixture as the eluting medium.

Synthesis of 2-tert-butyl-4-chloro-5-(2-p-toluene-sulfonyloxy-1-(4-tert-butylphenyl)-1-ethyl)oxy-3(2H)-pyridazinone

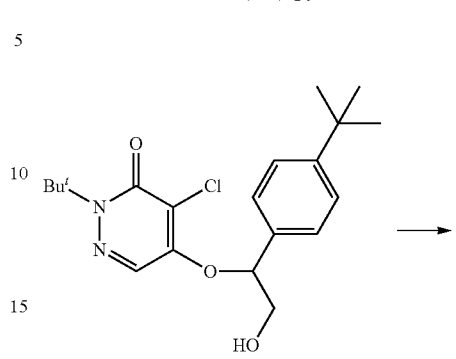

To a 15 ml round bottom flask charged with 2-tert-butyl-4-chloro-5-(2-hydroxy-1-(4-tert-butylphenyl)-1-ethyl)oxy-3(2H)-pyridazinone (0.25 g, 0.66 mmol) is added pyridine. Toluenesulfonyl chloride (0.15 g, 0.79 mmol) is then added to it and the mixture stirred for 4 hours. The reaction mixture is diluted with ethyl acetate, washed with 5% copper sulfate solution and then with water and dried. After removing the solvent on the rotary evaporator the crude is purified by flash chromatography using ethyl acetate—hexanes as the eluting mixture.

Synthesis of 2-tert-butyl-4-chloro-5-(2-fluoro-1-(4-tert-butylphenyl)-1-ethyl)oxy-3(2H)-pyridazinone

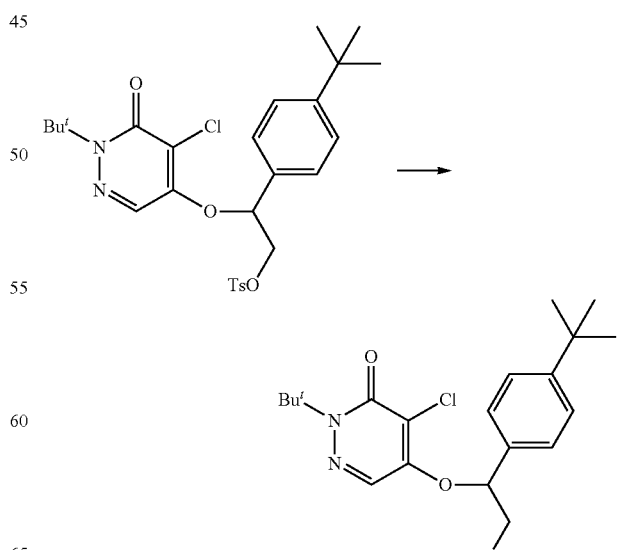

To a 15 ml round bottom flask charged with 2-tert-butyl-4-chloro-5-(2-p-toluenesulfonyloxy-1-(4-tert-butylphenyl)-1-ethyl)oxy-3(2H)-pyridazinone (0.2 g, 0.375 mmol) is added 3.75 ml of tetrabutylammonium fluoride solution (1M in THF, 3.75 mmol). The mixture is first stirred at room temperature for 15 minutes after which it is heated for 15 minutes at 100° C. The solution is then cooled to room temperature and to it is added dichloromethane followed by water. The layers were separated and the organic layer is washed with water and then dried. The organic layer is then concentrated and subjected to purification using silica gel flash chromatography (ethyl acetate/hexanes) to obtain the above compound.

Synthesis of 2-tert-butyl-4-chloro-5-(2-[$^{18}$F]-fluoro-1-(4-tert-butylphenyl)-1-ethyl)oxy-3(2H)-pyridazinone

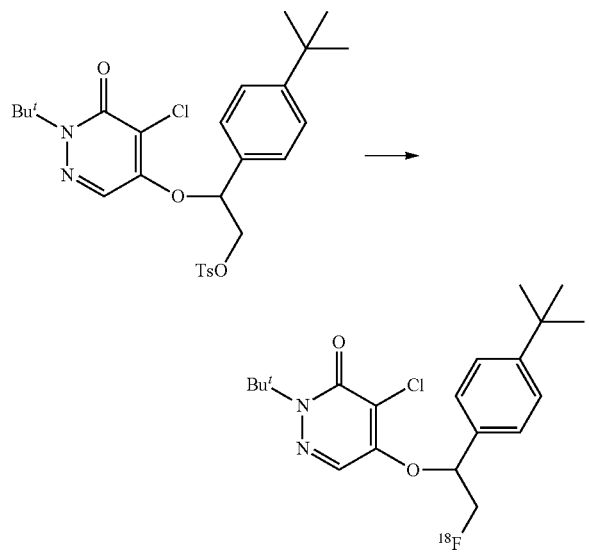

Aqueous $^{18}$F (16 mCi, 0.1 ml) is added to a vacutainer containing 5 μl of tetrabutylammonium hydroxide (40% wt sol. in water). The mixture is concentrated under nitrogen in an oil bath and 250 μl of acetonitrile is added and this too is concentrated under nitrogen. 100 μl of THF is then added to it followed by 5 mg of 2-tert-butyl-4-chloro-5-(2-p-toluenesulfonyl)oxy-1-(4-tert-butylphenyl)-1-ethyloxy-3(2H)-pyridazinone. The mixture is then heated in an oil bath at 70° C. for 30 minutes. This is then diluted with water, applied to a C18 Sep-Pak and eluted with acetonitrile to get the above mentioned compound.

Synthesis of 2-tert-butyl-4-methyl-5-chloro 3(2H)-pyridazinone

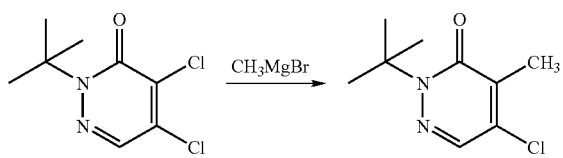

2-tert-butyl-4,5-dichloro-3(2H)-pyridazinone (5 g, 22.72 mmol) dissolved in 12 ml of ether was added dropwise to 15 ml of a ether solution of methylmagnesium bromide (3M in ether) at 5° C. was added. After completion of addition the solution was stirred at 5° C. for 2 hours. 10 ml of 6N HCl solution is then added slowly to it and the solution is stirred for 10 minutes. The mixture is then extracted with diethyl ether. The ether layer is then washed with water and dried. The crude product obtained after concentrating the ether is subjected to flash chromatography (silica gel; ethyl acetate/hexanes:9:1) to give the product.

Synthesis of 2-tert-butyl-4-bromomethyl-5-chloro 3(2H)-pyridazinone

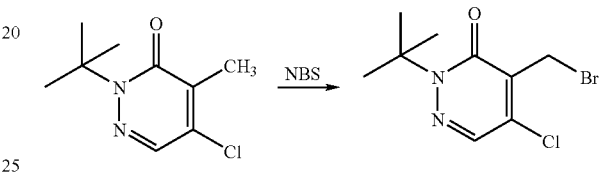

2-tert-butyl-4-methyl-5-chloro 3(2H)-pyridazinone (3 g, 15 mmol) is dissolved in 25 ml of carbon tetrachloride and to it is added N-bromosuccinimide (2.6 g, 15 mmol) and benzoyl peroxide (14 mg). The mixture is then refluxed for 6 hours after which it is cooled and filtered. The filtrate is washed with water and dried. After removing the organic solvent the crude residue obtained is purified by flash chromatography (silica gel; ethyl acetate/hexanes:9:1) to obtain the product.

Synthesis of 2-tert-butyl-4-hydroxymethyl-5-chloro 3(2H)-pyridazinone

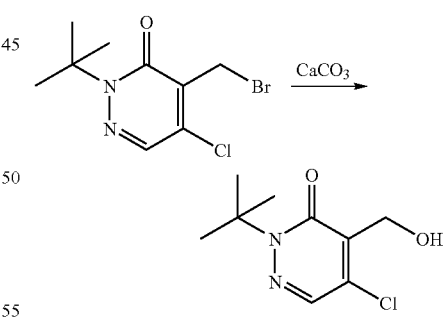

2-tert-butyl-4-bromomethyl-5-chloro 3(2H)-pyridazinone (2 g, 7.19 mmol) and calcium carbonate (3.5 gm) are added to a 1:1 mixture of dioxane water (40 ml). The mixture is refluxed for 6 hours after which 30 ml of 3N HCl solution is added to it. The solution is stirred for 10 minutes after which dioxane is removed under reduced pressure. The resulting solution is then extracted with dichloromethane and the dichloromethane layer is washed and dried. The crude obtained after concentration is purified by flash chromatography (ethyl acetate/hexanes:1:2).

Synthesis of 2-tert-butyl-4-tert-butyldimethylsilyloxymethyl-5-chloro 3(2H)-pyridazinone

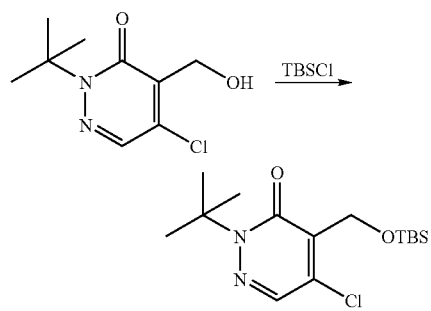

2-tert-butyl-4-hydroxymethyl-5-chloro 3(2H)-pyridazinone (1 g, 4.62 mmol) is dissolved in DMF in a 25 ml round bottom flask and to this were added imidazole (0.377 g, 5.0 mmol) and tert-butyldimethylsilyl chloride (0.762 g, 3.09 mmol). The mixture is stirred for 10 hours after which it is extracted in dichloromethane and the organic layer washed with water and dried. Purification by flash chromatography (silica gel; ethyl acetate/hexanes) affords the above mentioned product.

Synthesis of 2-tert-butyl-4-tert-butyldimethylsilyloxymethyl-5-(4-tert-butylbenzyl)thio-3(2H)-pyridazinone

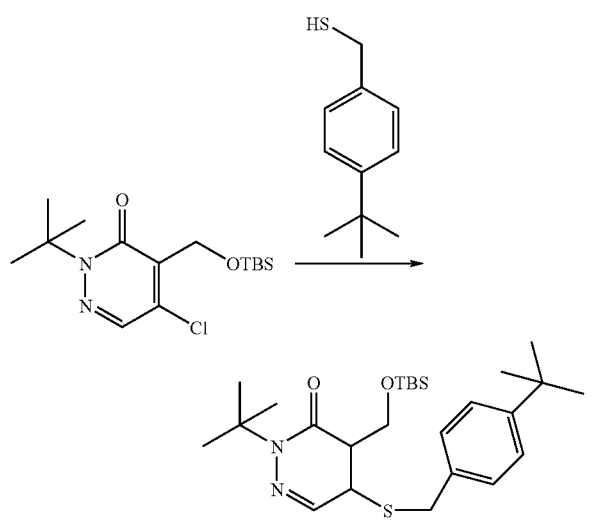

To a solution of 2-tert-butyl-4-tert-butyldimethylsilyloxymethyl-5-chloro 3(2H)-pyridazinone (1.5 g, 4.54 mmol) in DMF (10 ml) is added anhydrous cesium carbonate (2.9 g, 9.09 mmol) and 4-tert-butybenzyl mercaptan (1.02 g, 4.54 mmol). The mixture is stirred for 2 hours at 70° C. and then cooled to room temperature and ethyl acetate is added to it. The solution is then washed with water, dried and concentrated and the residue subjected to purification by flash chromatography (silica gel; ethyl acetate/hexanes) to give the above compound.

Synthesis of 2-tert-butyl-4-hydroxymethyl-5-(4-tert-butylbenzyl)thio-3(2H)-pyridazinone

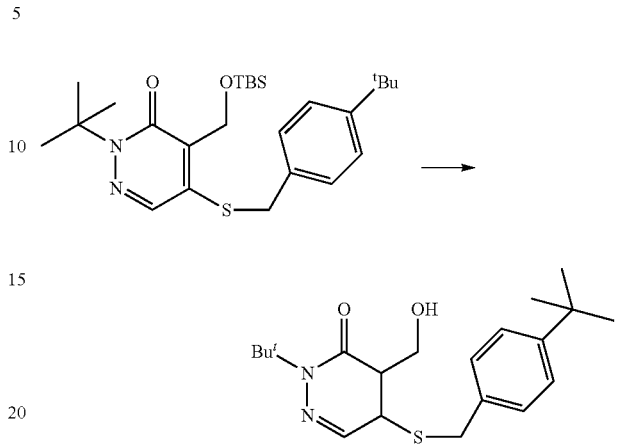

To a 15 ml round bottom flask charged with 2-tert-butyl-4-tert-butyldimethylsilyloxymethyl-5-(4-tert-butylbenzyl)thio-3(2H)-pyridazinone (2 g, 4.2 mmol) is added tetrabutylammonium fluoride solution (1M in THF, 21 ml, 21 mmol). The mixture is first stirred at room temperature for 5 hours and to it is added dichloromethane followed by water. The layers are separated and the organic layer is washed with water and dried. The organic layer is then concentrated and subjected to purification using silica gel flash chromatography (ethyl acetate/hexanes) to obtain the above compound.

Synthesis of 2-tert-butyl-4-p-toluenesulfonyloxymethyl-5-(4-tert-butylbenzyl)thio-3(2H)-pyridazinone

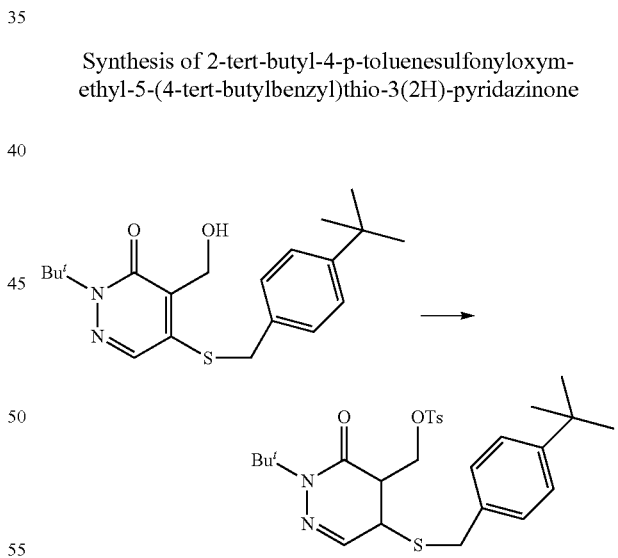

To a 15 ml round bottom flask charged with 2-tert-butyl-4-hydroxymethyl-5-(4-tert-butylbenzyl)thio-3(2H)-pyridazinone (1.0 g, 2.77 mmol) is added pyridine. p-Toluenesulfonyl chloride (0.79 g, 4.15 mmol) is then added to it and the mixture stirred for 4 hours. The reaction mixture is diluted with ethyl acetate, washed with 5% copper sulfate solution and then with water and dried. After removing the solvent on the rotary evaporator the crude is purified by flash chromatography using (silica gel; ethyl acetate/hexanes) as the eluting mixture to give the product.

Synthesis of 2-tert-butyl-4-fluoromethyl-5-(4-tert-butylbenzyl)thio-3(2H)-pyridazinone

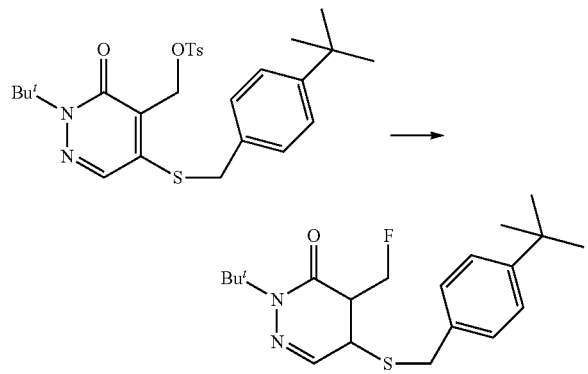

To a 15 ml round bottom flask charged with 2-tert-butyl-4-p-toluenesulfonyloxymethyl-5-(4-tert-butylbenzyl)thio-3(2H)-pyridazinone (0.5 g, 0.972 mmol) is added 4.86 ml of tetra-butylammonium fluoride solution (1M in THF, 4.86 mmol). The mixture is first stirred at room temperature for 15 minutes after which it is heated for 15 minutes at 100° C. The solution is then cooled to room temperature and to it is added dichloromethane followed by water. The layers were separated and the organic layer is washed with water and then dried. The organic layer is then concentrated and subjected to purification using silica gel flash chromatography (ethyl acetate/hexanes) to obtain the above compound.

Synthesis of 2-tert-butyl-4-[$^{18}$F]fluoromethyl-5-(4-tert-butylbenzyl)thio-3(2H)-pyridazinone

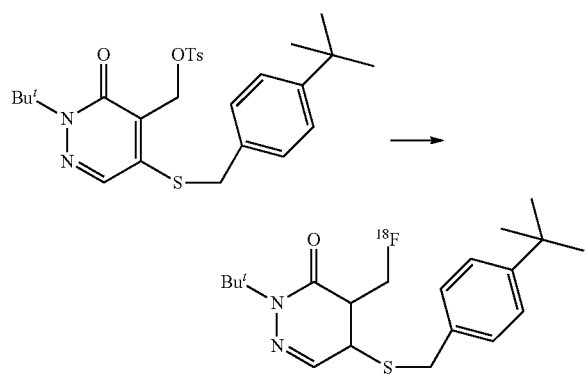

Aqueous $^{18}$F (50 mCi, 0.1 ml) is added to a vacutainer containing 5 μl of tetrabutylammonium hydroxide (40% wt sol. in water). The mixture is concentrated under nitrogen in an oil bath and 250 μl of acetonitrile is added and this too is concentrated under nitrogen. 100 μl of THF is then added to it followed by 5 mg of 2-tert-butyl-4-p-toluenesulfonyloxymethyl-5-(4-tert-butylbenzyl)thio-3(2H)-pyridazinone. The mixture is then heated in an oil bath at 70° C. for 30 minutes. This is then diluted with water, applied to a C18 Sep-Pak and eluted with acetonitrile to get the above mentioned compound.

EXAMPLE 4

Fenazaquin Analogs

Synthesis of 4-Chloro quinazoline

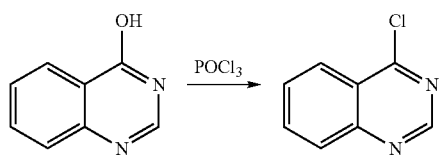

4-Quinazolone (5 g, 34.2 mmol), phosphorus pentachloride (10.26 g, 47.9 mmol) and phosphorus oxychloride (40 ml) were refluxed for two hours at 115-118° C. The phosphorus oxychloride was removed in vacuo and the residue was extracted in ether. The entire mixture was then poured into a vessel containing crushed ice and again extracted with ether. The ether layer was then washed with sodium bicarbonate and dried. The ether was then removed under reduced pressure and the crude material was recrystallized from hexanes to afford the product.

Synthesis of 4-(4-Methylphenyl)butanol

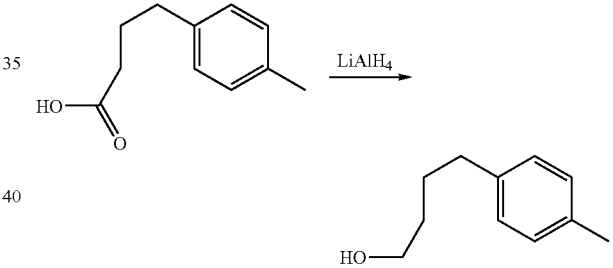

To lithium aluminum hydride (427 mg, 11.2 mmol) suspended in dry ether (5 ml) at 0° C. is added 1 g of 4-(4-methylphenyl)butanoic acid (5.614 mmol) dissolved in dry ether (10 ml) over a period of 30 minutes. The reaction mixture is then allowed to warm to room temperature and stirred for 4 hours. Water (0.43 ml), NaOH (15% solution, 0.43 g) and water (1.29 ml) were then added successively and the resulting solution is stirred for 30 minutes. The resulting precipitate is filtered and washed with ether and dried. The filtrate is then concentrated and purified by flash chromatography using ethyl acetate—hexanes as the eluting medium.

Synthesis of 4-(4-methylphenyl)butyl tert-butyldimethylsilyl ether

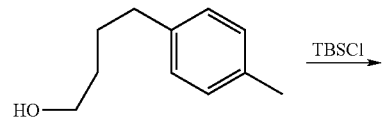

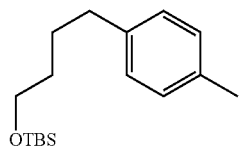

4-(4-Methylphenyl)butanol (0.5 g, 3.04 mmol) is dissolved in 5 ml DMF and to it is added imidazole (310 mg, 4.56 mmol) and tert-butyldimethylsilyl chloride (685 mg, 4.56 mmol). The reaction is stirred for 4 hrs after which it is extracted in ethyl acetate and washed with water to remove all DMF. The organic layer is then dried and concentrated. The crude mixture is then purified by flash chromatography using a mixture of ethyl acetate-hexanes as the eluting medium to afford the above mentioned product.

Synthesis of 4-(4-bromomethylphenyl)butyl tert-butyldimethylsilyl ether

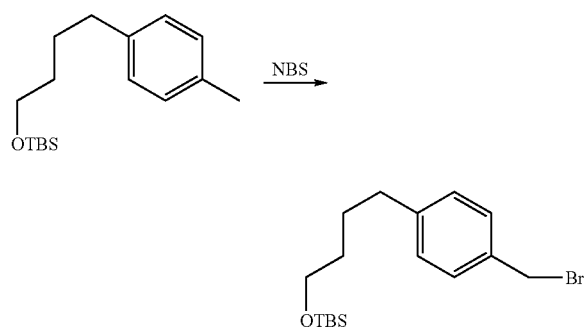

To a 50 ml round bottom flask is charged 4-(4-methylphenyl)butyl tert-butyldimethylsilyl ether (0.25 g, 0.89 mmol), N-bromosuccinimide (0.158 g, 0.89 mmol), benzoyl peroxide (2.17 mg, 0.0.89 mmol) and 10 ml carbon tetrachloride. This mixture is refluxed overnight after which it is cooled and filtered. The filtrate is concentrated and the resulting crude residue purified by flash chromatography in ethyl acetate-hexanes to afford the product.

Synthesis of 4-(4-tert-butyldimethylsilyloxybutyl)phenylacetic acid:

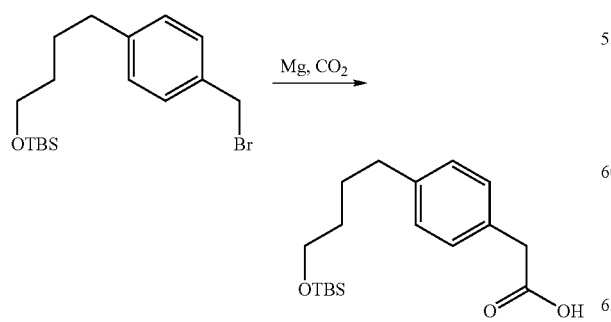

4-(4-bromomethylphenyl)butyl tert-butyldimethylsilyl ether (0.2 g, 0.561 mmol) in dry ether is added dropwise to Mg turnings (13.77 mg, 0.561 mmol). A few crystals of iodine are then added to initiate the reaction and the mixture is refluxed overnight under nitrogen atmosphere. The solution is then cooled and $CO_2$ gas is bubbled into it for 10 minutes. Stirring is continued for a further 2 hours after which water is added to the reaction mixture. The mixture is then extracted with ethyl acetate, washed and dried. After removing the organic solvent under reduced pressure the crude is purified by flash chromatography (silica gel; ethyl acetate/hexanes) to yield the desired product.

Synthesis of 2-hydroxyethyl-4-(4-tert-butyldimethylsilyloxybutyl)benzene

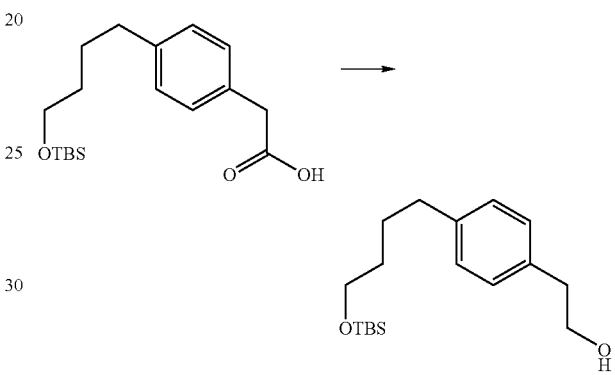

4-(4-tert-butyldimethylsilyloxybutylphenylacetic acid (0.25 g, 0.775 mmol) dissolved in dry ether is added dropwise to a suspension of lithium aluminum hydride in ether (44.2 mg, 1.16 mmol). The reaction mixture is stirred for 5 hours after which water (45 µl), NaOH (15% solution, 45 µl) and water (135 µl) are successively added and the reaction mixture is stirred for a further 30 minutes. The resulting precipitate is filtered and washed with ether. The ether filtrate is then washed with water and dried. After concentrating the ether, the product obtained is purified by flash chromatography (silica gel; ethyl acetate/hexanes)

Synthesis of 4-(2-(4-(4-tert-butyldimethylsilyloxybutyl)phenyl)ethoxy) quinazoline

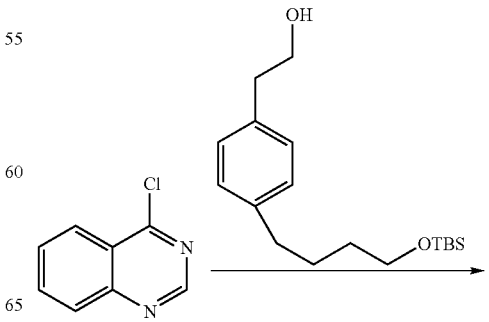

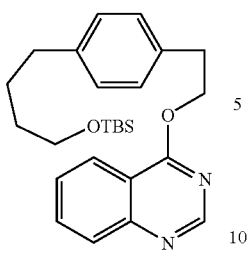

2-hydroxyethyl-4-(4-tert-butyldimethylsilyloxybutyl) benzene (0.3 g, 0.97 mmol) is dissolved in dry tetrahydrofuran and to it is added sodium hydride (24 mg, 1 mmol). The resulting solution is stirred at room temperature for 30 minutes after which 4-chloroquinazoline (0.164 g, 1 mmol) is added to the above solution. The solution is then stirred for 6 hours after which water is added to the mixture. The solution is then extracted in dichloromethane. The organic layer is washed, dried and then concentrated to yield the crude product which is purified by flash chromatography (silica gel; ethyl acetate/hexanes) to give the product.

Synthesis of
4-(2-(4-(4-hydroxybutyl)phenyl)ethoxy)quinazoline

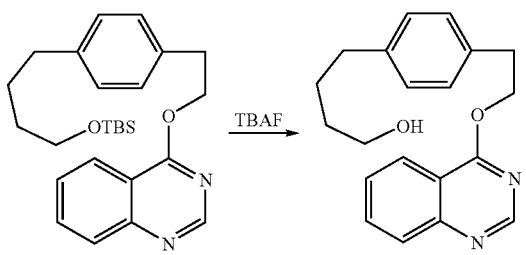

To 4-(2-(4-(4-tert-butyldimethylsilyloxybutyl)phenyl) ethoxy)quinazoline (0.4 g, 0.916 mmol) is added tetrabutylammonium fluoride solution (1M TBAF in THF, 4.58 ml, 4.58 mmol). The solution is stirred for 2 hours after which water is added to the reaction and this is extracted in ethyl acetate. The organic layer is then washed with water, dried and concentrated. The residue obtained is purified by flash chromatography (silica gel; ethyl acetate/hexanes)

Synthesis of 4-(2-(4-(4-p-toluenesulfonyloxybutyl) phenyl)ethoxy)quinazoline

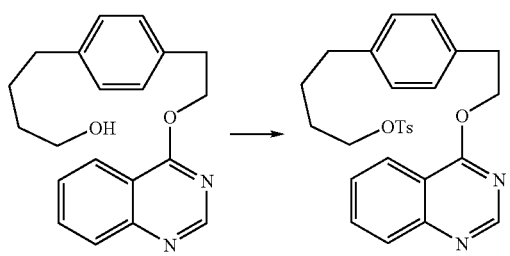

A 15 ml round bottom flask charged with 4-(2-(4-(4-hydroxybutyl)phenyl)ethoxy) quinazoline (0.25 g, 0.77 mmol) is dissolved in pyridine (5 ml). p-Toluenesulfonyl chloride (0.15 g, 0.79 mmol) is then added to it and the mixture stirred for 4 hours. The reaction mixture is diluted with ethyl acetate, washed with 5% copper sulfate solution and then with water and dried. After removing the solvent on the rotary evaporator the crude is purified by flash chromatography using silica gel (ethyl acetate/hexanes) to give the product.

Synthesis of
4-(2-(4-(4-fluorobutyl)phenyl)ethoxy)quinazoline

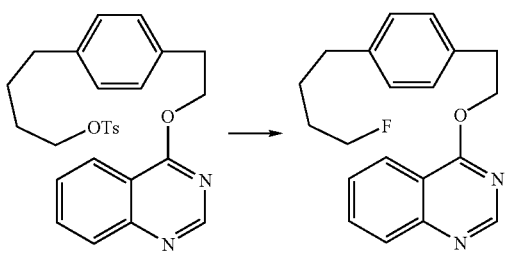

4-(2-(4-(4-p-toluenesulfonyloxybutylphenyl ethoxy) quinazoline (0.3 g, 0.63 mmol) is added to a solution of potassium fluoride/kryptofix 222 in 5 ml THF (1:1 ratio, 3.15 mmol each). After stirring at room temperature for 15 minutes the solution is then refluxed for 20 minutes. It is then cooled and water is added to it. The solution is then extracted in dichloromethane and washed with water and dried. The crude product is purified by silica gel flash chromatography (ethyl acetate/hexanes) to afford the product.

Synthesis of 4-(2-(4-(4-[$^{18}$F]-fluorobutyl)phenyl) ethoxy)quinazoline

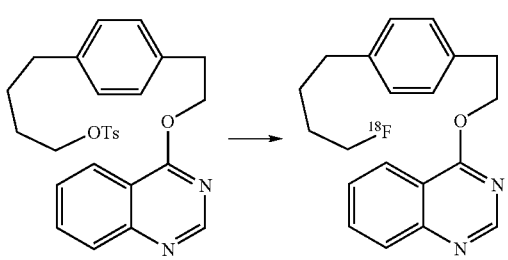

To a 5 ml reaction vial containing 100 mCi of $^{18}$F in 300 mg of $^{18}$O water is added a 1 ml solution consisting of 10 mg of Kryptofix, 1 mg potassium carbonate, 0.005 ml water and 0.95 ml acetonitrile. The vial is heated to remove all the solvents and dry acetonitrile (1 ml) is added to the vial. This is also removed by evaporation. 4-(2-(4-(4-p-toluenesulfonyloxybutyl)phenyl)ethoxy) quinazoline (5 mg) in acetonitrile is then added to it. The vial is sealed and heated for 30 minutes at 100° C. The mixture is diluted with dichloromethane and passed through a Sep-Pak and eluted with tetrahydrofuran. The solvent is evaporated to get the above mentioned compound.

Synthesis of 4-Chloro-2-quinazolone

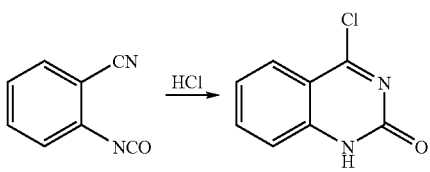

2-Cyanophenyl isocyanate (5 g, 34.7 mmol) is suspended in di-n-butyl ether. HCl gas is then passed into the suspension at 80° C. for 7 hours. The resulting precipitate is filtered, dried and recrystallized from chlorobenzene to afford the above product.

Synthesis of 4-(2-(4-tert-butylphenyl)-ethoxy)-2-quinazolone

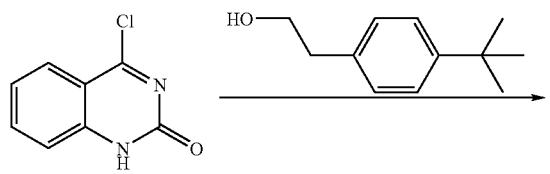

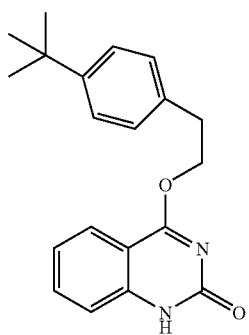

2-(4-tert-butylphenyl)ethanol (0.3 g, 1.68 mmol) is dissolved in dry tetrahydrofuran (7 ml) and to it is added sodium hydride (48.5 mg, 2.02 mmol). The resulting solution is stirred at room temperature for 30 minutes after which 4-chloro-2-quinazolone (0.302 g, 1.68 mmol) is added to the above solution. The solution is then stirred for 6 hours after which water is added to the mixture. The solution is then extracted in dichloromethane. The organic layer is washed, dried and then concentrated to yield the crude product which is purified by flash chromatography (silica gel; ethyl acetate/hexanes) to give the product.

Synthesis of 4-(2-(4-tert-butylphenyl)-ethoxy)-2-(trifluoromethanesulfonyloxy)-quinazoline

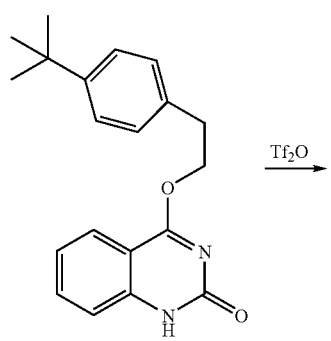

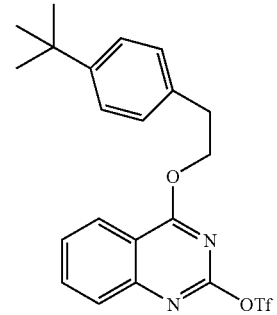

4-(2-(4-tert-butylphenyl)-ethoxy)-2-quinazolone (0.25 g, 0.775 mmol) is dissolved in dichloromethane (5 ml) and trifluoromethanesulfonic anhydride (0.328 g, 1.16 mmol and diisopropylethyl amine (0.3 g, 2.32 mmol) is added to it. The reaction is stirred overnight after which it is further diluted with dichloromethane and washed with water. The organic layer is then dried and concentrated. The crude product obtained is isolated by flash chromatography (silica gel; ethyl acetate/hexanes).

Synthesis of 4-(2-(4-tert-butylphenyl)-ethoxy)-2-fluoro-quinazoline

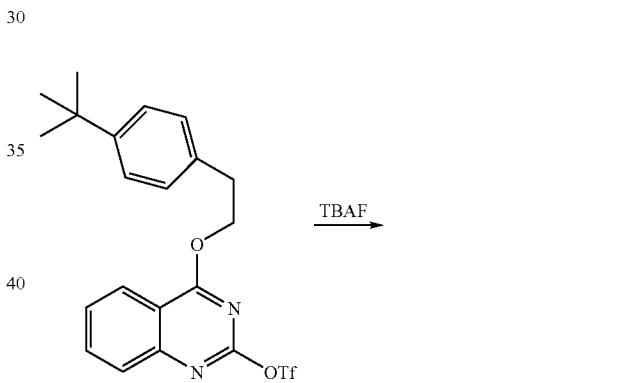

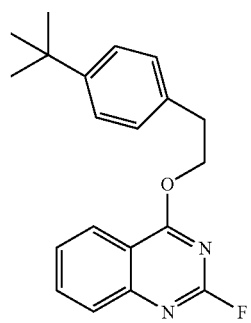

A 15 ml round bottom flask is charged with 4-(2-(4-tert-butylphenyl)-ethoxy)-2-(trifluoromethanesulfonyloxy)-quinazoline (0.3 g, 0.66 mmol). Tetrabutylammonium fluoride solution (1M in THF, 3.3 ml, 3.3 mmol) is then added to it and the solution refluxed for 60 minutes. The mixture is then cooled and water is added to it. It is then extracted with dichloromethane, washed with water and dried. The crude obtained after concentration is purified by silica gel flash chromatography (ethyl acetate/hexanes) to obtain the desired compound.

Synthesis of 4-(2-(4-tert-butylphenyl)-ethoxy)-2-[¹⁸F]-fluoro-quinazoline

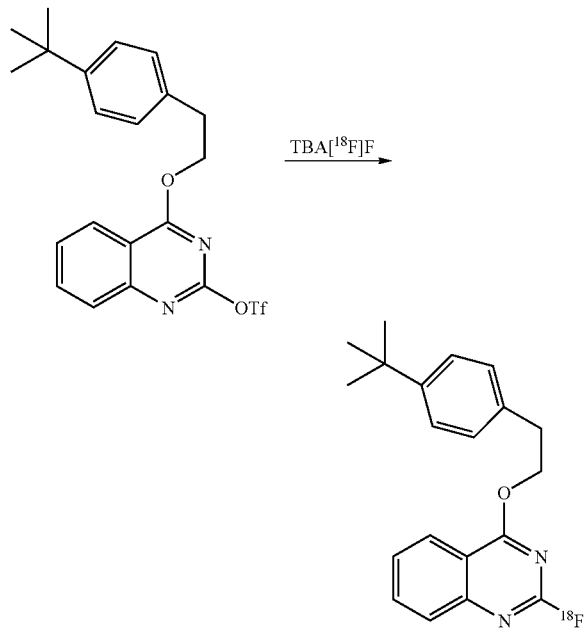

Aqueous ¹⁸F (16 mCi, 0.1 ml) is added to a vacutainer containing 5 μl of tetrabutylammonium hydroxide (40% wt sol. in water). The mixture is concentrated under nitrogen in an oil bath at 100 C and 250 μl of acetonitrile is added and this too is concentrated under nitrogen. The procedure is repeated twice and then 100 μl of acetonitrile is added to it and the contents subjected to vacuum. Without letting go dry THF is then added to it followed by 5 mg of 4-(2-(4-tert-butylphenyl)-ethoxy)-2-(trifluoromethanesulfonyloxy)-quinazoline. The mixture is then heated in an oil bath at 70° C. for 30 minutes. This is then diluted with water, applied to a C18 Sep-Pak, rinsed with water and eluted with acetonitrile to get the above mentioned compound.

Synthesis of 6-Nitro-4(3H)-quinazolone

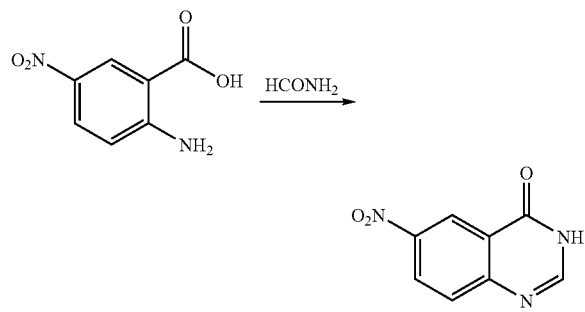

A mixture of 5-nitroanthranilic acid (2 g, 14.6 mmol) and formamide (2.9 ml, 72 mmol) is irradiated at 150 C in a microwave (power: 60 W) until TLC shows completion of reaction (20 minutes). After cooling, the reaction mixture is rinsed with ethyl acetate and evaporated under reduced pressure. The crude is purified by flash chromatography (silica gel; ethyl acetate/hexanes) to give the above product.

Synthesis of 6-Nitro-4-chloroquinoline

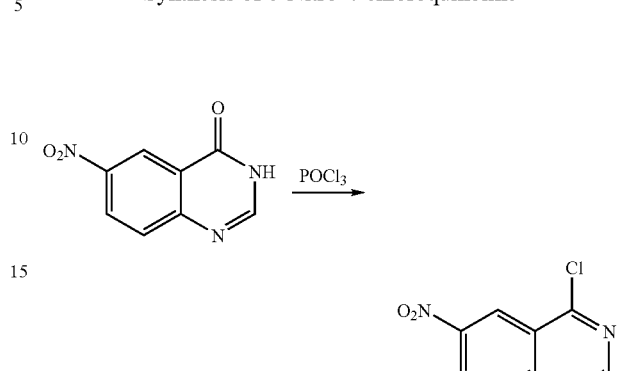

6-Nitro-4(3H)-quinazolone (1 g, 5.23 mmol) and POCl₃ (7.1 ml) are mixed together and irradiated at 10° C. tower: 70 W) for 10 minutes. The POCl₃ is evaporated in vacuo and the residue is dissolved in ethyl acetate and washed with saturated NaHCO₃, dried and concentrated. It is purified by flash chromatography (silica gel; ethyl acetate/hexanes) to give the above product.

Synthesis of 6-Nitro-4-(2-(4-tert-butylphenyl) ethoxy)quinazoline

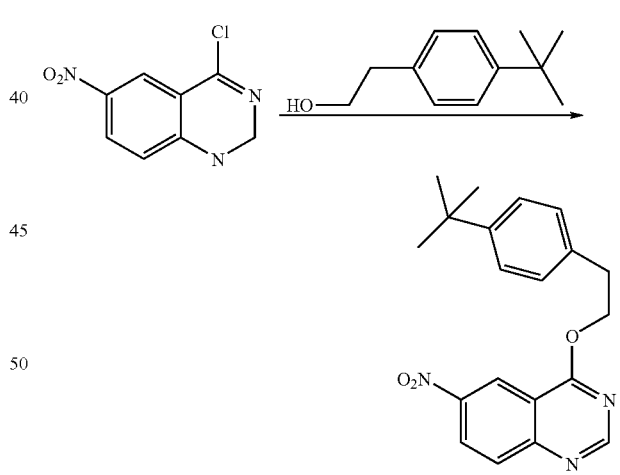

2-(4-tert-butylphenyl)ethanol (1.0 g, 5.59 mmol) is dissolved in dry tetrahydrofuran (7 ml) and to it is added sodium hydride (48.5 mg, 2.02 mmol). The resulting solution is stirred at room temperature for 30 minutes after which 6-Nitro-4-chloroquinazoline (1.17 g, 5.6 mmol) is added to the above solution. The solution is then stirred for 6 hours after which water is added to the mixture. The solution is then extracted in dichloromethane. The organic layer is washed, dried and then concentrated to yield the crude product which is purified by flash chromatography (silica gel; ethyl acetate/hexanes) to give the product.

Synthesis of 6-Fluoro-4-(2-(4-tert-butylphenyl)ethoxy)quinazoline

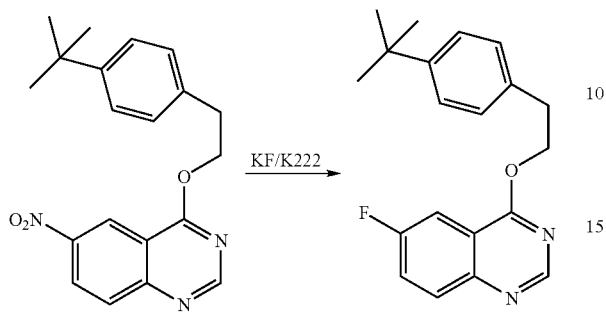

To a 25 ml round bottom flask is added potassium fluoride (82.6 mg, 1.42 mmol) and kryptofix 222 (0.53 g, 1.42 mmol). The above mixture is stirred in THF for 20 minutes after which 6-Nitro-4-(2-(4-tert-butylphenyl)ethoxy)quinazoline (0.1 g, 0.284 mmol) is added to it. The solution is refluxed for 30 minutes after which it is cooled and water is added to it. It is then extracted in dichloromethane, washed with water and dried. Purification by flash chromatography (silica gel; ethyl acetate/hexanes) gives the above compound.

Synthesis of 6-[$^{18}$F]-Fluoro-4-(2-(4-tert-butylphenyl)ethoxy)quinazoline

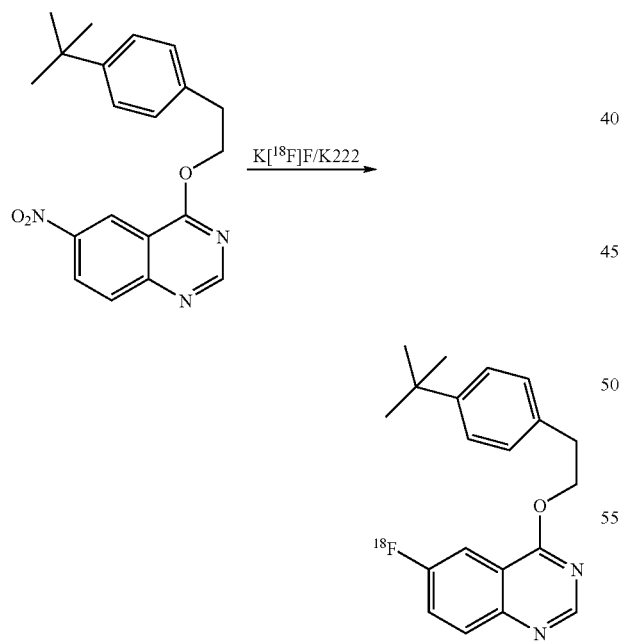

To a 5 ml reaction vial containing 50 mCi of $^{18}$F in 300 mg of $^{18}$O water is added a 1 ml solution consisting of 10 mg of Kryptofix, 1 mg potassium carbonate, 0.005 ml water and 0.95 ml acetonitrile. The vial is heated to remove all the solvents and dry acetonitrile (1 ml) is added to the vial. This is also removed by evaporation. 6-Nitro-4-(2-(4-tert-butylphenyl)ethoxy)quinazoline (5 mg) in acetonitrile is then added to it. The vial is sealed and heated for 30 minutes at 100° C. The mixture is diluted with dichloromethane and passed through a Sep-Pak and eluted with tetrahydrofuran. The solvent is evaporated to get the above mentioned compound

Synthesis of (4-tert-butylphenyl)ethane 1,2 diol

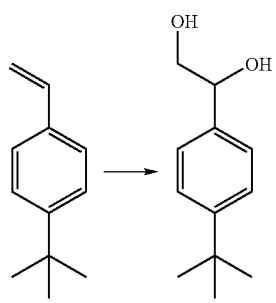

To a 100 ml round bottom flask is added 20 ml tert butanol, 20 ml of water and 5.6 g of AD-mix-β. The solution is stirred and cooled to 0° C. tert-butyl styrene (0.64 g, 4 mmol) is added to the mixture and the resulting solution is stirred overnight at 0° C. Sold sodium sulfite (6 g) is added and the mixture stirred for an additional 30 minutes. The solution is then extracted in ethyl acetate, washed with water and dried. The crude is then purified by flash chromatography (silica gel; ethyl acetate/hexanes) to afford the product.

Synthesis of 1-tert-butyldimethylsilyloxy-2-hydroxy-2-(4-tertbutylphenyl)ethane

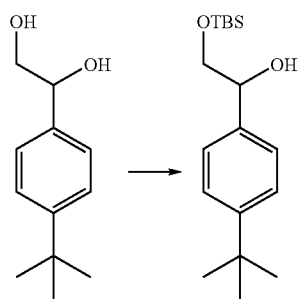

(4-tert-butylphenyl)ethane 1,2 diol (0.5 g, 2.57 mmol) is dissolved in DMF in a 25 ml round bottom flask and to this were added imidazole (0.210 g, 3.09 mmol) and tert-butyldimethylsilyl chloride (0.46 g, 3.09 mmol). The mixture is stirred for 6 hours after which it is extracted in dichloromethane and the organic layer washed with water and dried. Purification by flash chromatography (silica gel; ethyl acetate/hexanes) affords the above mentioned product.

Synthesis of 1-tert-butyldimethylsilyloxy-2-tetrahydropyranyloxy-2-(4-tertbutylphenyl)ethane

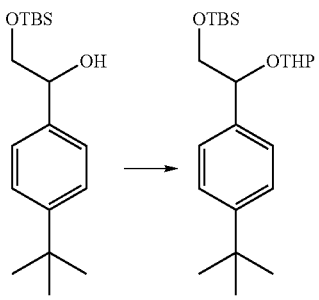

1-Tert-butyldimethysilyloxy-2-hydroxy-2-(4-tert-butylphenyl)ethane (0.5 g, 1.622 mmol) is dissolved in dichloromethane and to it is added dihydropyran (0.163 g, 0.94 mmol) and toluenesulfonic acid (33 mg, 0.194 mmol). The reaction is stirred for 2 hours after which the mixture is washed with water and dried. The crude residue obtained after concentration is purified by flash chromatography (silica gel; ethyl acetate/hexanes) to obtain the product.

Synthesis of 1-hydroxy-2-tetrahydropyranyloxy-2-(4-tert-butylphenyl)ethane

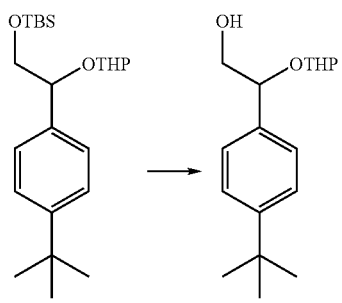

To 1-tert-butyldimethylsilyloxy-2-tetrahydropyranyloxy-2-(4-tertbutylphenyl)ethane (0.4 g, 1.01 mmol) is added tetrabutylammonium fluoride solution (1M TBAF in THF, 5 ml, 5.0 mmol). The solution is stirred for 2 hours after which water is added to the reaction and this is extracted in ethyl acetate. The organic layer is then washed with water, dried and concentrated. The residue obtained is purified by flash chromatography (silica gel; ethyl acetate/hexanes).

Synthesis of 4-(2-tetrahyropyranyloxy-2-(4-tert-butylphenyl)ethoxy) quinazoline

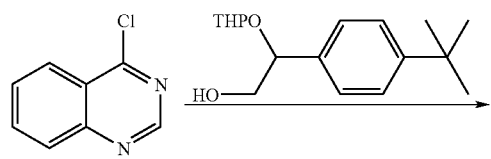

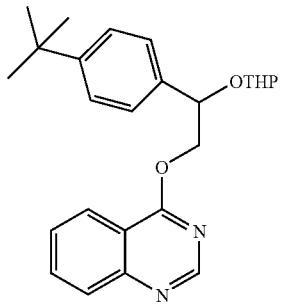

1-Hydroxy-2-tetrahydropyranyloxy-2-(4-tert-butylphenyl)ethane (0.3 g, 1.07 mmol) is dissolved in dry tetrahydrofuran (7 ml) and to it is added sodium hydride (30.96 mg, 1.29 mmol). The resulting solution is stirred at room temperature for 30 minutes after which 4-chloroquinazoline (0.175 g, 1.07 mmol) is added to the above solution. The solution is then stirred for 6 hours after which water is added to the mixture. The solution is then extracted in dichloromethane. The organic layer is washed, dried and then concentrated to yield the crude product which is purified by flash chromatography (silica gel; ethyl acetate/hexanes) to give the product.

Synthesis of 4-(2-hydroxy-2-(4-tert-butylphenyl)ethoxy)quinazoline

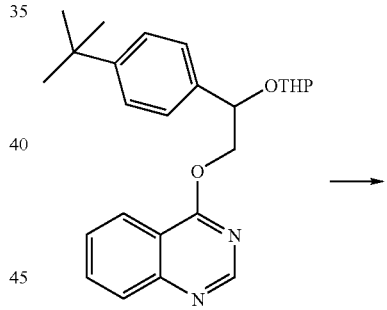

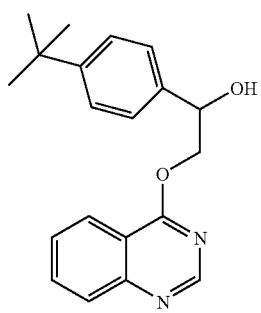

4-(2-tetrahyropyranyloxy-2-(4-tert-butylphenyl)ethoxy) quinazoline (0.25 g, 0.615 mmol) is dissolved in 5 ml ethanol and pyridinium-p-toluenesulfonate (15.4 mg, 0.061 mmol) is added to it. The solution is heated to 55° C. and stirred at that temperature for 4 hours. The ethanol is removed and the crude is purified by flash chromatography (silica gel; ethyl acetate/hexanes).

Synthesis of 4-(2-p-toluenesulfonyloxy-2-(4-tert-butylphenyl)ethoxy) quinazoline

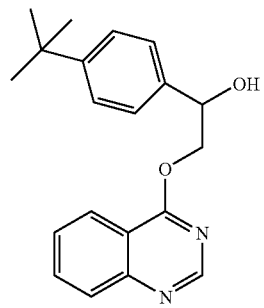

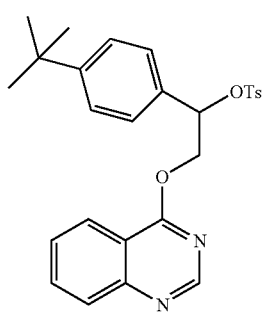

A 15 ml round bottom flask is charged with 4-(2-hydroxy-2-(4-tert-butylphenyl)ethoxy) quinazoline (0.25 g, 0.77 mmol) is dissolved in pyridine (5 ml). p-Toluenesulfonyl chloride (0.15 g, 0.79 mmol) is then added to it and the mixture stirred for 4 hours. The reaction mixture is diluted with ethyl acetate, washed with 5% copper sulfate solution and then with water and dried. After removing the solvent on the rotary evaporator the crude is purified by flash chromatography using silica gel (ethyl acetate/hexanes) to give the product.

Synthesis of 4-(2-fluoro-2-(4-tert-butylphenyl)ethoxy)quinazoline

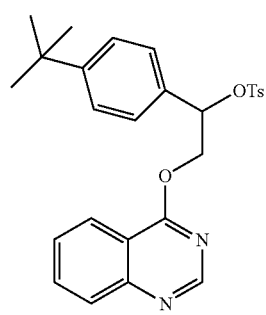

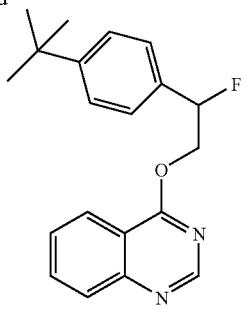

A 15 ml round bottom flask is charged with 4-(2-p-toluenesulfonyloxy-2-(4-tert-butylphenyl)ethoxy)quinazoline (0.3 g, 0.84 mmol). Tetrabutylammonium fluoride solution (1M in THF, 4.2 ml, 4.2 mmol) is then added to it and the solution is heated at reflux for 60 minutes. The mixture is then cooled and water is added to it. It is then extracted with dichloromethane, washed with water and dried. The crude obtained after concentration is purified by silica gel flash chromatography (ethyl acetate/hexanes) to obtain the desired compound.

Synthesis of 4-(2-[$^{18}$F]-fluoro-2-(4-tert-butylphenyl)ethoxy)quinazoline

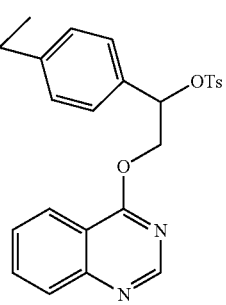

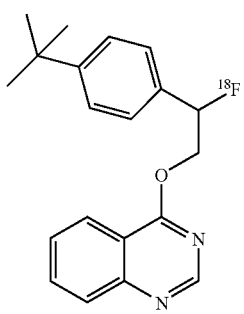

Aqueous $^{18}$F (16 mCi, 0.1 ml) is added to a vacutainer containing 5 μl of tetrabutylammonium hydroxide (40% wt sol. in water). The mixture is concentrated under nitrogen in an oil bath at 1100° C. and 250 μl of acetonitrile is added and this too is concentrated under nitrogen. The procedure is repeated twice and then 100 μl of acetonitrile is added to it and the contents subjected to vacuum. Without letting go dry THF is then added to it followed by 5 mg of 4-(2-p-toluenesulfonyloxy-2-(4-tert-butylphenyl)ethoxy) quinazoline. The mixture is then heated in an oil bath at 70° C. for 30 minutes. This is then diluted with water, applied to a C18 Sep-Pak, rinsed with water and eluted with acetonitrile to get the above mentioned compound.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein,

What is claimed is:

1. A method for detecting, imaging or monitoring myocardial perfusion, comprising:

administering to a patient a sterile formulation comprising a compound of the following formula:

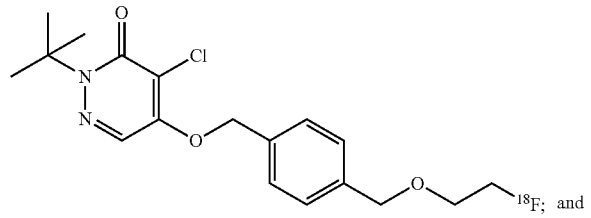

scanning the patient using diagnostic imaging.

2. A method for detecting, imaging, or monitoring myocardial perfusion, comprising:

administering to a patient a contrast agent; and
scanning the patient using diagnostic imaging,
wherein the contrast agent is

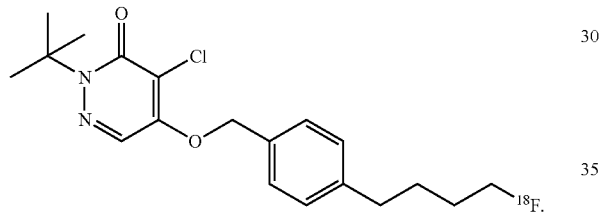

3. A method for detecting, imaging, or monitoring myocardial perfusion, comprising:

administering to a patient a contrast agent; and
scanning the patient using diagnostic imaging,
wherein the contrast agent is

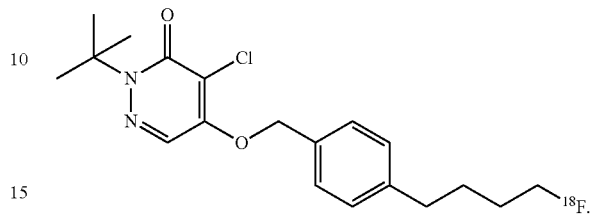

4. A method for detecting, imaging, or monitoring myocardial perfusion, comprising:

administering to a patient a contrast agent; and
scanning the patient using diagnostic imaging,
wherein the contrast agent is

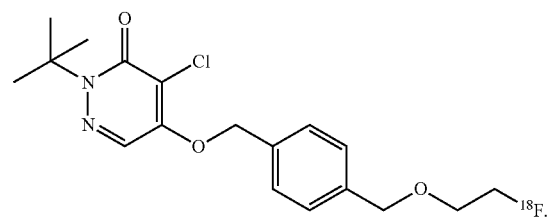

* * * * *

UNITED STATES PATENT AND TRADEMARK OFFICE
CERTIFICATE OF CORRECTION

| | | |
|---|---|---|
| PATENT NO. | : 8,226,929 B2 | |
| APPLICATION NO. | : 12/014161 | |
| DATED | : July 24, 2012 | |
| INVENTOR(S) | : David S. Casebier et al. | |

It is certified that error appears in the above-identified patent and that said Letters Patent is hereby corrected as shown below:

At column 121, claim 2, lines 30-35, please correct the chemical formula to display an "S" instead of "O" so the chemical formula is displayed as follows:

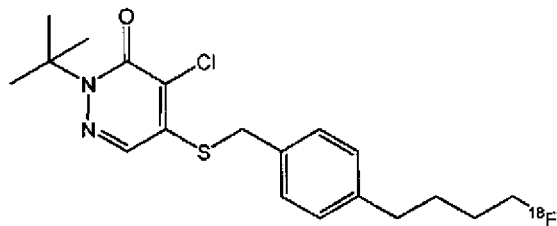

Signed and Sealed this
Twenty-third Day of October, 2012

David J. Kappos
*Director of the United States Patent and Trademark Office*